US012253513B2

(12) United States Patent
Talebpour et al.

(10) Patent No.: US 12,253,513 B2
(45) Date of Patent: Mar. 18, 2025

(54) METHODS AND COMPOSITIONS FOR THE SELECTIVE LYSIS OF BLOOD CELLS AND SEPARATION OF MICROBIAL CELLS

(71) Applicant: QVELLA CORPORATION, Richmond Hill (CA)

(72) Inventors: Samad Talebpour, Richmond Hill (CA); Aye Aye Khine, Thornhill (CA); Vilcy Parmar, North York (CA); Sukhdev Manku, Toronto (CA); Alaleh Samiei, Richmond Hill (CA)

(73) Assignee: QVELLA CORPORATION, Richmond Hill (CA)

( * ) Notice: Subject to any disclaimer, the term of this patent is extended or adjusted under 35 U.S.C. 154(b) by 853 days.

(21) Appl. No.: 17/057,088

(22) PCT Filed: May 24, 2019

(86) PCT No.: PCT/CA2019/050716
§ 371 (c)(1),
(2) Date: Nov. 19, 2020

(87) PCT Pub. No.: WO2019/222862
PCT Pub. Date: Nov. 28, 2019

(65) Prior Publication Data
US 2021/0208128 A1    Jul. 8, 2021

Related U.S. Application Data

(60) Provisional application No. 62/776,126, filed on Dec. 6, 2018, provisional application No. 62/676,771, filed on May 25, 2018.

(51) Int. Cl.
*G01N 33/49*    (2006.01)
*G01N 35/00*    (2006.01)

(52) U.S. Cl.
CPC ........... *G01N 33/491* (2013.01); *G01N 35/00* (2013.01); *G01N 2035/00495* (2013.01)

(58) Field of Classification Search
CPC ................. G01N 33/491; G01N 35/00; G01N 2035/00495
See application file for complete search history.

(56) References Cited

U.S. PATENT DOCUMENTS

| | | |
|---|---|---|
| 3,883,425 A | 5/1975 | Dorn |
| 4,131,512 A | 12/1978 | Dorn |
| 4,164,449 A | 8/1979 | Dorn et al. |
| 4,212,948 A | 7/1980 | Dorn |
| 4,693,972 A | 9/1987 | Mansour et al. |
| 5,070,014 A | 12/1991 | Dorn |
| 5,108,927 A | 4/1992 | Dorn |
| 5,501,960 A | 3/1996 | Dorn |
| 5,840,515 A | 11/1998 | Provost |
| 6,114,130 A | 9/2000 | Veriac et al. |
| 6,803,208 B2 | 10/2004 | Seaver et al. |
| 6,864,100 B1 | 3/2005 | Ribbe et al. |
| 7,247,484 B2 | 7/2007 | Wu et al. |
| 7,939,249 B2 | 5/2011 | Parthasarathy et al. |
| 8,507,237 B2 | 8/2013 | Hermet et al. |
| 8,603,769 B2 | 12/2013 | Feng et al. |
| 8,741,136 B2 | 6/2014 | Peters et al. |
| 8,975,060 B2 | 3/2015 | Talebpour et al. |
| 9,574,219 B2 | 2/2017 | Ronsick et al. |
| 10,308,976 B2 | 6/2019 | Van Meerbergen et al. |
| 2004/0142318 A1* | 7/2004 | Wu .................... G01N 33/5094 435/4 |
| 2006/0102478 A1 | 5/2006 | Robert et al. |
| 2008/0234474 A1 | 9/2008 | Braman et al. |
| 2011/0061474 A1 | 3/2011 | Page et al. |
| 2011/0294128 A1 | 12/2011 | Peytavi et al. |
| 2012/0115705 A1 | 5/2012 | Sharon et al. |

(Continued)

FOREIGN PATENT DOCUMENTS

CA    2892813    6/2014
EP    0187266 A1    7/1986
(Continued)

OTHER PUBLICATIONS

Bodansky, "The effect of Hydrogen Ion Concentration on Saponin Hemolysis" Journal of Biological Chemistry. vol. 82, Issue 3, Jun. 1929, pp. 567-577 (Year: 1929).*
Sergey Zelenin et al., "Bacteria Isolation From Whole Blood for Sepsis Diagnostics", 15th International Conference, Oct. 2011, 518-520.
Jinwag Tan et al., "Kinetically limited dififferential centrifugation as an inexpensive and readily available alternative to centrifugal elutriation", BioTechniques, vol. 53, No. 2, Aug. 2012, pp. 104-108.
"Accessing Microbial Safety of Drinking Water", World Health Organization, pp. 1-192.
S. Wilfred Ruban et al., "Physical Methods of Separation and Concentration of Microbes in Food: an Aid for Rapid Detection", Journal of Food Technology 9(3): 106-111, 2011.

(Continued)

*Primary Examiner* — Ryan B Huang
(74) *Attorney, Agent, or Firm* — HILL & SCHUMACHER

(57) ABSTRACT

Methods and compositions are provided for the selective lysis of eukaryotic cells and the separation of microbial cells. Blood cells and/or other eukaryotic cells in a sample, may be selectively lysed by adding, to the sample, a blood lysis reagent including saponin and an alkaline buffer, and optionally sodium polyanethole sulfonate and a non-ionic surfactant, thereby forming a mixture, and agitating the mixture. Microbial cells in the mixture may then be separated, for example, using a separation method such as centrifugation or filtration, and optionally detected or cultured in growth media. Blood lysis reagent compositions are provided that are suitable for preserving the intactness of microbial cells upon mixing with the sample. In example embodiments in which the sample is a blood sample, the blood lysis reagent composition may be selected to avoid or reduce the presence of visible blood debris upon centrifugation or filtration.

38 Claims, 39 Drawing Sheets

(56) References Cited

U.S. PATENT DOCUMENTS

| | | |
|---|---|---|
| 2012/0190040 A1 | 7/2012 | Talebpour et al. |
| 2012/0231446 A1 | 9/2012 | Heckel et al. |
| 2013/0171615 A1 | 7/2013 | Van Meerbergen et al. |
| 2014/0004501 A1 | 1/2014 | Talebpour et al. |
| 2014/0051113 A1* | 2/2014 | Stephenson, Jr. .. G01N 33/6848 435/288.6 |
| 2014/0370508 A1 | 12/2014 | Grobler et al. |
| 2015/0125895 A1 | 5/2015 | Kircher et al. |
| 2017/0275612 A1 | 9/2017 | Talebpour et al. |
| 2017/0356018 A1* | 12/2017 | Sun ................ A23D 9/04 |

FOREIGN PATENT DOCUMENTS

| | | | |
|---|---|---|---|
| EP | 0499364 A1 | 8/1992 | |
| EP | 0745849 | 12/1996 | |
| JP | 61136406 A | 6/1986 | |
| JP | 538403 A | 2/1993 | |
| JP | 2002193825 A | 7/2002 | |
| JP | 2006145537 A | 6/2006 | |
| JP | 200745788 A | 2/2007 | |
| JP | 2016500008 A | 1/2016 | |
| JP | 2017527301 A | 9/2017 | |
| WO | 2008122002 | 10/2008 | |
| WO | 2010062354 | 6/2010 | |
| WO | WO-2014082160 A1 * | 6/2014 | ........... B01L 3/5021 |
| WO | 2014193481 | 12/2014 | |
| WO | 2016044621 A1 | 3/2016 | |

OTHER PUBLICATIONS

Biochemistry and Molecular Biology, Chapter 3, "Centrifugation", pp. 1-60.

As Friberg et al., "Human islet separation utilizing a closed automated purification system", Cell Transplant, 2008; 17(12):1305-13.

John R. Gordan, PHD, "Immunology Methods Manual, Selected Protocol", jrg426, pp. 1-3.

Jan Koolman et al., "Color Atlas of Biochemistry", Koolman, 2nd edition, 2005, pp. 1-476.

Lin Lin et al., "Use of the Sucrose Gradient Method for Bacterial Cell Cycle Synchronization", Journal of Microbiology, 2014, pp. 1-4.

David Ammons et al., "An apparatus to control and automate the formation of continuous density gradients", Analytical Biochemistry 427 (2012) 124-126.

Gilbert, "Centrifugation injury of Gram-negative bacteria, Dept of Clinical Microbiology", Sweden, pp. 1-2.

Mathias Bernhardt et al., "Detection of Bacteria in Blood by Centrifugation and Filtration", Journal of Clinical Microbiology, Mar. 1991, pp. 422-425.

R. Blaine McCleskey, "Electrical Conductivity of Electrolytes Found in Natural Waters From (5 to 90)", J. Chem. Eng. Data 2011, 56, 317-327.

B. Arkles et al., "Silanes Surfaces and Interfaces, Surfaces and Interfaces Symposium", Colorodo, Jun. 19-21, 1985, pp. 1-17.

R. Phillip Dellinger et al., "Surviving Sepsis Campaign: International guidelines for management of sever sepsis and septic shock: 2008", Intensive Care Med (2008) 34:17-60.

Verne Schumaker et al., "Theory of Differential Centrifugation in Angle-Head Rotors", Analytical Biochemistry 31, 279-285, 1969.

David N. Fredricks et al., "Improved Amplification of Microbial DNA from Blood Cultures by Removal of the PCR Inhibitor Sodium Polyanetholesulfonate", Journal of Clinical Microbiology, Oct. 1998, p. 2810-2816.

Walfeed Abu AL-Soud et al., "Purification and Characterization fo PCR-Inhibitory Components in Blood Cells", Journal of Clincial Microbiology, Feb. 2001, p. 485-493.

International Search Report in PCT/CA2019/050716 dated Aug. 16, 2019.

International Search Report in PCT/CA2013/000992 dated Mar. 28, 2014.

G.L. Dorn et al., "Copyright (1978 American Society for Microbiology New Centrifugation Blood Culture Device". Journal of clinical Microbiology, Jan. 1, 1978, pp. 52-54.

Herbert Wiesinger-Mayr et al.: "Establishment of a semi-automated pathogen DNA isolation from whole blood and comparison with commercially available kits", Journal of Microbiological Methods, Elsevier, Amsterdam, NL vol. 85, No. 3, Mar. 6, 2011.

Yagupsky, Pablo, and Frederick S. Nolte. "Quantitative aspects of septicemia." Clinical microbiology reviews 3.3 (1990): 269.

Mendonca, Aubrey F., Terry L. Amoroso, and Stephen J. Knabel. "Destruction of gram-negative food-borne pathogens by high pH involves disruption of the cytoplasmic membrane." Applied and environmental microbiology 60.11 (1994): 4009.

Zierdt, Charles H. "Blood-lysing solution nontoxic to pathogenic bacteria." Journal of clinical microbiology 15.1 (1982): 172.

\* cited by examiner

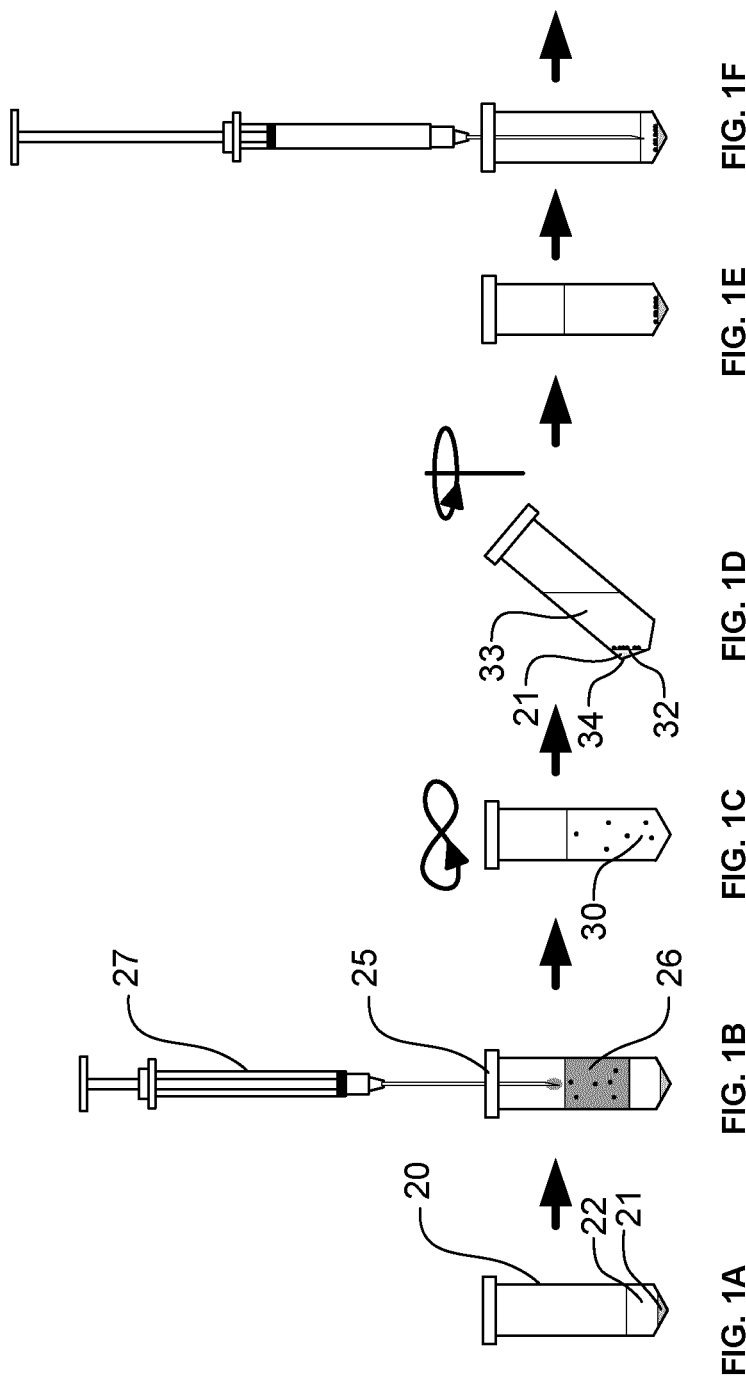

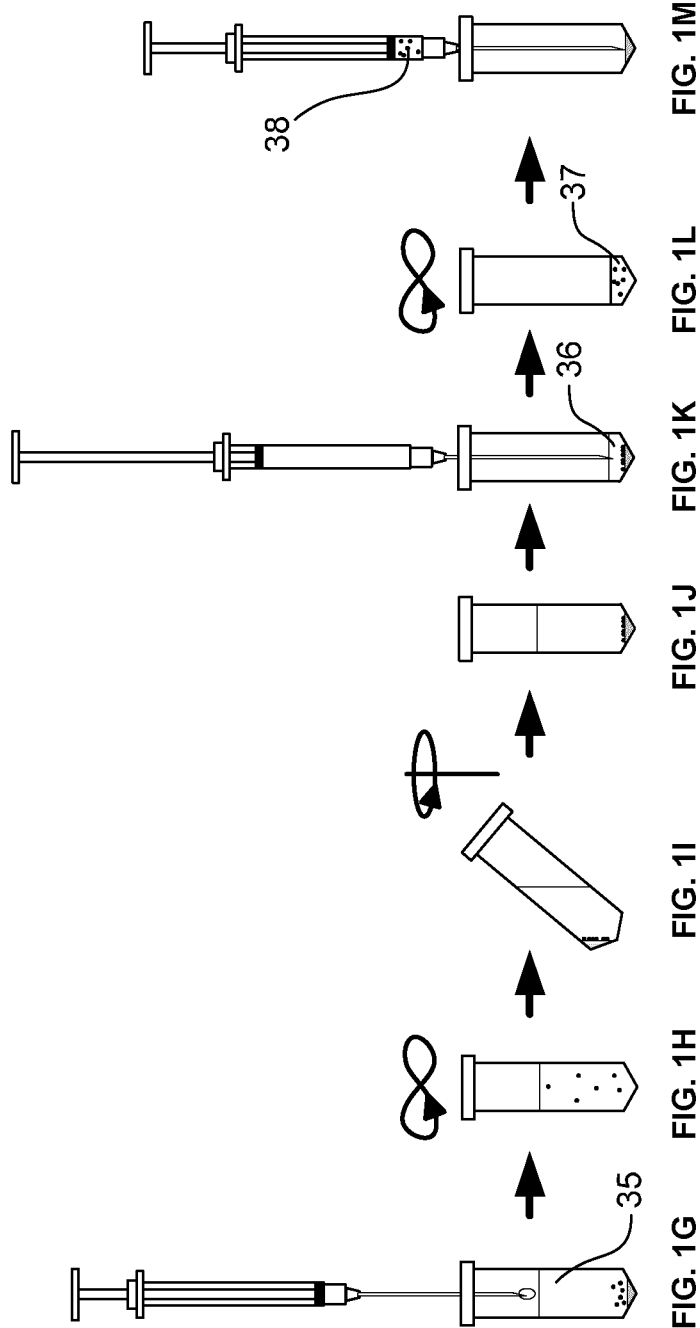

|    | Triton-100X (ΔCT) | Tween-20 (ΔCT) |
|----|-------------------|----------------|
| PA | 2.59              | 2.22           |
| PM | 1.74              | 1.29           |
| SA | 1.96              | 2.03           |

FIG.11B

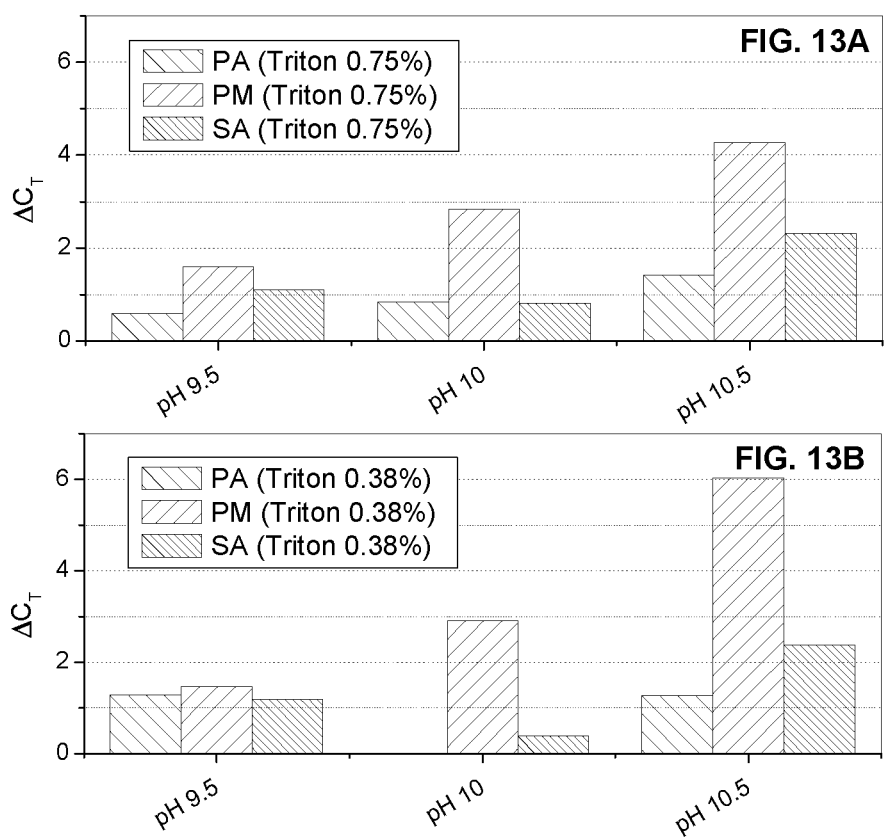

| Molar ratio of NaHCO$_3$ to Na$_2$CO$_3$ in 1.0M buffer solution | pH of 1.0M bicarb/carb solution (in water) | pH and bicarb/carb conc. of diluted solution (in water) | pH and bicarb/carb conc. of the resultant BLR | pH and bicarb/carb conc. in 5:3 BLR (with bicarb/carb) and blood |
|---|---|---|---|---|
| 1 to 1 | 9.5 (1000mM) | 9.66 (400mM) | 9.65 (200mM) | 9.45 (125mM) |
| Approx 1 to 4 | 10.0 (1000mM) | 10.19 (200mM) | 9.97 (100mM) | 9.52 (62.5mM) |
| 1 to 12.5 | 10.5 (1000mM) | 10.78 (120mM) | 10.23 (60mM) | 9.56 (37.5mM) |

| Different Buffer System (pH10) | pH before mixing | pH after mixing |
|---|---|---|
| Carbonate | 9.43 | 9.29 |
| CAPS | 9.47 | 9.10 |
| CHES | 9.55 | 9.06 |

| Antifoam | Foam height of 1mL of HR5_1 after vigorous shaking | Differences in CT values (1mL of treated BLR-TSS + 1mL of PB) from untreated sample | | |
|---|---|---|---|---|
| | | PM | PA | SA |
| 0.2% AF204 | 25-15mm | | | |
| 0.05% AF204 | 15mm | | | |
| 0.01% PPG400 | 10mm | -0.25 | 1.1 | 1.0 |
| 0.2% AF204 and 0.02% PPG4000 | 3.5mm – 10mm | 0.8 | 0.54 | 0.09 |
| 0.1% AF204 and 0.01% PPG4000 | 3.5mm – 10mm | 0.07 | 0.07 | 0.01 |
| 0.05% SE-15 | 2.5mm | -0.37 | -0.48 | -1.23 |
| 0.1% SE-15 | ~1mm | 0.57 | -0.08 | -1.26 |
| 0.2% SE-15 | <1mm | 0.36 | -0.06 | -1.78 |
| untreated | 25mm | | | |

FIG. 17A

| Time (s) | Height (mm); Without HR3 | Height (mm); HR5 |
|---|---|---|
| 0 | 55 | 12 |
| 10 | 55 | 5 |
| 20 | 55 | 0 |

| Stability at room temperature | | | Differences in CT values (1mL of treated HR + 1mL of 200 CFU in PB) from control (1mL of PB with 1mL of 200 CFU in PB) | | |
|---|---|---|---|---|---|
| Lysing reagent | Antifoaming agent | Storage time at room temp. | PM | PA | SA |
| HR3 | none | 12 days | 3.4 | 0.41 | -0.99 |
| HR5 | 0.05% SE-15 | 12 days | 3.77 | 0.39 | -1.15 |

FIG. 17D

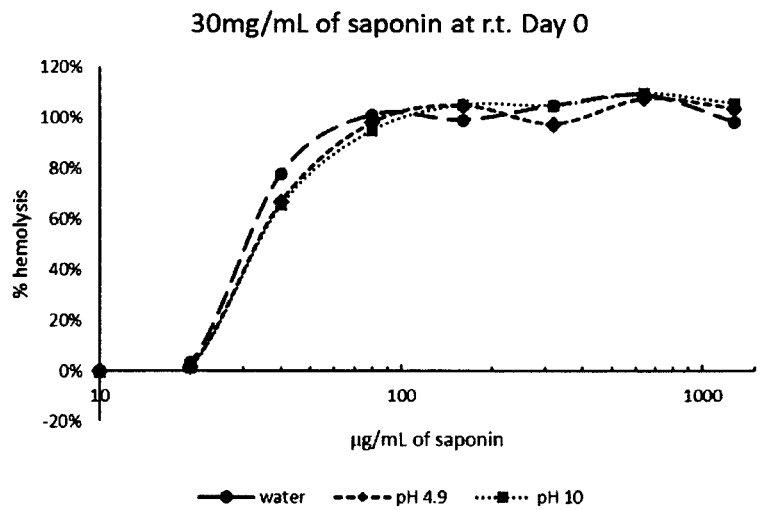
FIG. 18A
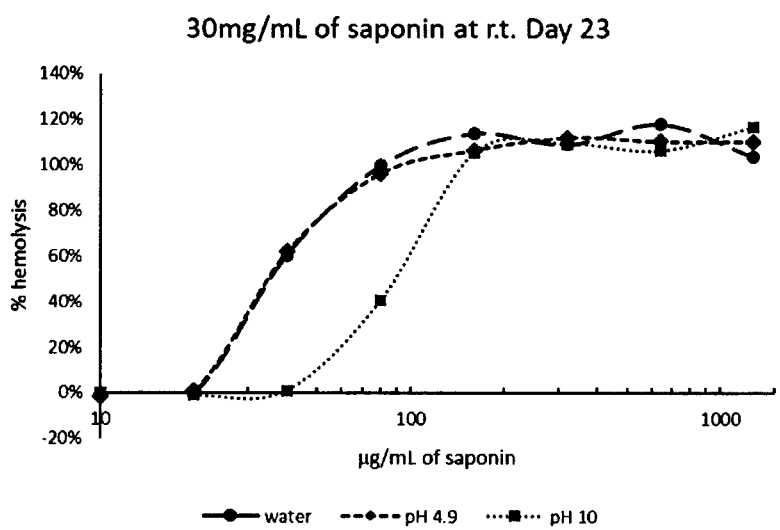
FIG. 18B
FIG. 18C
| Saponin storage buffer | Unbuffered (pH~4.3) | 60mM Acetate (pH ~4.9) | 100mM Bicarb (pH ~9.8) |
|---|---|---|---|
| Day 0 | 35.0 | 35.8 | 35.7 |
| Day 23 | 39.1 | 38.0 | 89.1 |

| Type 3 Blood Lysis Reagent | | | | VITEK-MS-ID | | |
|---|---|---|---|---|---|---|
| Saponin | SPS | TritonX-100 | Buffer | % confidence | | |
| mg/mL | mg/mL | % | mM | S.aureus | E.coli | P.aeruginosa |
| Reagent 1 | 17.5 | 10 | 0.75 | 50 | 99.9 | 99.9 | 99.9 |
| Reagent 2 | 17.5 | 10 | 0 | 50 | 99.9 | 99.9 | 99.9 |
| Reagent 3 | 17.5 | 10 | 0 | 25 | 99.9 | 99.9 | 99.9 |

FIG. 21C

| Sample | Experiment | VITEK-MS-ID | |
|---|---|---|---|
| Type | Wash # | Correct ID | |
| K. pneumoniae ATCC 700603 | | % confidence | %correct ID |
| Cell Suspension | 1 | Not detected | N/A |
| | 2 | 99.9 | 100 |
| | 3 | 99.5 | 100 |
| | 4 | 99.2 | 100 |
| Positive Colony Control | | 99.9 | Reference |

FIG. 21D

*Proteus mirabilis*

*Pseudomonas aeruginosa*

|  | Plate Count | | |
|---|---|---|---|
|  | Control | 50 mM Carbonate buffer pH 10 no Triton X-100 | 25 mM Carbonate buffer pH 10 no Triton X-100 |
| PA | 23 | 18 | 19 |
| PM | 44 | 34 | 38 |
| SA | 15 | 9 | 12 |

| Sample Type | S. aureus Strain # | VITEK-MS-ID Correct ID | |
|---|---|---|---|
| | | % confidence | %correct ID |
| Cell Suspension | ATCC 14775 | 99.9 | 100 |
| | ATCC 11632 | 99.9 | |
| Positive Colony Control | ATCC 14775 | 99.9 | Reference |
| | ATCC 11632 | 99.9 | |

| Sample Type | S. aureus Strain # | VITEK2 | | |
|---|---|---|---|---|
| | | VITEK2- ID | | VITEK2-AST |
| | | % probability | % correct ID | % category agreement |
| Cell Suspension | ATCC 14775 | 98 | 100 | 100 |
| | ATCC 11632 | 98 | 100 | 100 |
| Positive Colony Control | ATCC 14775 | 99.9 | Reference | Reference |
| | ATCC 11632 | 99.9 | | |

FIG. 24A

| Sample Type | E. coli Strain # | VITEK-MS-ID Correct ID | |
|---|---|---|---|
| | | % confidence | %correct ID |
| Cell Suspension | ATCC 10536 | 99.9 | 100 |
| | ATCC 43888 | 99.4 | |
| Positive Colony Control | ATCC 10536 | 99.9 | Reference |
| | ATCC 43888 | 99.9 | |

| Sample Type | E. coli Strain # | VITEK2 | | |
|---|---|---|---|---|
| | | VITEK2- ID | | VITEK2-AST |
| | | % probability | % correct ID | % category agreement |
| Cell Suspension | ATCC 10536 | 99 | 100 | 100 |
| | ATCC 43888 | 97 | 100 | 100 |
| Positive Colony Control | ATCC 10536 | 99 | Reference | Reference |
| | ATCC 43888 | 99 | | |

FIG. 24B

| Sample Type | P. aeruginosa Strain # | VITEK-MS-ID Correct ID | |
|---|---|---|---|
| | | % confidence | %correct ID |
| Cell Suspension | ATCC 27853 | 99.9 | 100 |
| | ATCC 25619 | 99.9 | |
| Positive Colony Control | ATCC 27853 | 99.9 | Reference |
| | ATCC 25619 | 99.9 | |

| Sample Type | P. aeruginosa Strain # | VITEK2 | | |
|---|---|---|---|---|
| | | VITEK2- ID | | VITEK2-AST |
| | | % probability | % correct ID | % category agreement |
| Cell Suspension | ATCC 27853 | 96 | 100 | 100 |
| | ATCC 25619 | 97 | 100 | 100 |
| Positive Colony Control | ATCC 27853 | 96 | Reference | Reference |
| | ATCC 25619 | 95 | | |

FIG. 24C

| Sample Type | K. pneumoniae Strain # | VITEK-MS-ID Correct ID | |
|---|---|---|---|
| | | % confidence | %correct ID |
| Cell Suspension | ATCC 700603 | 99.9 | 100% |
| | ATCC 13883 | 99.9 | |
| Positive Colony Control | ATCC 700603 | 99.9 | Reference |
| | ATCC 13883 | 99.9 | |

| Sample Type | K. pneumoniae Strain # | VITEK2 | | |
|---|---|---|---|---|
| | | VITEK2- ID | | VITEK2-AST |
| | | % probability | % correct ID | % category agreement |
| Cell Suspension | ATCC 700603 | 99 | 100 | 94 |
| | ATCC 13883 | 99 | 100 | 100 |
| Positive Colony Control | ATCC 700603 | 98 | Reference | Reference |
| | ATCC 13883 | 99 | | |

FIG. 24D

| Organisms | Average Spiking concentration | Average Viable cell recovery | VITEK-MS | VITK2-ID | VITK2-AST |
|---|---|---|---|---|---|
| | CFU/mL | % of spiking control | % correct ID | % correct ID | % Category Agreement |
| Gram-positive bacteria | 9 | 92 | 100 | 100 | 99 |
| Gram-negative bacteria | 5 | 95 | 100 | 100 | 98 |
| Yeast | 6 | 140 | 100 | 100 | 100 |

FIG. 25

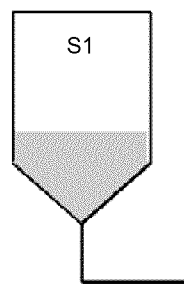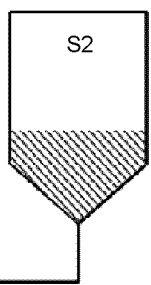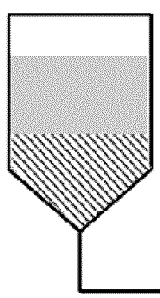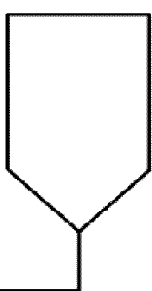
FIG. 26A       FIG. 26B

METHODS AND COMPOSITIONS FOR THE SELECTIVE LYSIS OF BLOOD CELLS AND SEPARATION OF MICROBIAL CELLS

CROSS-REFERENCE TO RELATED APPLICATION

This application is a National Phase application claiming the benefit of the international PCT Patent Application No. PCT/CA2019/050716, filed on May 24, 2019, in English, which claims priority to U.S. Provisional Patent Application No. 62/676,771, titled "METHODS AND COMPOSITIONS FOR THE SELECTIVE LYSIS OF EUKARYOTIC CELLS" and filed on May 25, 2018, the entire contents of which are incorporated herein by reference, and also claims priority to U.S. Provisional Application No. 62/776,126, titled "METHODS AND COMPOSITIONS FOR THE SELECTIVE LYSIS OF BLOOD CELLS AND SEPARATION OF MICROBIAL CELLS" and filed on Dec. 6, 2018, the entire contents of which is incorporated herein by reference.

BACKGROUND

The emergence of drug resistant pathogens is a global healthcare crisis that is forcing physicians to treat common infectious diseases with ever more potent antibiotics. This is largely caused by the complexity and time required in identifying the offending pathogens, forcing physicians to prescribe empirically even with the knowledge of the high negativity rate among cultured specimens. The net result has been a significant increase in emergence of resistant strains, higher treatment costs, and longer recovery cycle due to an increase in side effect risks associated with taking broad spectrum and unnecessary antibiotics.

Broad spectrum antibiotics are commonly prescribed when treating patients that are exhibiting symptoms of sepsis or septic shock. Given the seriousness of these conditions, doctors will often prescribe one or more broad-spectrum antibiotics right away and are not likely to change the treatment regimen until the full effect of the drugs can be assessed or results from microbiology become available. For instance, the document "Surviving Sepsis Campaign Guideline" (SSCG) recommends a treatment protocol in which intravenous antibiotics, consisting of one or more broad-spectrum agents against likely bacterial/fungal pathogens, should be started within the first hour of recognizing severe sepsis and septic shock [R. P. Dellinger et al., Crit. Care Med 2008]. The treatment protocol states that the antimicrobial regimen is to be reassessed daily, and once the pathogen is known, as a matter of good practice, a more appropriate narrow-spectrum antimicrobial drug is to be administered.

Unfortunately, current clinical bacteriology methods typically provide pathogen identification information when it may be too late to impact patient outcomes. This is due to the time lag of 2-3 days from specimen collection to reporting results of pathogen identification and susceptibility testing. Causes for the time lag include the need to transport specimens to clinical laboratories staffed by expert clinical microbiologists and the time required for blood culture and subsequent colony formation after subculturing the specimen on solid culture medium. Although it is recommended to transport the inoculated blood culture bottles to the clinical microbiology laboratory as quickly as possible, preferably within 2 hr, specimens that arrive at the clinical microbiology laboratory after normal business hours are typically held overnight until staff arrives the next day. Blood culture positivity typically takes at least 8-18 hr for bacteria and 1-3 days for fungi. Once specimens are subcultured on solid agar after a positive blood culture has been obtained, an additional at least 8-12 hours for bacteria and 1-4 days for fungi are needed for colonies to form. Plates are examined and appropriate colonies are selected for identification and susceptibility testing. The process further requires analysis and interpretation before reports are released, typically on day 3, which may be too slow to meaningfully impact antibiotic selection and patient outcomes.

While many aspects of clinical microbiology laboratory workflow have been automated, clinical bacteriology remains highly labor-intensive. Many laboratories currently automate identification and susceptibility testing using either the Vitek (BioMerieux) or Phoenix (Becton-Dickenson) instruments. However, these systems, and newer systems based on mass spectroscopy, still depend on selection of appropriate colonies from agar plates by expert personnel.

New technologies are emerging that facilitate the direct rapid identification of pathogens in unprocessed samples, such as direct from whole blood. Such rapid methods typically employ an initial cell lysis step involving reagents that selectively lyse mammalian cells, while attempting to minimally impact the integrity of the microbial cells in the sample.

SUMMARY

Methods and compositions are provided for the selective lysis of eukaryotic cells and the separation of microbial cells. Blood cells and/or other eukaryotic cells in a sample may be selectively lysed by adding, to the sample, a blood lysis reagent including saponin and an alkaline buffer, and optionally sodium polyanethole sulfonate and a non-ionic surfactant, thereby forming a mixture. Microbial cells in the mixture may then be separated, for example, using a separation method such as centrifugation or filtration, and optionally detected or cultured in growth media. Blood lysis reagent compositions are provided that are suitable for preserving the intactness of microbial cells upon mixing with the sample. In example embodiments in which the sample is a blood sample, the blood lysis reagent composition may be selected to avoid or reduce the presence of visible blood debris upon centrifugation or filtration.

Accordingly, in a first aspect, there is provided a method of separating microbial cells from a sample, the method comprising:

mixing a blood sample and a blood lysis reagent, the blood lysis reagent comprising saponin, sodium polyanethole sulfonate and an alkaline buffer, to obtain a mixture having a concentration of saponin between 0.75 and 60 mg/ml, a concentration of sodium polyanethole sulfonate between 0.35 and 50 mg/ml and a pH between 7.8 and 10; and separating microbial cells from the mixture.

In another aspect, there is provided a method of separating microbial cells from a sample, the method comprising:

mixing a sample and a blood lysis reagent, the blood lysis reagent comprising saponin and an alkaline buffer, to obtain a mixture having a pH between 7.8 and 10 and a concentration of saponin suitable for effecting lysis of blood cells within the sample; and separating microbial cells from the mixture.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIGS. 1A-1M schematically illustrate an example method of lysing, separating and concentrating microbial cells within a sample via centrifugation.

FIG. 11B compares the dependence of $\Delta C_T$ on the type of non-ionic detergent in the type 3 blood lysis reagent, after contacting whole blood samples with a type 3 blood lysis reagent containing saponin, SPS, a carbonate-bicarbonate buffer and Triton X-100 or Tween-20, performing centrifugal separation and concentration, heat lysis and real-time RT-PCR.

FIGS. 13A and 13B plot $\Delta C_T$ values for different bacterial species and three different blood lysis reagent pH values (the pH values were measured prior to mixing with whole blood) after contacting spiked phosphate buffer samples with a type 3 blood lysis reagent with different pH value, containing saponin, SPS, a carbonate-bicarbonate buffer and Triton X-100, performing centrifugal separation and concentration, heat lysis and real-time RT-PCR, where FIG. 13A presents data for a Triton X-100 concentration of 0.75% w/v, and FIG. 13B presents data for a Triton X-100 concentration of 0.38% w/v.

FIG. 17A is a table summarizing the performance of blood lysis reagents that include various antifoaming agents.

FIG. 17D is a table comparing the stability of blood lysis reagents without (HR3) and with (HR5) antifoaming agent.

FIGS. 18A and 18B plot the concentration dependence of hemolysis activity of saponin for saponin solutions in different storage buffer, at Day 0 (FIG. 18A) and Day 23 (FIG. 18B) of storage at room temperature after saponin preparation.

FIG. 18C is a table presenting HC50 values (µg/mL) for the hemolysis of sheep red blood cells using saponin solution in different storage buffer, at Day 0 and Day 23 of storage at room temperature after saponin preparation.

FIG. 21C shows the performance of MALDI (VITEK-MS-ID) for the identification of S. aureus, E. coli and P. aeruginosa in the cell suspension after contacting positive blood culture samples with type 3 blood lysis reagents containing different compositions of saponin, SPS, a carbonate-bicarbonate buffer and Triton X-100 followed by two centrifugal washing steps.

FIG. 21O shows the dependence on the number of washing cycles for MALDI (VITEK-MS-ID) identification of K. pneumonia in the cell suspension after contacting positive blood culture samples with a type 3 blood lysis reagent containing saponin, SPS and a carbonate-bicarbonate buffer followed by 1 to 4 centrifugal washing steps.

FIG. 24A shows the recovery of S. aureus from positive blood culture samples, in the context of VITEK-MS-ID (identification by mass spectrometry identification) VITEK2-ID (enzymatic method of identification) and VITEK2-AST (antimicrobial susceptibility testing by micro-dilution method), after contacting 1 mL of positive blood culture samples with a type 3 blood lysis reagent containing saponin, SPS and a carbonate-bicarbonate buffer followed by centrifugal separation and concentration.

FIG. 24B shows the recovery of E. coli from positive blood culture samples, in the context of VITEK-MS-ID, VITEK2-ID and VITEK2-AST, after contacting 1 mL of positive blood culture samples with a type 3 blood lysis reagent containing saponin, SPS and a carbonate-bicarbonate buffer followed by centrifugal separation and concentration.

FIG. 24C shows the recovery of P. aeruginosa from positive blood culture samples, in the context of VITEK-MS-ID, VITEK2-ID and VITEK2-AST, after contacting 1 mL of positive blood culture samples with a type 3 blood lysis reagent containing saponin, SPS and a carbonate-bicarbonate buffer followed by centrifugal separation and concentration.

FIG. 24D shows the recovery of K. pneumoniae from positive blood culture samples, in the context of VITEK-MS-ID, VITEK2-ID and VITEK2-AST, after contacting 1 mL of positive blood culture samples with a type 3 blood lysis reagent containing saponin, SPS and a carbonate-bicarbonate buffer followed by centrifugal separation and concentration.

FIG. 25 is a table summarizing the viable cell recovery of 24 strains (3 strains each of 8 species) of Gram-positive bacteria, 24 strains (3 strains each of 8 species) of Gram-negative bacteria and 12 strains (3 strains each of 4 species) of fungi from whole blood, in the context of VITEK-MS-ID, VITEK2-ID and VITEK2-AST, after contacting 4 mL of whole blood samples with a type 3 blood lysis reagent containing saponin, SPS and a carbonate-bicarbonate buffer, performing centrifugal separation and concentration, and agar plating for colony growth.

FIGS. 26A and 26B schematically illustrate a method of performing convective mixing.

DETAILED DESCRIPTION

Figure 2:
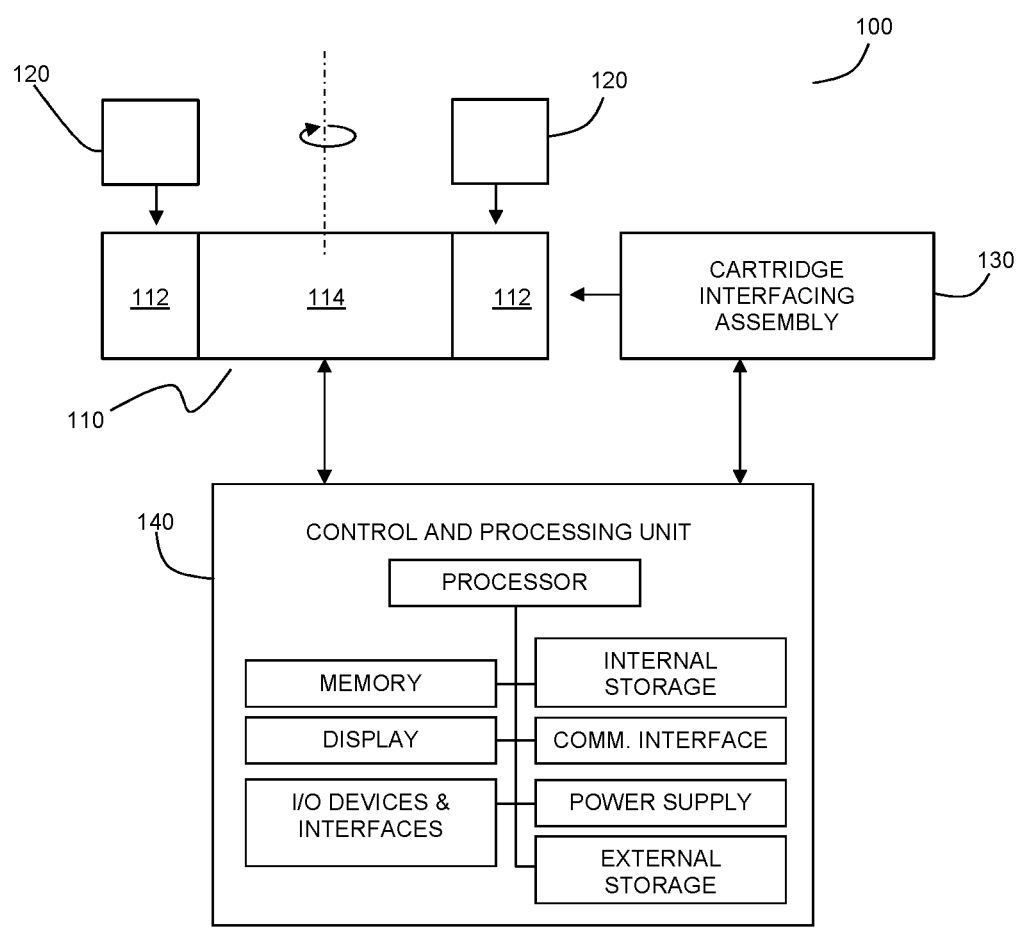
FIG. 2 shows a schematic of an example system for performing automated centrifugation and washing with an integrated fluidic processing cartridge.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprise" and "comprising" are to be construed as being inclusive and open ended, and not exclusive. Specifically, when used in the specification and claims, the terms "comprise" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

Unless defined otherwise, all technical and scientific terms used herein are intended to have the same meaning as commonly understood to one of ordinary skill in the art. Unless otherwise indicated, such as through context, as used herein, the following terms are intended to have the following meanings:

As used herein, the phrase "intact cell" refers to a microbial cell containing nucleic acids, where the microbial cell is separable via a separation method such as, but not limited to, centrifugal separation, filtration, microfluidic separation, or immunomagnetic separation.

As used herein, the phrase "sample" refers to a liquid or suspension that contains, may contain, or is suspected of containing one or more microbial cells. Non-limiting examples of samples include body fluids such as lymph fluid, cerebrospinal fluid, blood (e.g. whole blood, blood culture, and plasma), urine, sputum and saliva. Other examples of samples include homogenized tissue suspensions, including, but not limited to, stool, homogenized suspensions of muscle tissue, brain tissue and liver tissue. A sample may be processed or unprocessed and may optionally include one or more reagents or growth media. In the case of a blood culture sample (a sample containing growth media and whole blood), the blood culture sample may be a blood culture sample having been deemed positive for the presence of microbial cells via a detection modality (e.g. via an automated blood culture system), a mid-culture blood culture sample for which the presence of microbial cells is suspected based on measurements made via one or more mid-culture detection modalities, or mid-culture blood culture sample for which no initial detection results are available.

As used herein, the phrase "blood cells" refers to mammalian cells present in blood, including, but not limited to, red blood cells (erythrocytes), white blood cells (leukocytes) and blood platelets (thrombocytes).

As used herein, the phrase "blood sample" refers to any sample comprising one or more blood cells. Non-limiting examples of blood samples include whole blood samples, blood culture samples, buffy coat samples and platelet samples.

As used herein, the phrase "whole blood" or "whole blood sample" refers to mammalian blood comprising blood plasma and blood cells. "Whole blood" or "a whole blood sample" may include one or more reagents, such as anticoagulation reagents. For example, whole blood may be collected in a sample bottle that may include one or more reagents such as, but not limited to, anticoagulants including SPS (sodium polyanethole sulfonate), EDTA (ethylenediaminetetraacetic acid), sodium citrate and heparin.

As used herein, the phrase "selective lysis" refers to a blood lysis reagent or lysis process whereby the fraction of microbial cells that remain intact following lysis exceeds the fraction of eukaryotic cells that remain intact following lysis, where the eukaryotic cells are associated with the subject from which the sample was collected.

As used herein, the phrase "microbial cell" and "microorganism" comprises bacteria (e.g. gram-positive and gram-negative bacteria, as well as bacterial spores) and unicellular fungi (such as yeast and molds).

As used herein, the phrase "eukaryotic cell" refers to cells originating from an eukaryotic organism excluding fungi, such as animals, in particular animals containing blood, comprising invertebrate animals such as crustaceans and vertebrates. As used herein, "vertebrates" comprise both cold-blooded animals (fish, reptiles, amphibians) and warm-blooded animals (birds and mammals).

As used herein, the phrase "effective buffer concentration", when used with reference to a mixture formed by mixing a volume of a sample with a volume of a blood lysis reagent, where the blood lysis reagent includes a buffer system, refers to the product of the buffer concentration of the blood lysis reagent and a ratio formed by dividing the volume of the blood lysis reagent by the sum of the volume of the blood lysis reagent and the volume of the sample. The effective buffer concentration represents the contribution of the blood lysis reagent to the buffer system in the final mixture (i.e. the dilution factor applied to the buffer concentration of the blood lysis reagent) and may be different than the actual buffer concentration in the final mixture due to buffering components present in the sample.

As used herein, the phrase "separation process" refers to a process suitable for separating and optionally concentrating microbial cells. Non-limiting examples of separation processes include centrifugation, filtration, immunomagnetic separation and microfluidic separation.

Conventionally, whole blood samples that are suspected of containing microbial cells are initially cultured in the presence of growth media in order to obtain a high concentration of cells, which are then subcultured on agar plates to support the growth of individual colonies. Microbial cells from the colonies are then employed for subsequent assays. Unfortunately, such growth-based methods require time delays of many hours or days in order to achieve sufficient microbial growth to support subsequent assays.

Recently, efforts have been made to detect microbial cells directly from whole blood in the absence of blood culture, without requiring a growth step. The direct identification of microbial cells from whole blood samples typically requires microbial cell separation and concentration prior to performing a subsequent identification assay. For example, an improved method for microbial cell separation and concentration that is suitable for use in direct identification of microbial cells from whole blood was disclosed in U.S. Pat. No. 9,707,555, titled "Method for Pretreatment of Microbial Samples" and in International Patent Publication No. PCT/CA2013/000992, titled "Apparatus and Method for the Extraction of Microbial Cells", both of which are hereby incorporated by reference in their entirety.

According to the method disclosed in International Patent Publication No. PCT/CA2013/000992, a blood-based sample, such as whole blood or cultured blood, is combined with a blood lysis reagent (BLR) and subjected to centrifugation. The blood lysis reagent lyses and digests blood cells such that the residual blood debris does not significantly sediment during centrifugation, while leaving the microbial cells intact and suitable for centrifugal separation. FIGS. 1A-1M illustrate an example implementation of a pretreatment device and method according to one embodiment of the teachings of International Patent Publication No. PCT/CA2013/000992, in which a cushioning liquid is employed, and these teachings are briefly summarized below.

Referring to FIG. 1A, according to the teachings of International Patent Publication No. PCT/CA2013/000992, the pretreatment vessel 20 is provided containing a volume of blood lysis reagent 22 and volume of cushioning liquid 21. The pretreatment vessel 20 is a vessel suitable for centrifugation, such as a microcentrifuge tube. The cushioning liquid 21 is a high-density and water-immiscible liquid that serves to form a liquid surface 32 onto which the microorganisms settle during centrifugation. As shown in FIG. 1A, the cushioning liquid 21 has a density such that it settles at the bottom of pretreatment vessel 20 under the influence of gravity. It will be understood that the term "high density", as used herein with regard to the cushioning liquid 21, refers to a density that is sufficiently high such that the target microbial cells will not substantially penetrate the cushioning liquid under the prevailing centrifugal force. The density of the cushioning liquid 21 is therefore chosen to be greater than that of both the microbial cells and the other liquids. The cushioning liquid is also immiscible in the other liquids including, but not limited to, whole blood, blood culture media mixed with whole blood, blood lysis reagent 22, and a wash liquid (as described below) such that it remains a distinct liquid phase throughout the pretreatment process.

FIG. 1B illustrates the addition of a volume of blood sample 26 to the pretreatment vessel 20, where mixing of the blood lysis reagent 22 with the blood sample 26 forms a mixture 30 (shown in FIG. 1C). After providing a sample to the pretreatment vessel 20 (e.g. through pierceable rubber stopper 25), the pretreatment vessel may be agitated to produce further mixing of the sample with the blood lysis reagent 22 (as shown in FIG. 1C). After forming the mixture 30 and agitating the pretreatment vessel 20, the pretreatment vessel 20 is centrifuged, as illustrated in FIG. 1D. The pretreatment vessel 20 is centrifuged at a suitable rate and for a suitable time to cause the microbial cells in the mixture 30 to pass out of the suspension and collect at an interface 32 between the cushioning liquid 21 and the supernatant 33 as shown in FIG. 1D. As taught in International Patent Publication No. PCT/CA2013/000992, fluorinated hydrocarbons, having molecular weight ranging from about 300 to 850, are suitable as cushioning liquids. Examples are FC-40, FC-43, FC-70, and FC-77, and the cushioning liquid volume should be sufficiently large to provide an adequately large sedimentation surface so that all target precipitate is collected on its surface.

After centrifugation, the pretreatment vessel 20 may be re-oriented in a position suitable for subsequent aspiration and dispensing operations, such as, for example, a vertical orientation as shown in FIG. 1E, such that the cushioning liquid 21 moves to the bottom of the pretreatment vessel 20 and remains there due to gravity. The prevention of the resuspension of cells enables the removal of most of the supernatant, as shown in FIG. 1F, such that only a small volume of residual supernatant is left behind containing the retained microbial cells.

As shown in FIGS. 1G-1K, one or more washing cycles may then optionally be performed to purify the supernatant and to reduce the concentration of blood cell debris and blood lysis reagent present in the pretreated sample. Referring to FIG. 1G, a volume of the washing liquid 35 may be added to the sample pretreatment vessel 20. After addition of the washing liquid 35, the solution is mixed to resuspend debris that may have sedimented or adsorbed to the vessel wall during centrifugation. This may be accomplished by vortexing as shown in FIG. 1H. The pretreatment vessel 20 is subsequently centrifuged and re-oriented, and a substantial portion of the supernatant is removed, as shown in FIGS. 1I-1K, in a manner similar to that described for FIGS. 1D-1F.

After performing the (optional) washing cycles, the pretreatment vessel 20 may be agitated as shown in FIG. 1L, such that the retained microbial cells are resuspended in the residual supernatant 37. For example, the pretreatment vessel 20 may be vortexed for approximately 5 to 20 seconds at a low speed, as described above. After agitation, the cushioning liquid 21 is allowed to settle at the bottom of the pretreatment vessel 20, as shown in FIG. 1M, such that pretreatment vessel 20 includes a residual suspension of the retained microbial cells above the cushioning liquid 21. This residual suspension may then be removed to obtain the extracted sample, referred to as the pretreated sample 38.

An example automated system for performing microbial cell separation and concentration, based on the methods of International Patent Application No. PCT/CA2013/000992, is taught in International Patent Application No. PCT/CA2015/050449, titled "Apparatus, System and Method for Performing Automated Centrifugal Separation", which is hereby incorporated by reference in its entirety. FIG. 2 provides an illustration of the example integrated system 100 for performing automated centrifugal separation (and/or washing). The example system 100 includes a centrifuge 110, which receives one or more integrated fluidic processing cartridges 120 for centrifugal separation. The centrifuge 110 includes one or more receptacles 112 which are connected to a motorized rotor 114 and are configured to receive integrated fluidic processing cartridges 120. The cartridge receptacles 112 may be, for example, of the fixed angle type or the swinging bucket type which are common in laboratory centrifuges (e.g. each receptacle 112 may be pivotally connected to the motorized rotor 114).

The cartridge interface assembly (unit) 130 is configured to removably engage (or interface) with an integrated fluidic processing cartridge 120 when the motorized rotor 114 is at rest, for controlling the flow of fluids within integrated fluidic processing cartridge 120. The interfacing of the cartridge interfacing assembly 130 with the integrated fluidic cartridge may occur, for example, via a direct interface between the cartridge interfacing assembly and the integrated fluidic cartridge 120, or, for example, via an interface (e.g. an actuation interface) on the centrifuge 110 (e.g. on the motorized rotor 114 or cartridge receptacle 112). The centrifuge 110 and the cartridge interfacing assembly 130 are controlled via control and processing unit 140.

Figure 3A:
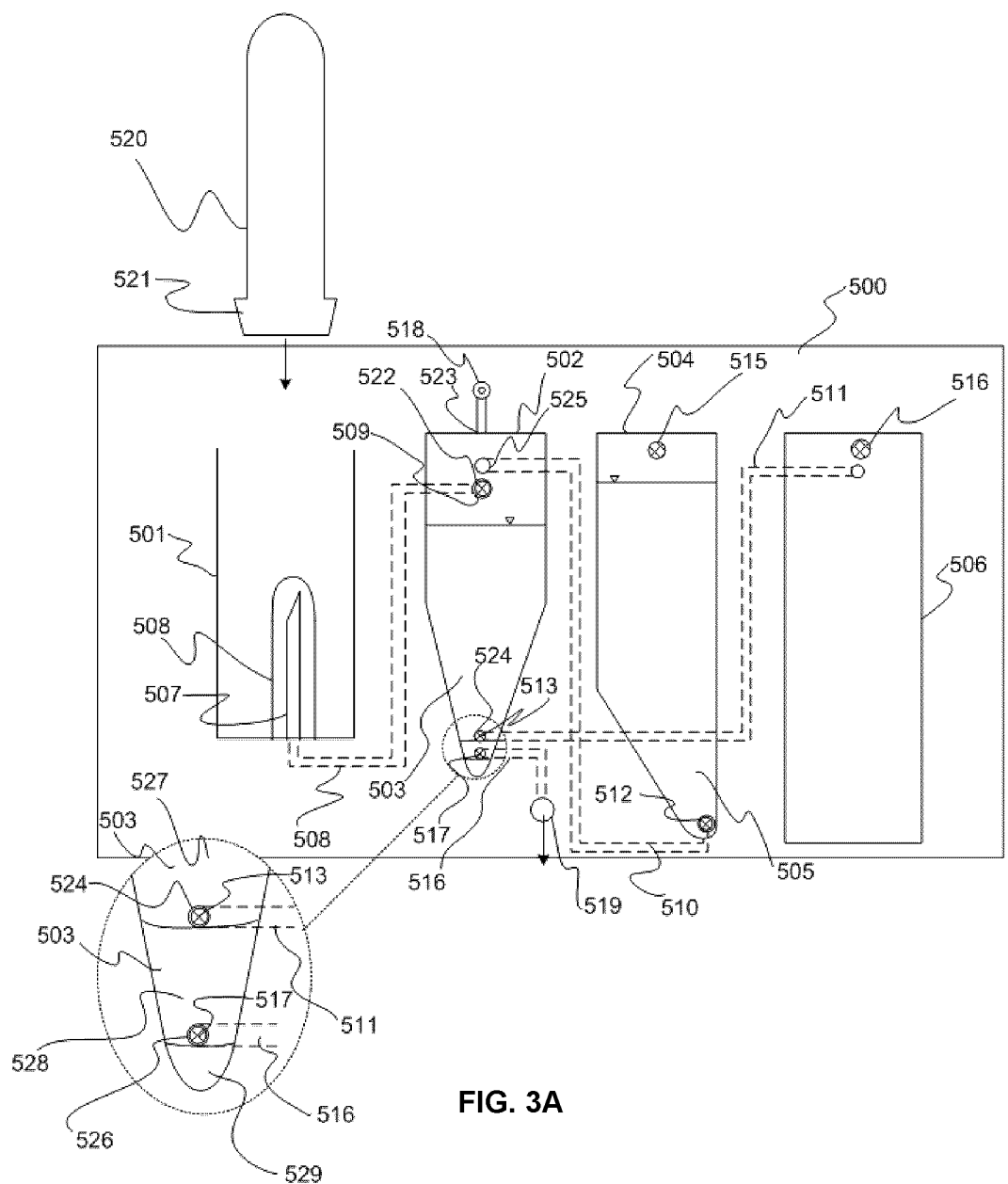
FIGS. 3A to 3C illustrate an example integrated fluidic processing cartridge configured for extraction of a sample directly from a collection tube, and subsequent centrifugation and washing, to obtain a concentrated and purified suspension of microbial cells.

According to the teachings of International Patent Application No. PCT/CA2015/050449, and with reference to the example schematic representation in FIG. 3A, an example integrated fluidic processing cartridge 500 is portrayed which incorporates elements suitable for automated separation and washing of microbial cells from whole blood to obtain a concentrated suspension. The example integrated fluidic processing cartridge includes a sample transfer receptacle 501, a macrofluidic centrifugation chamber 502, a diluent chamber 504 and a supernatant chamber 506. Diluent chamber 504 is prefilled with a wash buffer fluid 505, is fluidically connected to macrofluidic centrifugation chamber 502 via conduit 510 equipped with shutoff valve 512, contains a vent to atmosphere 515 and is otherwise closed. The supernatant chamber 506 is fluidically connected to macrofluidic centrifugation chamber 502 via a conduit 511 equipped with shutoff valve 513, and contains a vent to atmosphere 516, where the supernatant chamber 506 is otherwise closed. The macrofluidic centrifugation chamber 502 has a conical or round bottom shape and a smooth inner surface which minimizes adsorption or trapping of microbial cells during centrifugation and is closed with the exception of the openings 522, 523, 524, 525, 526 to respective conduits. In the present example embodiment, the macrofluidic centrifugation chamber is employed for the processing of blood-containing samples (e.g. whole blood, blood culture samples, or other blood-containing samples), and contains a blood lysis reagent 503 and a cushioning fluid 529 to aid in microbial cell recovery and to minimize compaction injury of the cells which may compromise the integrity and recovery of the target nucleic acids.

The sample transfer receptacle is equipped with a needle 507 which is mounted at the bottom of the receptacle. The needle is connected to a fluid path 508 equipped with a shut-off valve 509 which leads to macrofluidic centrifugation chamber 502. A sample tube or container 520 with a pierceable cap 521, such as, for example a Vacutainer® blood collection tube or a blood culture tube containing a blood sample and growth media, may be inserted into the sample transfer receptacle such that the needle 507 pierces the cap 521 thus allowing transfer of a sample fluid to the cartridge via the needle and fluidic path 508. Optionally, the needle 507 is covered with a pierceable hood 508 which protects the needle from contamination.

The example integrated fluidic processing cartridge 500 taught by International Patent Application No. PCT/CA2015/050449 is a closed cartridge (apart from the vents described below) which, following the insertion of the sample, performs all the functions required for separation and washing of a concentrated suspension within the chambers and conduits of the cartridge, has all reagents and solutions stored in chambers on the cartridge, and retains all excess liquids including waste supernatant in chambers on the cartridge. One or more of the vents and ports may be protected by air permeable membranes with a pore size sufficiently small to prevent the ingress of microbial pathogens in the target range of the device. According to the present example embodiment, all excess and waste liquids are stored on the cartridge and are not exposed to the user. Thus, the closed cartridge provides a device which protect the user from direct contact with the sample and for which the sample is not susceptible to contamination by external factors during the separation and washing process.

Figure 4:
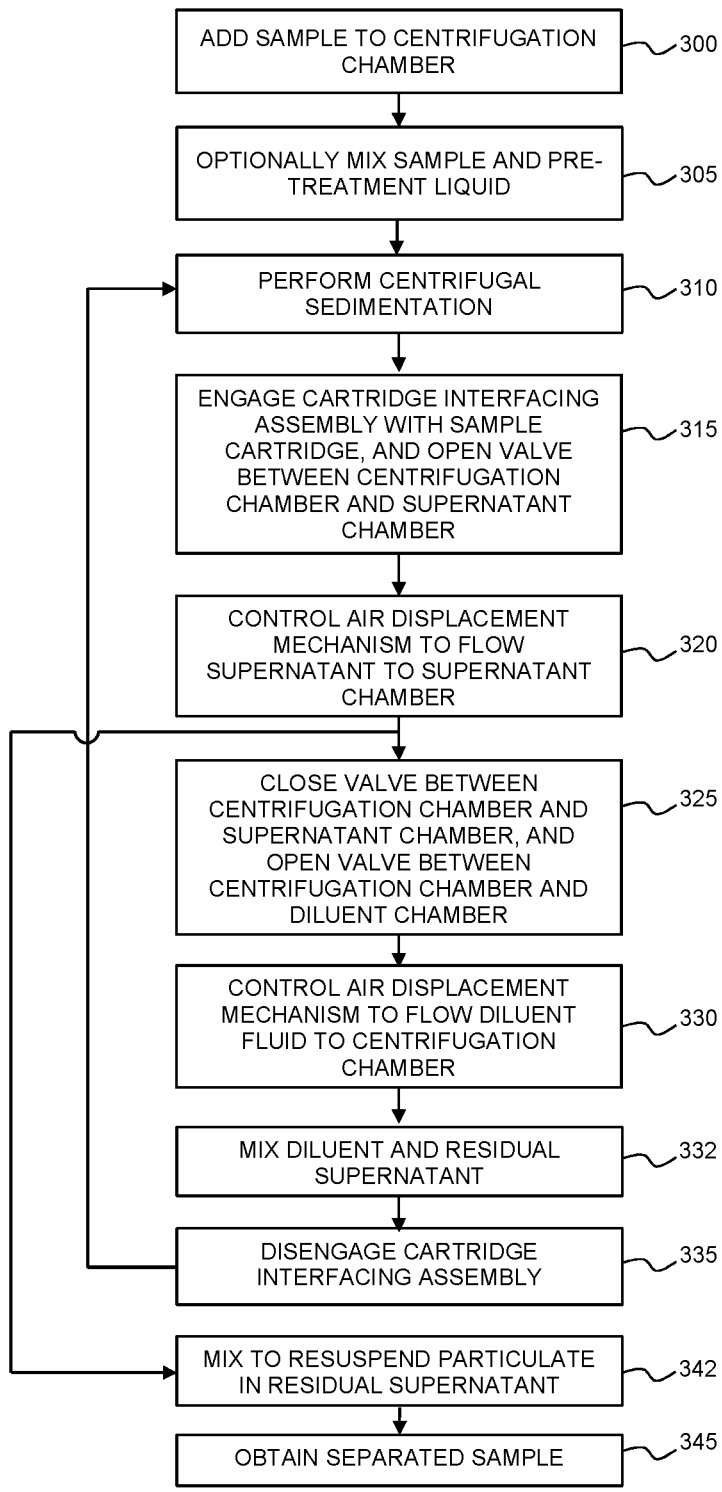
FIG. 4 provides a flow chart illustrating an example method for performing automated centrifugation and washing.

As taught by International Patent Application No. PCT/CA2015/050449, an automated separation and washing process is generally described in FIG. 4, with reference to the example integrated fluidic processing cartridge 500 shown in FIG. 3A. A cartridge interfacing assembly, described in detail in International Patent Application No. PCT/CA2015/050449, is equipped with all the components required to perform the necessary actions including actuation of the cartridge valves 509, 512, 513, and 517 and an air displacement device capable of application of both positive and negative gauge pressure to the cartridge centrifuge chamber via cartridge port 518.

The sample tube 520 containing a sample is inserted into the sample transfer receptacle 501 of cartridge 500 thus piercing the tube cap 521 to perform the sample transfer to the macrofluidic centrifugation chamber as shown at 300 of FIG. 4. The cartridge interface assembly engages with the cartridge via a cartridge receptacle, described in detail below, and is actuated such that valve 509 is open and valves 512, 513 and 517 are closed, thus sealing all fluid paths emanating from macrofluidic centrifugation chamber except the path 508 from the sample tube.

An air displacement device is engaged with the port 518 by way of a connector which provides a sealed connection with the port. Optionally, a rigid or flexible tube connects the air displacement device to the connector. Sample transfer to macrofluidic centrifugation chamber 502 is performed by operating the air displacement device to extract air from macrofluidic centrifugation chamber to cause sample flow from the sample tube 520 into macrofluidic centrifugation chamber 502 via fluid path 508. The entry 523 of the port 518 must be positioned above the fluid level and with a sufficient air gap between the fluid level and the entry 523 such that no fluid flows into entry 523 to the port 518. The air displacement activated flow is done in a controlled manner such that a predetermined volume of sample is transferred into macrofluidic centrifugation chamber.

According to one embodiment of the teachings of International Patent Application No. PCT/CA2015/050449, the entry 522 to flow path 508 is also in the air gap above the fluid level such that, following transfer of the desired volume of sample, the air displacement via port 518 can be reversed to provide a small amount of air displacement into macrofluidic centrifugation chamber to clear the flow path 508 of sample fluid and move this residual sample back into the sample tube 520. Then the valve 509 is closed and the sample tube 520 is optionally removed from the receptacle 501.

The blood lysis reagent 503 may be present in the centrifugation chamber 502 prior to the sample transfer process or alternatively it may be transferred from a blood lysis reagent tube in a similar manner as the sample. Alternatively, a blood lysis reagent storage chamber may be provided on the cartridge and a fluidic path with valve and an air vent may be provided to allow the blood lysis reagent 503 to be moved to macrofluidic centrifugation chamber in a similar manner to the movement of wash buffer to macrofluidic centrifugation chamber as described below.

As taught in International Patent Application No. PCT/CA2015/050449, after addition of the sample to macrofluidic centrifugation chamber 502, the sample and the blood lysis reagent 503 may optionally be mixed as shown at 305 in FIG. 4. A mixing mechanism may be provided whereby the instrument performs vortexing, shaking, or cyclic inversion of the cartridge. This operation is performed with valves closed on all fluid paths emanating from macrofluidic centrifugation chamber 502. A valve may be provided on the fluid path to the port 518 to prevent fluid from entering the air path during mixing. In addition, or alternatively, an air permeable membrane which prevents the passage of fluid may be placed in the air path between macrofluidic centrifugation chamber and the port 518 to prevent fluid from reaching the port 518. This membrane may also be configured to serve as an air filter to prevent the ingress of microbes from the environment or from the air displacement device. Alternatively, the path between the port 518 and the entry opening 523 to the macrofluidic centrifugation chamber can be designed to possess high fluidic resistance such that under the prevailing conditions fluid will be prevented from entering the opening 523 or will be prevented from proceeding all the way to the port 518. Likewise vents 515 and 516 in diluent chamber 505 and supernatant chamber 506 respectively may be equipped with an air permeable membrane and/or a path with high fluidic resistance to serve a similar purpose.

Following the mixing step 305, a centrifugal sedimentation step 310 is performed whereby the cartridge interfacing assembly is disengaged from the motorized rotor 114 and the cartridge 120 is centrifuged such that the microbial cells in the macrofluidic centrifugation chamber sediment on the cushioning liquid, for example, as per the methods of PCT Patent Application No. PCT/CA2013/000992, as described above. The centrifuge may be, for example, an angle centrifuge or a hanging bucket centrifuge and the centrifugal parameters may be selected, for example, according to the conditions provided in PCT Patent Application No. PCT/CA2013/000992.

The relative centrifugal force applied to the fluids within the macrofluidic centrifugation vessel may be, for example, within the range of 1000-15,000 g, or for example, 2,000-12,000 g, or, for example, 3000-10,000 g, or, for example, 3000-7,000 g, or, for example, 5000-10,000 g, or, for example, 4000-8,000 g. In applications involving separation of bacterial and fungal cells from biological samples, it has been found that a suitable relative centrifugal force (RCF) is within the range of 1000 g-15000 g range, and more specifically, within the range of 3000 g-7000 g.

Following the centrifugal sedimentation step 310 of FIG. 4, the centrifuge rotor is stopped and the cartridge interfacing assembly is re-engaged with the motorized rotor as shown at 315 and extraction of the supernatant 527 from macrofluidic centrifugation chamber 502 to the supernatant chamber 506 is performed as shown at 320, whereby the residual 528 (containing the microbial cells) is retained at the bottom of macrofluidic centrifugation chamber 502. This action is performed by opening valve 513 while valves 509, 512 and 517 remain closed and engaging the air displacement device connector with port 518 and controllably displacing air into macrofluidic centrifugation chamber. Thus, air displacement induced flow of the supernatant occurs through fluid path 511, the entry 524 of which is placed below the lowest extent of the supernatant. Optionally the entry 524 is placed at the lowest extent of the supernatant which is to be expressed from macrofluidic centrifugation chamber, thus preventing residual 528 from being extracted from macrofluidic centrifugation chamber.

Following the supernatant extraction step 320, the wash buffer dispensing steps 325 and 330 are performed whereby wash buffer is dispensed into macrofluidic centrifugation chamber 502. This action is performed by opening valve 512 while holding valves 509, 513 and 517 closed and engaging the air displacement device connector with port 518 and controllably evacuating air from macrofluidic centrifugation chamber 502. Thus air displacement induced flow of the wash buffer occurs through fluid path 510. The entry 525 of wash buffer path 510 is preferably placed above the highest extent of the fluid level in macrofluidic centrifugation chamber.

Following the wash buffer dispensing step 544, the mixing step 332 is performed to thoroughly mix the wash buffer and the residual fluid in macrofluidic centrifugation chamber. This may be performed by vortexing, shaking, or cyclic inversion of the cartridge as described previously. Following the mixing step 332, the centrifugal sedimentation step 310 is performed to re-sediment the collected microbial cells and the supernatant is removed from the centrifugal chamber as in step 320. The sequence of steps 325-335 and 310-320 collectively form a wash cycle, whereby the cell suspension is diluted in wash buffer, the microbial cells are re-sedimented, and the supernatant is extracted. The wash cycle may be repeated multiple times to effect multiple additional wash cycles as required to obtain a final microbial cell suspension that is sufficiently dilute of contaminants and interferants.

As taught in International Patent Application No. PCT/CA2015/050449, the desired dilution factor depends on the sample composition and downstream detection procedure. In one embodiment, intended for applications involving separation of bacterial and fungal cells from biological samples, electrical lysis of microbial cells and detection through reverse transcription real-time polymerase chain reaction (reverse transcription RT-PCR) amplification of ribosomal RNA, the dilution factor is selected in the range of 100-100000, where a more preferred range is 1000-50000. In another embodiment involving separation of bacterial and fungal cells from blood samples, lysis of microbial cells and detection through PCR amplification of DNA, the dilution factor can be as small as 1 provided that inhibitor-resistant polymerase enzyme along with an appropriate amplicon detection scheme is employed. Exemplary implementation of DNA amplification and detection method in whole blood is reported in prior art (e.g., L. A. Neely et al., *Science translational medicine* 5.182 (2013): 182ra54-182ra54.).

Following the final supernatant extraction step 320, the mixing step 342 is performed to resuspend the sedimented microbial cells in the final residual fluid 528 to produce the final suspension. Following the resuspension step 342, the final suspension is extracted by air displacement through fluid path 510. The volume of the final suspension depends on the nature of the application. For instance, when the intended application is the detection of microbial cells in whole or cultured blood, the volume of the final cell suspension may be selected to be in 10 μL-500 μL range, while a more preferred range is 20 μL-120 μL, or 50-100 μL. During the extraction of the final cell suspension valve 517 is open and valves 509, 512 and 513 are closed and air is displaced through port 518 into macrofluidic centrifugation chamber to displace the fluid out of opening 526 via fluid path 516. The opening 526 is so positioned at the top surface of the cushioning fluid 529 that the final suspension in its entirety, or substantially all of the suspension, is expressed from macrofluidic centrifugation chamber without expressing any of the cushioning fluid 529 as depicted in FIG. 3A. Alternatively, the opening 526 is so positioned that the final suspension and a portion of, or all of, the cushioning fluid may be expressed from the macrofluidic centrifugation chamber through fluid path 516. The fluid path 516 leads to the next downstream cartridge element which in some embodiments may be a chamber or chamber configured to allow retrieval of the final suspension from the cartridge for further processing outside of the cartridge, and in other embodiments this may be a fluid path to a suspension collection chamber, or for example, an electrical lysis chamber as described below.

Figure 3B:
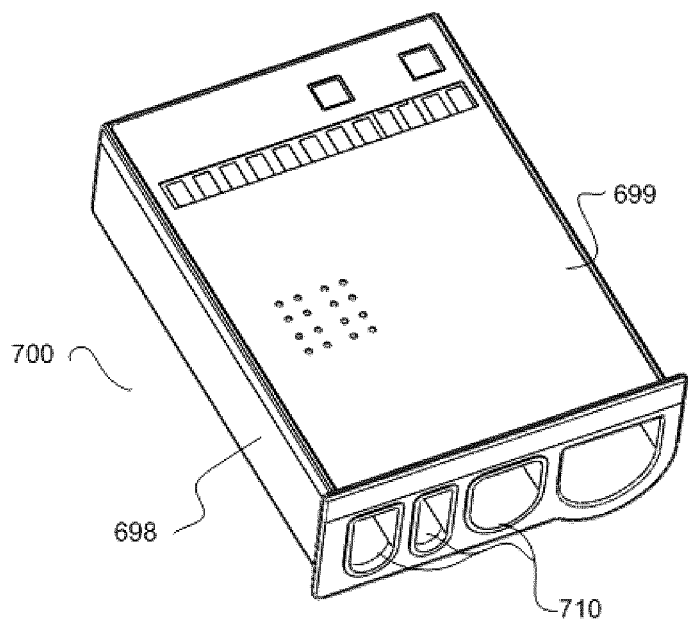
Figure 3C:
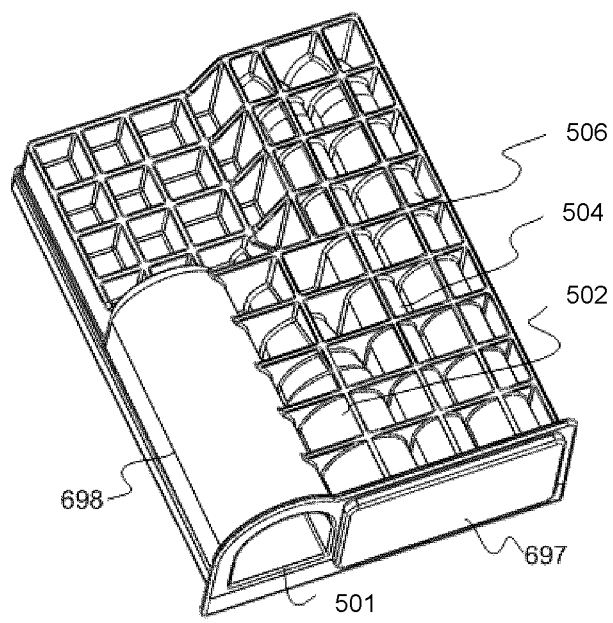

FIGS. 3B and 3C illustrate an example integrated cartridge for performing automated sample preparation and optionally performing one or more additional subsequent processing steps (such as assays) in a closed system, as disclosed in International Patent Application No. PCT/CA2015/050449. The example integrated cartridge 700 is shown having three components, the first component 698 including the sample transfer receptacle 501, macrofluidic centrifugation chamber 502, the diluent chamber 504 and supernatant chamber 506. The first component 698 may be a single plastic molded part fabricated from materials which are compatible with the form and function of the device. Alternatively, the first component 698 may be an assembly of subcomponents which are plastic parts, molded or formed by a means consistent with the material, form and function of the device. In this respect, the material should be selected to be of sufficiently high strength to withstand the high centrifugal forces that the cartridge will be subjected to, and the materials should be compatible with the fluids used and, in the case of molecular applications, should not introduce contaminants into the pretreated cell suspension which will interfere with downstream process. Non-limiting examples of materials from which first component 698 can be fabricated are polypropylene, polycarbonate, polyethylene, PET, polystyrene, Cyclic Olefin Copolymer or some variant of these materials.

The second component 699 is a microfluidic device mounted on the lateral face of component 698 comprises fluidic paths and valves connecting the chambers in component 698 and optionally included components for additional fluidic processing, such as, but not limited to, electrical lysis, reverse transcription and PCR (RT-PCR). The second component 699 is a laminate composed of a number of layers in which are formed holes, channels and chambers.

The layers may be machined, punched, embossed or molded to form the necessary features. Each layer may be comprised of either a single or multiple sublayers each of either different materials or the same materials listed previously based on the function of said sublayer laminated by either adhesives bonding, thermal bonding, ultrasonic bonding, or other methods known to those skilled in the art. The layers and sublayers presented are grouped solely for the purpose of ease of understanding the embodiment being discussed. In the present example implementation involving molecular processing, the materials should be compatible with the fluids and in cases in which molecular amplification is to be performed, the materials should not introduce substances inhibitory to such amplification (e.g. RT-PCR) or which interfere with detection of target microbes, and should not be contaminated with non-target analyte (e.g. non-target microbial cells) or nucleic acids. The materials should also not adsorb target molecules, reactants, and reagent components to an extent which will interfere with the process. Example plastic materials and plastic film materials include, but are not limited to, polycarbonate, polypropylene, PET, and cyclic olefins.

The chamber openings 710 (shown in FIG. 3B) may be sealed with a membrane seal, a foil seal or a cap 697 (shown in FIG. 3C) following dispensing of the wash buffer and pretreatment fluid into the diluent chamber and macrofluidic centrifugation chamber respectively. The seals or caps may be bonded using methods and materials compatible with heat sealing, adhesive bonding, ultrasonic bonding. Alternatively, the chambers may be sealed prior to dispensing of these liquids and alternate ports may be provided for the purpose of dispensing these liquids and these ports may be sealed following the dispense operation. The cap 697 may be molded, embossed, machined or rapid prototyped, and may be constructed from polycarbonate, polystyrene, PET, polyester or other material appropriate to its form and function.

International Patent Application No. PCT/CA2013/000992 discloses a number of different blood lysis reagent compositions that may be employed for the digestion of blood components prior to centrifugation. As noted above, the presence of the blood lysis reagent causes the selective lysis of blood cells. In one example implementation taught by International Patent Application No. PCT/CA2013/000992, the blood lysis reagent may be an aqueous liquid including saponin and sodium polyanetholesulfonate (a sodium salt of polyanetholesulfonic acid, known as SPS), and a blood lysis reagent having such a composition is henceforth referred to as a type 1 blood lysis reagent. The blood lysis reagent may also include an antifoaming agent, such as poly (propylene glycol) (PPG, e.g. with a molecular weight of approximately 2000). International Patent Application No. PCT/CA2013/000992 teaches example concentration ranges of saponin and SPS for a type 1 blood lysis reagent, upon mixing whole blood and the blood lysis reagent, of approximately 1.5 to 80 mg/mL and 0.5 to 20 mg/mL, respectively.

As taught in International Patent Application No. PCT/CA2013/000992, SPS is an anti-coagulant and anti-phagocytosis agent and is known to inhibit antimicrobial agents (Sullivan, N. M., Sutter, V. L., & Finegold, S. M. (1975). Practical aerobic membrane filtration blood culture technique: development of procedure. Journal of clinical microbiology, 1(1), 30-36). The mechanism by which SPS assists in blood cell lysis is not well understood. Without intended to be limited by theory, it is believed that SPS may offer some level of protection to the microorganisms during blood cell lysis, reduce the incidence of entrapment of bacteria in cell debris, and/or reduce the amount of coagulated components which may otherwise be present in the sediment.

In another example implementation of a blood lysis reagent composition taught by International Patent Application No. PCT/CA2013/000992, a blood lysis reagent may be an aqueous liquid including Triton X-100 and SPS in a buffer having a pH ranging from 9 to 11, and a blood lysis reagent having such a composition is henceforth referred to as a type 2 blood lysis reagent. The blood lysis reagent may also include an antifoaming agent, such as poly (propylene glycol) (PPG, e.g. with a molecular weight of approximately 2000). International Patent Application No. PCT/CA2013/000992 teaches example concentration ranges of Triton X-100 and SPS for a type 2 blood lysis reagent, upon mixing whole blood and the blood lysis reagent, of approximately 0.5 to 1.5% w/v and 5 to 10 mg/mL, respectively.

As noted above, the type 1 blood lysis reagent composition described above was found to be suitable for manual and semi-automated separation and concentration of microbial cells from whole blood as per the teachings of International Patent Application No. PCT/CA2013/000992. However, when adapting the reagent formulations disclosed in International Patent Application No. PCT/CA2013/000992 to the automated separation and concentration, and subsequent identification, of microbial cells from whole blood as per the automated methods of International Patent Application No. PCT/CA2015/050449, the present inventors found that the type 1 blood lysis reagent composition was most suitable for cases in which the quantity of whole blood was less approximately 1 ml.

Figure 5A:
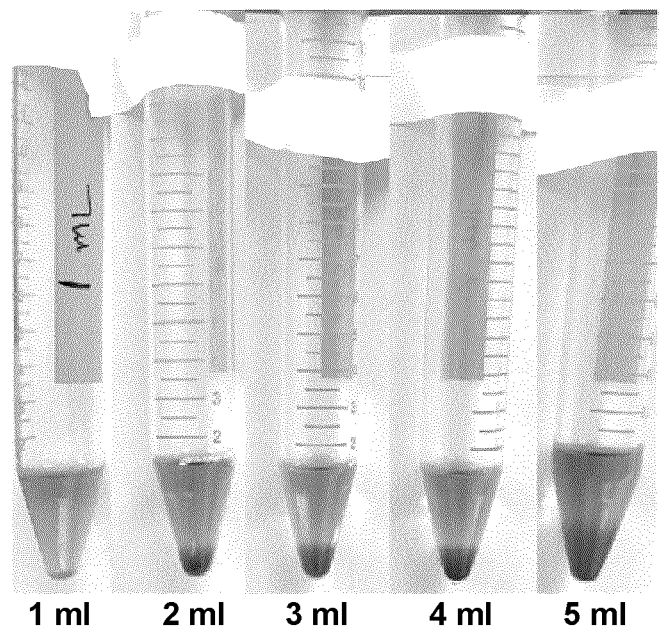
FIG. 5A shows images of centrifuge tubes after performing hemolysis of whole blood samples with different volumes using an equal volume of type 1 blood lysis reagent containing saponin and sodium polyanethole sulfonate (SPS), followed by two centrifugal washes.

This is demonstrated in FIG. 5A, which shows post-centrifugation images of centrifuge tubes after performing hemolysis of different volumes of whole blood samples using a type 1 blood lysis reagent. Whole blood samples were collected in vacutainers with SPS anticoagulant and 1 ml to 5 ml aliquots of whole blood were distributed in respective 15 mL centrifuge tubes. Whole blood samples were mixed with various volumes of type 1 blood lysis reagents, such that upon mixing, the concentration of saponin and SPS were 37.5 mg/mL and 7.5 mg/mL, respectively, irrespective of blood volume. The resulting mixture was subjected to 2 wash cycles. Although sufficient hemolysis of 1 ml of whole blood was observed, insufficient hemolysis was observed in the case of the higher sample volumes. For example, during hemolysis of 3 ml of whole blood, blood debris sedimented and wash cycles were not able to increase the sample purity. As shown in FIG. 5A, significant residual blood debris is present after centrifugation for whole blood volumes exceeding 1 ml. The insufficient digestion of the blood debris is evident by the dark residue that is visible in the lower region of the centrifuge tube, which is seen to increase with increasing whole blood volume. Such residue can complicate the automation of sample preparation steps, as the blood debris forms a cake upon centrifugation or filtration.

The present inventors found that in order to facilitate the automated processing of larger volumes of whole blood without generating significant debris, a blood lysis reagent having a type 2 blood lysis reagent composition could be employed. This is demonstrated in FIG. 5B, which shows post-centrifugation images of centrifuge tubes after performing hemolysis of different volumes of whole blood samples using a type 2 blood lysis reagent. Whole blood samples of 1 ml to 5 ml were mixed with various volumes of type 2 blood lysis reagents containing TritonX-100, SPS and a carbonate-bicarbonate buffer. The reagent solutions were prepared by combining 10 ml of a carbonate-bicarbonate buffer solution prepared with a buffer concentration of 200 mM and a pH of 10, with 10 ml of a solution having a concentration of 30 mg/ml of SPS and 3% w/v of Triton X-100 to obtain reagent solutions having a volume of 20 ml, an SPS concentration of 15 mg/ml, a Triton X-100 concentration of 1.5% w/v, a buffer concentration of 100 mM, and a pH of 9.9.

Figure 5B:
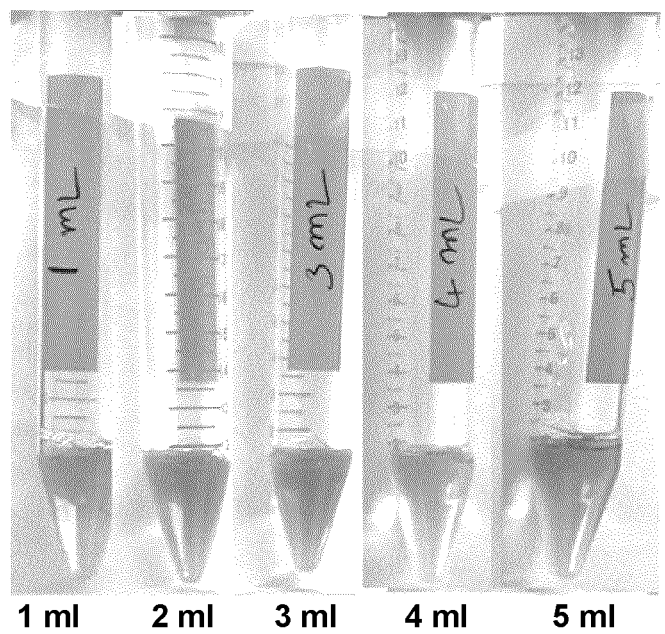
FIG. 5B shows images of centrifuge tubes after performing hemolysis of whole blood samples with different volumes using an equal volume of type 2 blood lysis reagent containing Triton X-100, SPS, and a carbonate-bicarbonate buffer, followed by two centrifugal washes.

After mixing the whole blood samples with equal respective volumes of reagent solutions, the concentration of SPS was 7.5 mg/ml, the concentration of Triton X-100 was 0.75% w/v, the pH was 9.1 irrespective of blood volumes and the effective buffer concentrations was 50 mM irrespective of blood volumes. The resulting mixture was subjected to 2 wash cycles. As shown in FIG. 5B, no residual blood debris is visible for any of the whole blood volumes. The significantly improved digestion provided by the type 2 blood lysis reagent is believed to be due to the high pH environment.

Despite the success of the type 2 blood lysis reagent in performing digestion of blood components while avoiding significant post-centrifugation debris, the present inventors discovered that while the type 2 blood lysis reagent is suitable for the separation and concentration of many types of microbial cells, the use of type 2 blood lysis reagent was found to result in the loss of signal when performing real-time reverse transcription polymerase chain reaction (real-time RT-PCR) after centrifugal processing for some microbial cell species. For example, the present inventors found that when a type 2 blood lysis reagent is employed for the processing of whole blood samples containing *Pseudomonas aeruginosa* and *Proteus mirabilis*, the blood lysis reagent appears to affect the intactness of the microbial cells, leading to a loss of rRNA during centrifugal processing, and resulting in an increased required number of cycles during real-time RT-PCR detection.

The present inventors experimentally investigated the effect of the type 2 blood lysis reagent on cell intactness as follows. Experiments were performed by contacting spiked whole blood samples with a volume of 3 ml containing *Pseudomonas aeruginosa* (PA), *Proteus mirabilis* (PM), and *Staphylococcus aureus* (SA), prepared according to Example 2 below, with a type 2 blood lysis reagent. The reagent solutions were prepared by combining 10 ml of a carbonate-bicarbonate buffer solution prepared with a buffer concentration of 200 mM and a pH of 10, with 10 ml of a solution having a concentration of 40 mg/ml of SPS and 3% w/v of Triton X-100 to obtain reagent solutions having a volume of 20 ml, an SPS concentration of 20 mg/ml, a Triton X-100 concentration of 1.5% w/v, a buffer concentration of 100 mM, and a pH of 9.9. After mixing 5 mL of the reagent with 3 mL of whole blood samples, the concentration of SPS was 12.5 mg/ml, the concentration of Triton X-100 was 0.94% w/v, the pH was 9.1 and the effective buffer concentrations was 62.5 mM. Spiked phosphate buffer samples were prepared according to the method of Example 3. Sample pretreatment and real time RT-PCR was performed according to the methods provided in Examples 6 and 7 below for spiked phosphate buffer samples for spiked controls and spiked whole blood samples, respectively. The threshold cycle value (CT value; i.e. the number of the PCR cycle after which the assay signal increases above a noise threshold value) was measured, and the difference in CT values, $\Delta C_T$, was determined based on the difference between the spiked whole blood CT value and the spiked control CT value.

Figure 6:
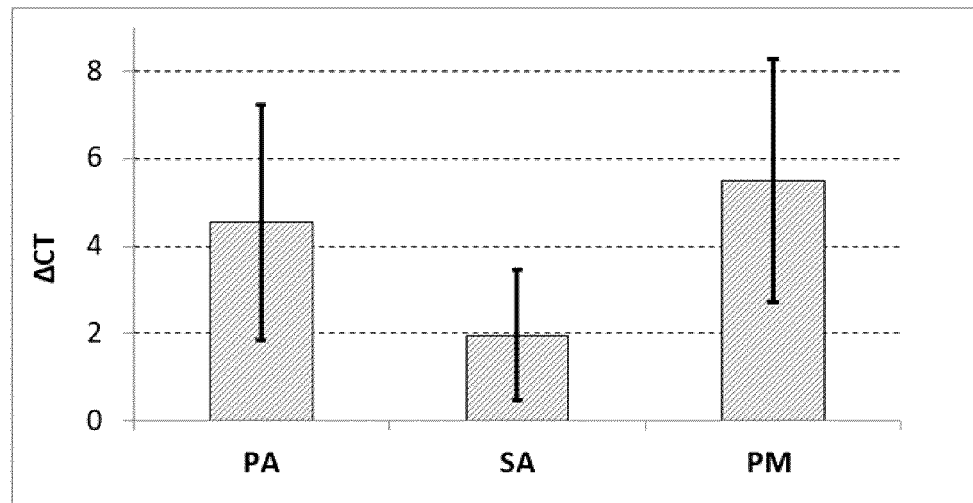
FIG. 6 plots $\Delta C_T$ values for different bacterial species obtained after contacting whole blood samples with a type 2 blood lysis reagent containing Triton X-100, SPS and a carbonate-bicarbonate buffer, performing centrifugal separation and concentration, heat lysis, and real-time reverse transcription polymerase chain reaction (real-time RT-PCR) as a measure of microbial cell intactness.

As shown in FIG. 6, the $\Delta C_T$ values for *Pseudomonas aeruginosa* (PA) and *Proteus mirabilis* (PM) were significantly higher than that of *Staphylococcus aureus* (SA), indicating that these microbial cell species appear to be negatively impacted by contact with the type 2 blood lysis reagent. Without intending to be limited by theory, it is believed that the observed performance degradation of the RT-PCR assay, following exposure of a whole blood sample to the type 2 blood lysis reagent and centrifugal processing, may be the result of one or more of the following causes: (i) microbial cell damage caused by the blood lysis reagent, which can give rise to the loss of the target cell contents or lowering sedimentation coefficient in the case of employing centrifugation based cell separation, (ii) removal of the microbial cells along with the blood debris during centrifugal processing (e.g. initial centrifugal separation and optional additional centrifugal cell washing cycles), and/or (iii) inhibiting the reverse transcription (RD and/or polymerase chain reaction (PCR) reactions by the transfer of high levels of blood debris to the final cell suspension.

Among these, the first two causes are expected to be more severe where the number of microbial cells in the initial sample is scarce, such as the case of bloodstream infections for which the number of microbial cells is typically less than 10 CFU/mL, because the first two causes are related to loss of analyte. In contrast, the performance degradation ($\Delta C_T$) due to assay inhibitors (the third cause listed above) can typically be compensated by performing additional amplification cycles, at the expense of target quantification accuracy.

In view of the results shown in FIG. 6, it was determined by the present inventors that a new type of reagent formulation would be needed to achieve suitable digestion of blood components when processing high (>1 ml) volumes of whole blood in an automated system, while maintaining the ability to perform subsequent (downstream) molecular amplification of a broad range of microbial cell species with sensitivity at the single CFU per ml level. Accordingly, the present inventors sought to develop a new lysis reagent formulation capable of processing high (>1 ml) volumes of whole blood in an automated system while preserving the intactness of a broad range of microbial cell types (e.g. species) in order to facilitate subsequent molecular amplification.

As an initial step in the search for an improved blood lysis reagent, the present inventors experimentally investigated the effect of different components of the type 1 and type 2 blood lysis reagent compositions on cell intactness.

Experimental Study of Effect of Triton X-100 on Microbial Cell Intactness

The effect of Triton X-100, one of the components of the type 2 blood lysis reagent, on microbial cell intactness, was experimentally investigated in the absence of a high pH environment (e.g. in the absence of a carbonate-bicarbonate buffer). Experiments were performed by contacting spiked phosphate buffer samples containing *Pseudomonas aeruginosa* (PA), *Proteus mirabilis* (PM), and *Staphylococcus aureus* (SA), prepared according to Example 3 below, with solutions containing Triton X-100 and SPS, such that the final concentrations of Triton X-100 in the various samples were 0, 0.188, 0.375, 0.55 and 0.75% w/v, and the SPS concentration was 15 mg/mL. Sample preparation and real time RT-PCR was performed according to the methods provided in Example 5 below. Spiked phosphate buffer samples, prepared according to the method of Example 3 below, were also prepared for spiked control and subjected to real time RT-PCR according to the method of Example 4 below. The $\Delta C_T$ value, determined based on the difference between the spiked phosphate buffer sample CT value and the spiked control CT value, was employed as a proxy for microbial cell intactness after exposure to Triton X-100.

Figure 7:
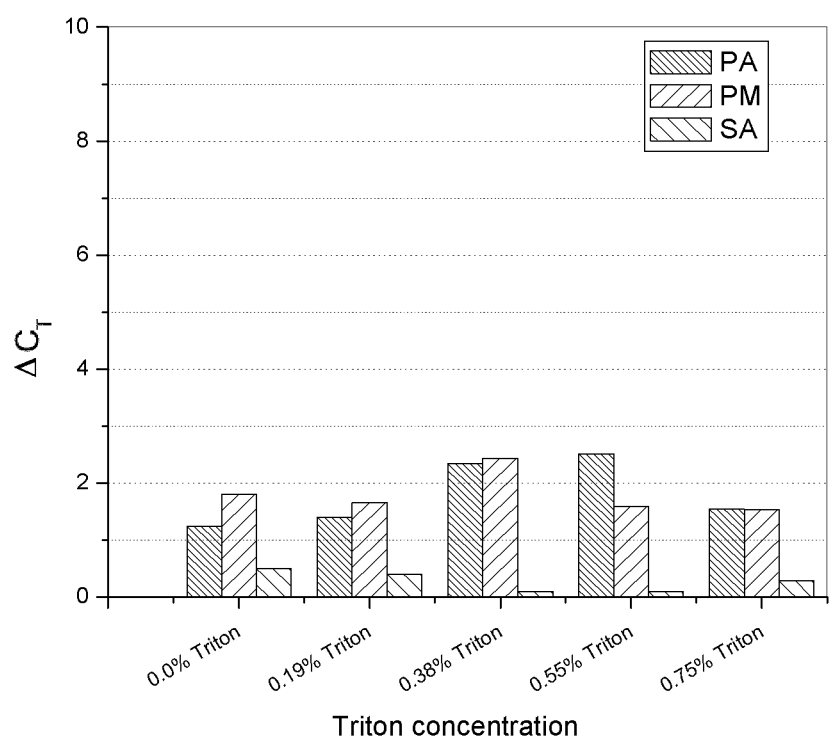
FIG. 7 plots the dependence of $\Delta C_T$ on Triton X-100 concentration for different bacterial species after contacting spiked phosphate buffer samples with a regent containing Triton X-100 and SPS, performing centrifugal separation and concentration, heat lysis, and real-time RT-PCR.

The resulting $\Delta C_T$ values, i.e. $C_T$(spiked phosphate buffer samples)-$C_T$(spiked control), presented in FIG. 7, show $\Delta C_T \leq 2$ for all cell types (especially the Gram-negative *Pseudomonas aeruginosa* (PA) and *Proteus mirabilis* (PM)), indicating that exposure to Triton X-100 during sample pre-treatment duration does not appear to significantly damage bacterial cells to the level of leaking appreciable amount of rRNA content. In other words, the presence of Triton X-100 did not appear to cause the loss of appreciable amounts of rRNA during the centrifugation process, facilitating detection of low-CFU-per-ml samples.

Experimental Study of High pH Environment on Microbial Cell Intactness

The effect of a high pH environment, one of the properties of the type 2 blood lysis reagent, on microbial cell intactness, was experimentally investigated, where the high pH was due to the carbonate-bicarbonate buffer component of the type 2 blood lysis reagent. Experiments were performed by contacting spiked phosphate buffer samples containing *Pseudomonas aeruginosa* (PA), *Proteus mirabilis* (PM), and *Staphylococcus aureus* (SA), prepared according to Example 3 below, with reagent solutions containing a carbonate-bicarbonate buffer and SPS. The reagent solutions were prepared by combining 1 ml of carbonate-bicarbonate buffer solutions, each prepared with buffer concentrations of 18, 56, 90, 100 and 220 mM respectively, and each having a pH of 10.4, 10.4, 10.3, 10.3 and 10.2 respectively, with 1 ml of a solution having a concentration of 30 mg/ml of SPS, to obtain reagent solutions having a volume of 2 ml and an SPS concentration of 15 mg/ml, pH values of 10.3, 10.3, 10.3, 10.3 and 10.2 respectively, and buffer concentrations of 9, 28, 45, 50 and 110 mM respectively. After mixing the 1 ml of the reagent solutions with 1 ml of the spiked phosphate buffer samples, the SPS concentration was 7.5 mg/mL and the pH values were in the range of 9.5-10 and the buffer concentrations were 4.5, 14, 22.5, 25 and 55 mM, respectively. Sample preparation and real time RT-PCR was performed according to the methods provided in Example 5 below. Spiked phosphate buffer samples, prepared according to the method of Example 3 below, were also prepared for spiked control and subjected to real time RT-PCR according to the method of Example 4 below. The $\Delta C_T$ value, determined based on the difference between the spiked phosphate buffer sample $C_T$ value and the spiked control $C_T$ value, was employed as a proxy for microbial cell intactness.

Figure 8:
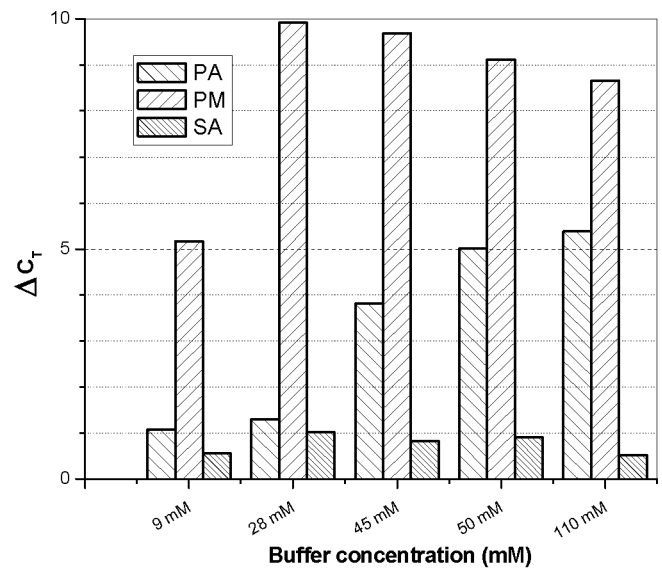
FIG. 8 plots the dependence of $\Delta C_T$ on buffer concentration for different bacterial species after contacting spiked phosphate buffer samples with a regent containing a carbonate-bicarbonate buffer and SPS, performing centrifugal separation and concentration, heat lysis, and real-time RT-PCR.

The resulting $\Delta C_T$ values, presented in FIG. 8, show significant increases in $\Delta C_T$ for both *Pseudomonas aeruginosa* (PA) and *Proteus mirabilis* (PM), indicating that exposure to a high pH environment during sample pre-treatment can significantly damage bacterial cells to the level of leaking appreciable amount of rRNA content for these species. It is noted that even the reagents that were prepared with carbonate-bicarbonate buffers having relatively low concentrations (which were diluted further upon mixing) led to appreciable $\Delta C_T$ loss for *Proteus mirabilis* (PM).

Type 3 Blood Lysis Reagent with Saponin and Alkaline pH

The preceding examples illustrate that the loss of signal that was observed in FIG. 6 for the case of a type 2 blood lysis reagent appeared to be due to the presence of the high pH environment associated with this reagent type. In order to attempt to overcome this limitation of the type 2 blood lysis reagent, and also to overcome the aforementioned limitations of the type 1 blood lysis reagent, the present inventors considered the mechanisms of the components of the type 1 and type 2 blood lysis reagents.

Understanding that saponin's hemolytic activity is due to an interaction with cholesterol, which is present on the membrane of eukaryotic cells but absent on the membrane of prokaryotic (microbial) cells, the present inventors hypothesized that saponin, as a surfactant, may form a layer over the microbial cells without causing damage to the microbial cells. Without intending to be limited by theory, the present inventors further hypothesized that if a reagent were provided with both saponin and a high pH, the surfactant layer generated by saponin may act as a protective layer, shielding the microbial cells from the otherwise deleterious effect of the high pH environment. In other words, the present inventors surmised that a microbial cell, when contacted with a reagent having both saponin and a high pH, may be coated by the saponin and effectively shielded from attack by the products of the alkaline buffer in the reagent.

To test this hypothesis, the effect of the combination of saponin and a high pH environment on microbial cell intactness was experimentally investigated for spiked phosphate buffer samples. Experiments were performed by contacting spiked phosphate buffer samples containing *Pseudomonas aeruginosa* (PA), *Proteus mirabilis* (PM), and *Staphylococcus aureus* (SA), prepared according to Example 3 below, with reagent solutions containing saponin, SPS and a carbonate-bicarbonate buffer. The reagent solutions were prepared by combining 1 ml of carbonate-bicarbonate buffer solutions, each prepared with buffer concentrations of 18, 56, 90, 100 and 220 mM respectively, and each having a pH of 10.4, 10.3, 10.3, 10.3 and 10.2 respectively, with 1 ml of a solution having a concentration of 30 mg/ml of SPS, and 60 mg/ml of saponin to obtain reagent solutions each having a volume of 2 ml, an SPS concentration of 15 mg/ml, a saponin concentration of 30 mg/ml, pH values of 7.2, 9.2, 9.7, 9.9, and 10 respectively and buffer concentrations of 9, 28, 45, 50 and 110 mM respectively. After mixing the 1 ml of the reagent solutions with 1 ml of the spiked phosphate buffer samples, the SPS concentration was 7.5 mg/mL, the saponin concentration was 15 mg/ml, the pH values were between 7 and 10 and the buffer concentrations were 4.5, 14, 22.5, 25 and 55 mM respectively. Centrifugal separation and real time RT-PCR was subsequently performed according to the methods provided in Example 5 below. Spiked phosphate buffer samples, prepared according to the method of Example 3 below, were also prepared for spiked control and subjected to real time RT-PCR according to the method of Example 4 below. The $\Delta C_T$ value, determined based on the difference between the spiked phosphate buffer sample $C_T$ value and the spiked control $C_T$ value, was employed as a proxy for microbial cell intactness.

Figure 9A:
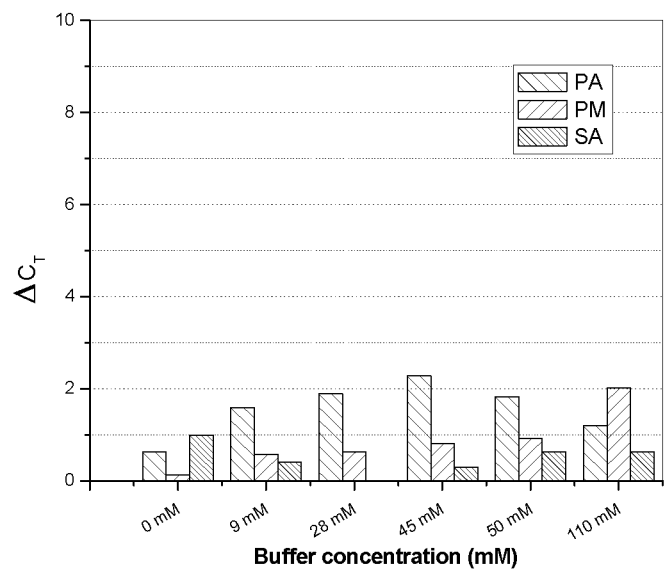
FIG. 9A plots the dependence of $\Delta C_T$ on buffer concentration for different bacterial species after contacting spiked phosphate buffer samples with a regent containing a carbonate-bicarbonate buffer, saponin and SPS, performing centrifugal separation and concentration, heat lysis and real-time RT-PCR.

The resulting $\Delta C_T$ values, presented in FIG. 9A, demonstrate that the presence of saponin appears to safeguard the microbial cells from exposure to a high pH environment during sample pre-treatment for each of the three different bacterial species tested. The present inventors concluded that a new blood lysis reagent formulation for the selective lysis of blood cells, henceforth referred to as a type 3 blood lysis reagent, containing saponin, SPS, an alkaline pH (for example, via the presence of a carbonate buffer), and optionally a non-ionic surfactant such as Triton X-100, could be effective for performing hemolysis while maintaining the intactness of a wide variety of microbial species.

The present inventors then experimentally investigated the effect of the type 3 blood lysis reagent on cell intactness for whole blood samples. Experiments were performed by contacting spiked whole blood samples with a volume of 3 ml containing *Pseudomonas aeruginosa* (PA), *Proteus mirabilis* (PM), and *Staphylococcus aureus* (SA), prepared according to Example 2 below, with a type 3 blood lysis reagent. The type 3 blood lysis reagent solution was prepared by combining 10 ml of a carbonate-bicarbonate buffer solution prepared with a buffer concentration of 200 mM and a pH of 10.1, with 10 ml of a solution having a concentration of 30 mg/ml of SPS, 60 mg/mL of saponin, and 3% w/v of Triton X-100 to obtain reagent solutions having a volume of 20 ml, an SPS concentration of 15 mg/ml, saponin concentration of 30 mg/ml, a Triton X-100 concentration of 1.5% w/v, a buffer concentration of 100 mM, and a pH of 10.0. After mixing 5 ml of the type 3 blood lysis reagent with 3 ml of whole blood sample, the SPS concentration was 9.375 mg/mL, the saponin concentration was 18.75 mg/mL, the Triton X-100 concentration was 0.94% w/v, the pH value was 9.2, and the effective buffer concentration was 62.5 mM.

Spiked phosphate buffer samples were prepared according to the method of Example 3. Centrifugal separation and real time RT-PCR was subsequently performed according to the methods provided in Examples 6 and 7 below for spiked phosphate buffer samples as spiked controls and spiked whole blood samples, respectively. The threshold cycle value ($C_T$ value; i.e. the number of the PCR cycle after which the assay signal increases above a noise threshold value) was measured, and the difference in $C_T$ values, $\Delta C_T$, was determined based on the difference between the spiked whole blood $C_T$ value and the spiked control $C_T$ value.

Figure 9B:
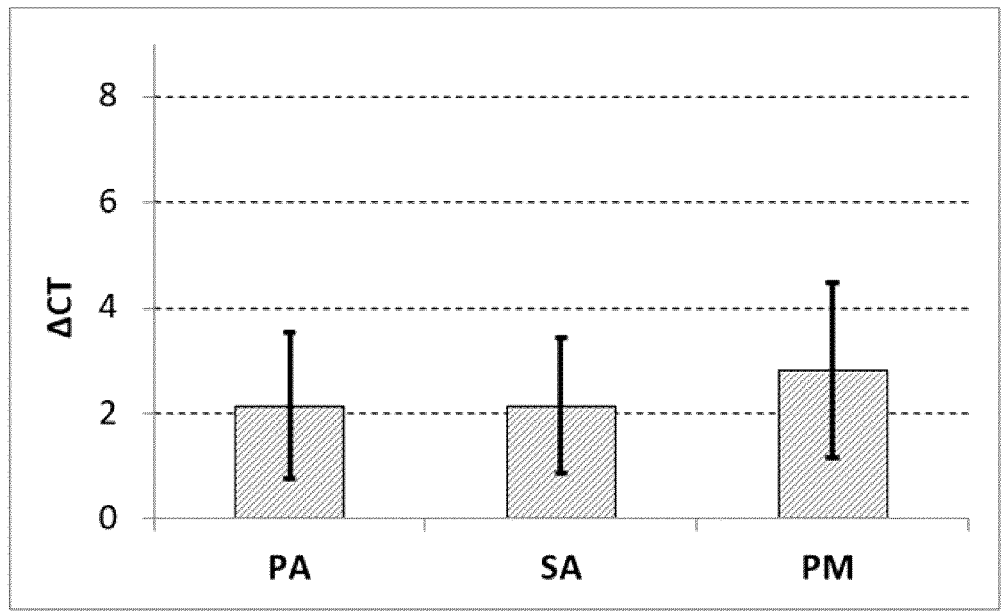
FIG. 9B plots $\Delta C_T$ values for different bacterial species obtained after contacting whole blood samples with a type 3 blood lysis reagent containing saponin, SPS, a carbonate-bicarbonate buffer and Triton X-100, performing centrifugal separation and concentration, heat lysis and real-time RT-PCR.
Figure 9C:
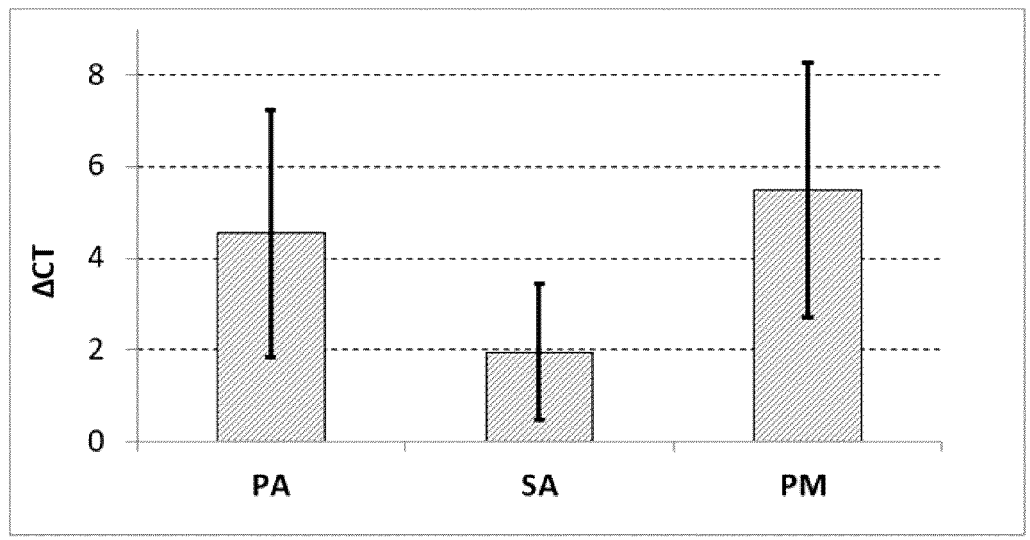
FIG. 9C plots $\Delta C_T$ values for different bacterial species obtained after contacting whole blood samples with a type 2 blood lysis reagent containing Triton X-100, SPS and a carbonate-bicarbonate buffer, performing centrifugal separation and concentration, heat lysis, and real-time RT-PCR. (previously shown in FIG. 6).

As shown in FIG. 9B, the $\Delta C_T$ values for *Pseudomonas aeruginosa* (PA), *Proteus mirabilis* (PM) and *Staphylococcus aureus* (SA) were all significantly lower than those obtained using the type 2 blood lysis reagent (FIG. 9C again shows the results obtained by processing whole blood samples with a type 2 blood lysis reagent, as originally shown in FIG. 6), demonstrating the success of the type 3 type blood lysis reagent for the processing of whole blood samples. Furthermore, the type 3 blood lysis reagent was successful in performing hemolysis without visible residue (i.e. without visible blood debris) for a wide range of concentrations of whole blood, thereby achieving both (i) recovery intact microbial cells with nucleic acids and (ii) digestion of residual blood components without visible blood debris, even after centrifugation.

The inventors performed a series of experiments to investigate the effect of different concentrations of the various components of the new type 3 blood lysis reagent on the performance of the reagent when processing whole blood sample spiked with microbial cells, as explained below.

Experimental Study of Dependence of Type 3 Blood Lysis Reagent Performance on Saponin Concentration for Processing of Whole Blood Samples Experiments were performed to investigate the dependence of the performance of the type 3 blood lysis reagent on saponin concentration for the processing of whole blood samples spiked with microbial cells. Experiments were performed by contacting spiked whole blood samples with a volume of 3 ml containing *Pseudomonas aeruginosa* (PA), *Proteus mirabilis* (PM), and *Staphylococcus aureus* (SA), prepared according to Example 2 below, with various type 3 blood lysis reagents. Various type 3 blood lysis reagent solutions were prepared by combining 10 ml of a carbonate-bicarbonate buffer solution prepared with a buffer concentration of 200 mM and a pH of 10.1, with 10 ml of a solution having a concentration of 30 mg/ml of SPS, a saponin concentration ranging from 0-80 mg/ml, and 3% w/v of Triton X-100 to obtain reagent solutions having a volume of 20 ml, an SPS concentration of 15 mg/ml, saponin concentration in the range of 0-40 mg/ml, a Triton X-100 concentration of 1.5%, a buffer concentration of 100 mM, and pH values were in the range of 9.5-10. After mixing 5 ml of the type 3 blood lysis reagent with 3 ml of whole blood sample, the SPS concentration was 9.375 mg/mL, the saponin concentration was in the range of 6.25-25 mg/mL, the Triton X-100 concentration was 0.94% w/v, the pH value was approximately 9.2, and the effective buffer concentration was 62.5 mM. Spiked phosphate buffer samples were prepared according to the method of Example 3. Centrifugal separation and real time RT-PCR was subsequently performed according to the methods provided in Examples 6 and 7 below for spiked phosphate buffer samples for spiked controls and spiked whole blood samples, respectively. The threshold cycle value ($C_T$ value; i.e. the number of the PCR cycle after which the assay signal increases above a noise threshold value) was measured, and the difference in $C_T$ values, $\Delta C_T$, was determined based on the difference between the spiked whole blood $C_T$ value and the spiked control $C_T$ value.

Figure 10:
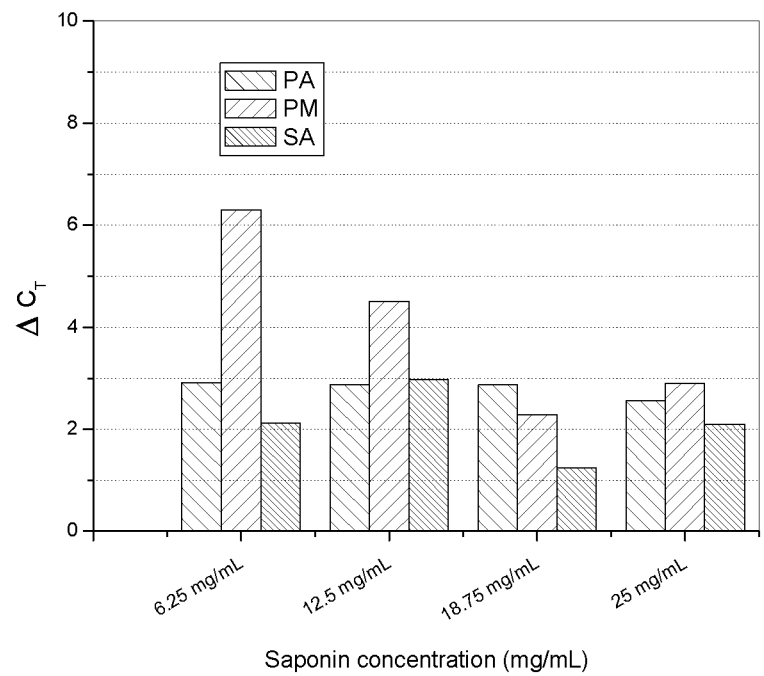
FIG. 10 plots the dependence of $\Delta C_T$ on saponin concentration for different bacterial species after contacting whole blood samples with type 3 blood lysis reagents containing different concentrations of saponin, SPS, a carbonate-bicarbonate buffer and Triton X-100, performing centrifugal separation and concentration, heat lysis and real-time RT-PCR.

As shown in FIG. 10, the $\Delta C_T$ values for all three microbial species were less than 5 for saponin concentrations of 12.5 mg/ml and greater. The protective effect of saponin for all microbial species appeared to be fully realized for saponin concentrations of 18.75 mg/ml and greater.

Experimental Study of Dependence of Type 3 Blood Lysis Reagent Performance on Triton X-100 Concentration for Processing of Whole Blood Sample Experiments were performed to investigate the dependence of the performance of the type 3 blood lysis reagent on the concentration of Triton X-100 for the processing of whole blood samples spiked with microbial cells. Experiments were performed by contacting spiked whole blood samples with a volume of 3 ml containing *Pseudomonas aeruginosa* (PA), *Proteus mirabilis* (PM), and *Staphylococcus aureus* (SA), prepared according to Example 2 below, with various type 3 blood lysis reagents. Various type 3 blood lysis reagent solutions were prepared by combining 10 ml of a carbonate-bicarbonate buffer solution prepared with a buffer concentration of 200 mM and a pH of 10.1, with 10 ml of a solution having a concentration of 30 mg/ml of SPS, a saponin concentration of 60 mg/mL, and a Triton X-100 concentration ranging from 0-2.25% w/v, to obtain reagent solutions having a volume of 20 ml, an SPS concentration of 15 mg/ml, a saponin concentration of 30 mg/ml, a Triton X-100 concentration ranging from 0-1.12% w/v, a buffer concentration of 100 mM, and pH values were in the range of 9.5-10. After mixing 5 ml of the type 3 blood lysis reagent with 3 ml of whole blood sample, the SPS concentration was 9.375 mg/mL, the saponin concentration was 18.75 mg/mL, the Triton X-100 concentration in the range was 0-0.7% w/v, the pH value was 9.2, and the effective buffer concentration was 62.5 mM. Spiked phosphate buffer samples were prepared according to the method of Example 3. Centrifugal separation and real time RT-PCR was subsequently performed according to the methods provided in Examples 6 and 7 below for spiked phosphate buffer samples as spiked controls and spiked whole blood samples, respectively. The threshold cycle value ($C_T$ value; i.e. the number of the PCR cycle after which the assay signal increases above a noise threshold value) was measured, and the difference in $C_T$ values, $\Delta C_T$, was determined based on the difference between the spiked whole blood $C_T$ value and the spiked control $C_T$ value.

Figure 11A:
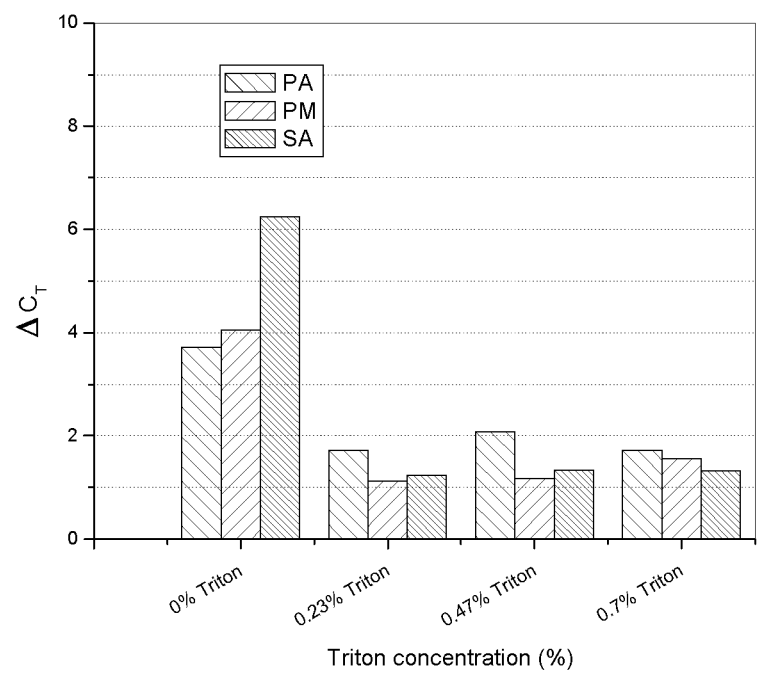
FIG. 11A plots the dependence of $\Delta C_T$ on Triton X-100 concentration for different bacterial species after contacting whole blood samples with type 3 blood lysis reagents containing saponin, SPS a carbonate-bicarbonate buffer, and different concentrations of Triton X-100, performing centrifugal separation and concentration, heat lysis and real-time RT-PCR.

As shown in FIG. 11A, the $\Delta C_T$ values for all three microbial species were less than 5, and substantially independent of Triton X-100 concentration, for Triton X-100 concentrations of 0.23% w/v and greater.

Experimental Study of Dependence of Type 3 Blood Lysis Reagent Performance on Different Non-Ionic Detergents for Processing of Whole Blood Samples An experiment was performed to demonstrate the suitability of Tween 20 as a non-ionic detergent. Experiments were performed by contacting spiked whole blood samples with a volume of 3 ml containing *Pseudomonas aeruginosa* (PA), *Proteus mirabilis* (PM), and *Staphylococcus aureus* (SA), prepared according to Example 2 below, with type 3 blood lysis reagents. Two different type 3 blood lysis reagent solutions were prepared. One blood lysis reagent was prepared by combining 10 ml of a carbonate-bicarbonate buffer solution prepared with a buffer concentration of 200 mM and a pH of 10.1, with 10 ml of a solution having a concentration of 30 mg/ml of SPS, a saponin concentration of 60 mg/mL, and a Triton X-100 concentration of 3%. The other blood lysis reagent was prepared by combining 10 ml of a carbonate-bicarbonate buffer solution prepared with a buffer concentration of 200 mM and a pH of 10.1, with 10 ml of a solution having a concentration of 30 mg/ml of SPS, a saponin concentration of 60 mg/mL, and a Tween-20 concertation of 3%. The resulting blood lysis reagent solutions had volumes of 20 ml, an SPS concentration of 15 mg/ml, a saponin concentration of 30 mg/ml, a Triton X-100 or Tween-20 concentration of 1.5%, a buffer concentration of 100 mM, and pH values near 10. After mixing 5 ml of the type 3 blood lysis reagent with 3 ml of whole blood sample, the SPS concentration was 9.375 mg/mL, the saponin concentration was 18.75 mg/mL, the Triton X-100 or Tween-20 concentration was 0.94% w/v, the pH value was 9.2, and the effective buffer concentration was 62.5 mM. Spiked phosphate buffer samples were prepared according to the method of Example 3. Centrifugal separation and real time RT-PCR was subsequently performed according to the methods provided in Examples 6 and 7 below for spiked phosphate buffer samples as spiked controls and spiked whole blood samples, respectively. The threshold cycle value ($C_T$ value; i.e. the number of the PCR cycle after which the assay signal increases above a noise threshold value) was measured, and the difference in $C_T$ values, $\Delta C_T$, was determined based on the difference between the spiked whole blood $C_T$ value and the spiked control $C_T$ value. The $\Delta C_T$ values, which are presented in FIG. 11B, illustrate that the $\Delta C_T$ values for all three microbial species were very similar in the case of Tween 20 and Triton X-100.

Experimental Study of Dependence Type 3 Blood Lysis Reagent Performance on Initial Carbonate-Bicarbonate Buffer Concentration for Processing of Whole Blood Samples Experiments were performed to investigate the dependence of the performance of the type 3 blood lysis reagent on the initial carbonate-bicarbonate buffer concentration for the processing of whole blood samples spiked with microbial cells. Experiments were performed by contacting spiked whole blood samples with a volume of 3 ml containing *Pseudomonas aeruginosa* (PA), *Proteus mirabilis* (PM), and *Staphylococcus aureus* (SA), prepared according to Example 2 below, with various type 3 blood lysis reagents. Various type 3 blood lysis reagent solutions were prepared by combining 10 ml of a carbonate-bicarbonate buffer solution prepared with buffer concentrations of 0, 20, 100, 200 and 400 mM and pH values were in the range of 9.5-10, with 10 ml of a solution having a concentration of 30 mg/ml of SPS, a saponin concentration of 60 mg/ml, and a Triton X-100 concentration of 3% w/v, to obtain reagent solutions having a volume of 20 ml, an SPS concentration of 15 mg/ml, a saponin concentration of 30 mg/ml, a Triton X-100 concentration of 1.5%, pH values of 4.7, 7.0, 9.8, 9.9, and 10.0 respectively and buffer concentrations of 0, 10, 50, 100 and 200 mM. After mixing 5 ml of the type 3 blood lysis reagent with 3 ml of whole blood sample, the SPS concentration was 9.375 mg/mL, the saponin concentration was 18.75 mg/mL, the Triton X-100 concentration was 0.94% w/v, the pH values were 7.2, 9.2, 9.7, 9.9 and 10.0, and the effective buffer concentrations were 0, 6.25, 31.25, 62.5 and 125 mM. Spiked phosphate buffer samples were prepared according to the method of Example 3. Centrifugal separation and real time RT-PCR was subsequently performed according to the methods provided in Examples 6 and 7 below for spiked phosphate buffer samples as spiked controls and spiked whole blood samples, respectively. The threshold cycle value ($C_T$ value; i.e. the number of the PCR cycle after which the assay signal increases above a noise threshold value) was measured, and the difference in $C_T$ values, $\Delta C_T$, was determined based on the difference between the spiked whole blood $C_T$ value and the spiked control $C_T$ value.

Figure 12A:
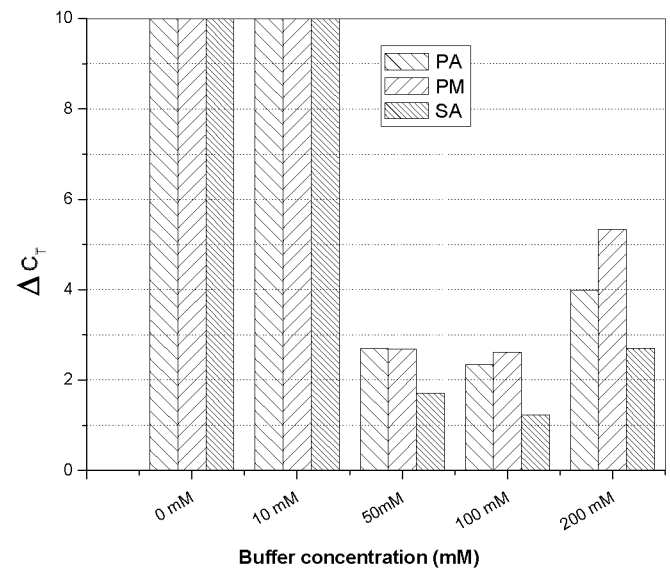
FIG. 12A plots the dependence of $\Delta C_T$ on buffer concentration for different bacterial species after contacting whole blood samples with type 3 blood lysis reagents containing saponin, SPS, different concentrations of carbonate-bicarbonate buffer and Triton X-100, performing centrifugal separation and concentration, heat lysis and real-time RT-PCR.

As shown in FIG. 12A, the $\Delta C_T$ values for all three microbial species were less than 5 for initial carbonate-bicarbonate buffer concentrations ranging between 50 mM and 200 mM. For initial carbonate-bicarbonate buffer concentrations of 10 mM and below, the $\Delta C_T$ values were found to be in excess of 10. Without intending to be limited by theory, is believed that this effect is due to insufficient buffering capacity of the blood lysis reagent, such that after mixing the reagent with blood the mixture pH drops towards the pH value of blood which is about 7.4. Thus, the medium is not sufficiently basic to enable sufficient digestion of blood cell debris. The $\Delta C_T$ value was also found to rise for initial carbonate-bicarbonate concentrations of 200 mM, which may be due to increased buffering capacity of the reagent such that the mixture pH is kept close to the initial pH value of the blood lysis reagent. This pH could damage some bacterial cells, in particular Gram-negative bacteria, possibly through elevated osmotic stress. Moreover, higher carbonate concentration increases the density of the blood lysis reagent and consequently the density of lysed blood. This result in longer sedimentation time and longer exposer to the deleterious effect of the reagent before the first wash cycle. For instance, the density of the blood lysis reagent having initial carbonate-bicarbonate concentrations of 100, 250, and 500 mM, is respectively 1.01, 1.025, and 1.05 g/mL. Adding these reagents with a ratio of 5:3 to whole blood, having an average density of 1.06 g/mL, will yield the final mixtures with respective densities of 1.029, 1.038, and 1.054 g/mL. Thus, a bacterial cell with a density of 1.10 will need about 50% longer time to sediment.

Figure 12B:
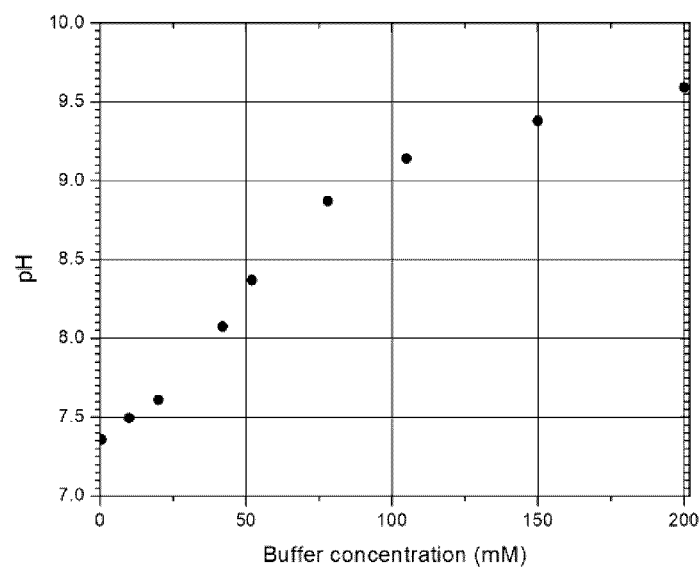
FIG. 12B plots the dependence of the post-mixing pH on the initial buffer concentration (the buffer concentration prior to mixing).

As shown in FIG. 12B, while the initial pH of the carbonate-bicarbonate buffer prior to mixing (i.e. prior to mixing with the whole blood sample and the other type 3 blood lysis reagent components) was close to 10, the pH of the mixture obtained after mixing the type 3 blood lysis reagent with whole blood dropped below 10 due to the limited buffering capacity of the reagent, with the final pH value being dependent on the initial carbonate-bicarbonate buffer concentration (i.e. dependent on the buffering capacity). The final post-mixing pH values corresponding to the initial carbonate-bicarbonate buffer concentrations of 0 mM and 200 mM were measured to be 7.4 and 9.6, respectively. This aspect was further investigated in a series of additional experiments that are described below.

Experimental Study of Dependence of Type 3 Blood Lysis Reagent Performance on pH for Processing of Whole Blood and Phosphate Buffer Samples Experiments were performed to study the effect of pH on the intactness of microbial cells for a type 3 blood lysis reagent based on the processing of spiked phosphate buffer samples and spiked whole blood samples. An initial set of experiments were performed by contacting spiked phosphate buffer samples containing *Pseudomonas aeruginosa* (PA), *Proteus mirabilis* (PM), and *Staphylococcus aureus* (SA), prepared according to Example 3 below, with various type 3 blood lysis reagents. Various type 3 blood lysis reagent solutions were prepared by combining 10 ml of a carbonate-bicarbonate buffer solution prepared with buffer concentrations of 200 mM and respective pH values of 9.5, 10 and 10.5, with 10 ml of a solution having a concentration of 30 mg/ml of SPS, a saponin concentration 60 mg/mL of saponin, and a Triton X-100 concentration of 3% w/v, to obtain reagent solutions having a volume of 20 ml, an SPS concentration of 15 mg/ml, a saponin concentration of 30 mg/ml, a Triton X-100 concentration of 1.5%, pH values of 9.6, 10.0 and 10.3 respectively, and buffer concentrations of 100 mM. After mixing 1 ml of the type 3 blood lysis reagent with 1 ml of spiked phosphate buffer sample, the SPS concentration was 7.5 mg/mL, the saponin concentration was 15 mg/mL, the Triton X-100 concentration was 0.75% w/v, the pH values were in the range of 9.5-10 and the effective buffer concentrations were 50 mM. Additional experiments were performed under similar conditions, but with a post-mixing Triton X-100 concentration of 0.375% w/v. Centrifugal separation and real time RT-PCR was subsequently performed according to the methods provided in Example 5 below. Spiked phosphate buffer samples, prepared according to the method of Example 3 below, were also prepared for spiked control and subjected to real time RT-PCR according to the method of Example 4 below. The $\Delta C_T$ value, determined based on the difference between the spiked phosphate buffer sample $C_T$ value and the spiked control $C_T$ value, was employed as a proxy for microbial cell intactness.

The resulting $\Delta C_T$ values for this experiment involving spiked phosphate buffer samples are presented in FIGS. 13A and 13B, where FIG. 13A pertains to a post-mixing Triton X-100 concentration of 0.75% w/v and FIG. 13B pertains to a post-mixing Triton X-100 concentration of 0.375% w/v, and where the horizontal axis labels refer to the pH of the original carbonate-bicarbonate buffer, prior to its combination with the other components of the reagent. The results show that reduced $\Delta C_T$ values are obtained for all tested species when the initial carbonate-bicarbonate pH employed to prepare the blood lysis reagent has a pH lower than 10.5 for both tested concentrations of Triton X-100, although lower $\Delta C_T$ values were obtained for the higher concentration of Triton X-100. These results suggest that exposure to a high pH environment during sample pre-treatment can lead to a signal loss even when saponin is present in the blood lysis reagent, and that saponin appears to have a better protective effect for lower reagent pH values. This aspect of the present disclosure is further investigated below.

A second set of experiments were performed by contacting spiked whole blood samples (in contrast to spiked phosphate buffer samples in FIGS. 13A and 13B) containing *Pseudomonas aeruginosa* (PA), *Proteus mirabilis* (PM), and *Staphylococcus aureus* (SA), prepared according to Example 2 below, with various type 3 blood lysis reagents. Various type 3 blood lysis reagent solutions were prepared by combining 10 ml of a carbonate-bicarbonate buffer solution prepared with buffer concentrations of 200 mM and respective pH values of 9.5, 10 and 10.5, with 10 ml of a solution having a concentration of 30 mg/ml of SPS, 60 mg/mL of saponin, and a Triton X-100 concentration of 3% w/v, to obtain reagent solutions having a volume of 20 ml, an SPS concentration of 15 mg/ml, a saponin concentration of 30 mg/ml, a Triton X-100 concentration of 1.5%, pH values of 9.6, 10.0 and 10.3 respectively and buffer concentrations of 100 mM. After mixing 1 ml of the type 3 blood lysis reagent with 1 ml of whole blood sample, the SPS concentration was 7.5 mg/mL, the saponin concentration was 15 mg/mL, the Triton X-100 concentration was 0.75% w/v, the pH values were 9.0, 9.2, and 9.7, and the effective buffer concentrations were 50 mM. Spiked phosphate buffer samples were prepared according to the method of Example 3. Centrifugal separation and real time RT-PCR was subsequently performed according to the methods provided in Examples 5 and 8 below for spiked phosphate buffer samples as spiked controls and spiked whole blood samples, respectively. The $\Delta C_T$ value, determined based on the difference between the spiked phosphate buffer sample $C_T$ value and the spiked control $C_T$ value, was employed as a proxy for microbial cell intactness.

Figure 14A:
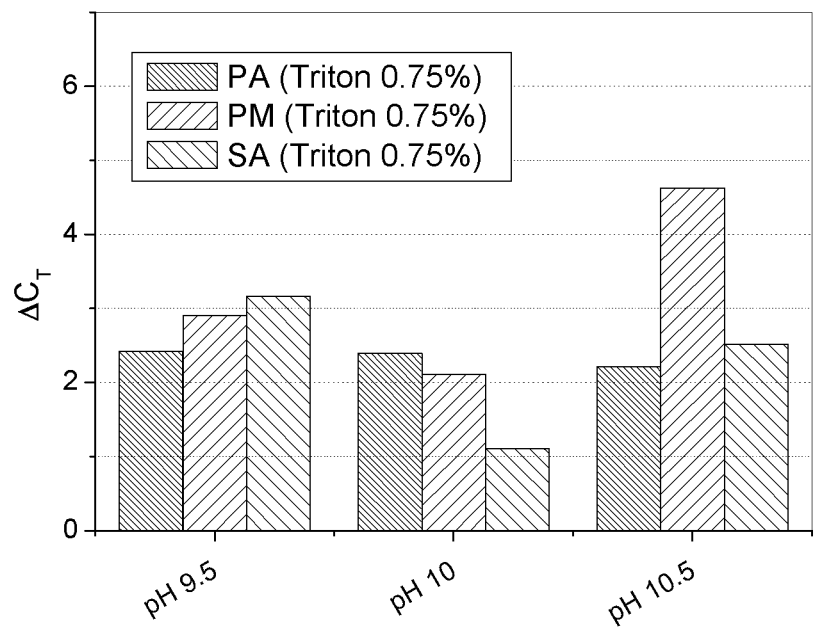
FIG. 14A plots $\Delta C_T$ values for different bacterial species and three different blood lysis reagent pH values (the pH values are those of the initial buffer prior to mixing with the other components of the blood lysis reagent) after contacting whole blood samples with type 3 blood lysis reagents with different pH values, containing saponin, SPS, a carbonate-bicarbonate buffer and Triton X-100, performing centrifugal separation and concentration, heat lysis and real-time RT-PCR.

The resulting $\Delta C_T$ values for this experiment involving whole blood samples are presented in FIG. 14A, which again demonstrate that reduced $\Delta C_T$ values are obtained for all tested species when the initial blood lysis reagent has a pH lower than 10.5.

It is noted that due to the buffering capacity of blood, the final pH value of the type 3 blood lysis reagent and initial buffer concentration are not independent parameters. Indeed, after mixing the type 3 blood lysis reagent with whole blood, the pH value of the mixture is observed to drop from the initial level of the pH value employed to prepare the blood lysis reagent, as indicated in FIG. 12B.

The amount of the drop in pH from the initial pH of the carbonate-bicarbonate buffer to the final pH of the mixture with whole blood has been observed to depend on the initial buffer concentration employed to prepare the blood lysis reagent. To investigate this further, various type 3 blood lysis reagent with different initial pH and buffer concentration values were prepared and mixed with whole blood, and pH measurements were made before and after mixing of the blood lysis reagents with whole blood. The type 3 blood lysis reagent solutions were prepared by combining 10 ml of a carbonate-bicarbonate buffer solution prepared with respective pH values of 9.5, 10 and 10.5, each prepared with three buffer concentrations of 100, 150 and 200 mM, with 10 ml of a solution having a concentration of 30 mg/ml of SPS, 60 mg/mL of saponin, and a Triton X-100 concentration of 3% w/v, to obtain reagent solutions having a volume of 20 ml, an SPS concentration of 15 mg/ml, a saponin concentration of 30 mg/ml, a Triton X-100 concentration of 1.5%, pH values near 9.6, 10 and 10.3 for the buffer concentrations of 50, 75, and 100 mM respectively. After mixing 1 ml of the blood lysis reagent with 1 ml of the whole blood sample, the SPS concentration was 7.5 mg/mL, the saponin concentration was 15 mg/mL, the Triton X-100 concentration was 0.75% w/v, pH values were between 9.0-9.2, 9.2-9.5 and 9.7-9.9 for the effective buffer concentrations of 25, 37.5 and 50 mM, respectively.

Figure 14B:
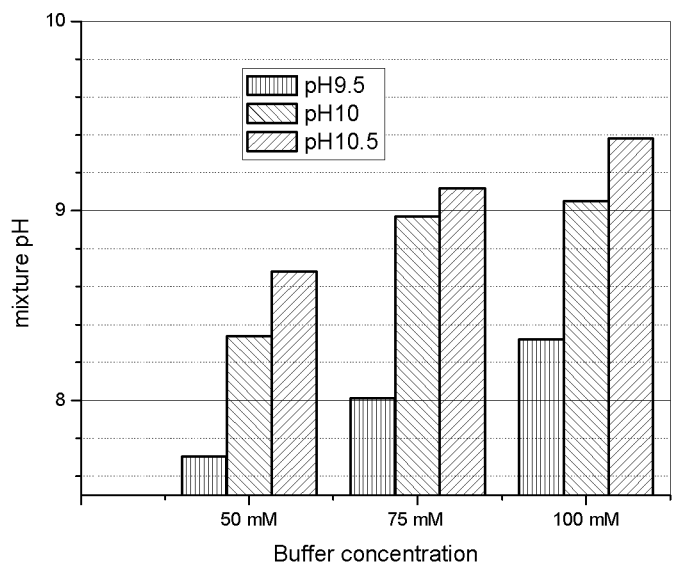
FIG. 14B plots the pH of the final mixture (type 3 blood lysis reagent+whole blood) as a function of the pH of the initial carbonate-bicarbonate buffer (9.5, 10 and 10.5) employed to prepare the type 3 blood lysis reagent.

FIG. 14B plots the pH of the final mixture (type 3 blood lysis reagent+whole blood) as a function of the initial carbonate-bicarbonate buffer concentration employed to prepare the type 3 blood lysis reagent, for the different values of the pH of the initial carbonate-bicarbonate buffer (9.5, 10 and 10.5). As can be observed in the figure, the pH values drop after mixing the blood lysis reagent with whole blood as a result of the acid-base reaction between the buffering system of the blood lysis reagent and the $HCO_3^-$/$H_2CO_3$ buffer in the blood. However, the blood lysis reagent with the highest buffering capacity and highest pH was more resistant to decreases in pH upon mixing with whole blood. Overall, a starting pH between 10 and 10.5 having buffer concentration that is diluted to a range of 37.5 and 50 mM upon mixing with whole blood appear to result in a final pH in whole blood that is approximately 9 and 9.5.

The experiments above illustrate the effects of the final pH in the blood lysis reagent/whole blood mixtures on microbial cell recovery. This final pH is dependent on the carbonate buffer capacity in the blood lysis reagent and the initial pH of the buffer prior to its addition to the blood lysis reagent. The previous examples suggest that a target pH range between 9 and 9.5 can be achieved by using either a high concentration of carbonate buffer at a low starting pH, or by using a low concentration of buffer at high starting pH. In this example, both the buffer capacity in the blood lysis reagent and the initial pH were adjusted in order to achieve the same pH value in whole blood. These mixtures were then tested in cell recovery experiments in order to determine the influence of carbonate buffer concentration.

Figures 14C, 14D:
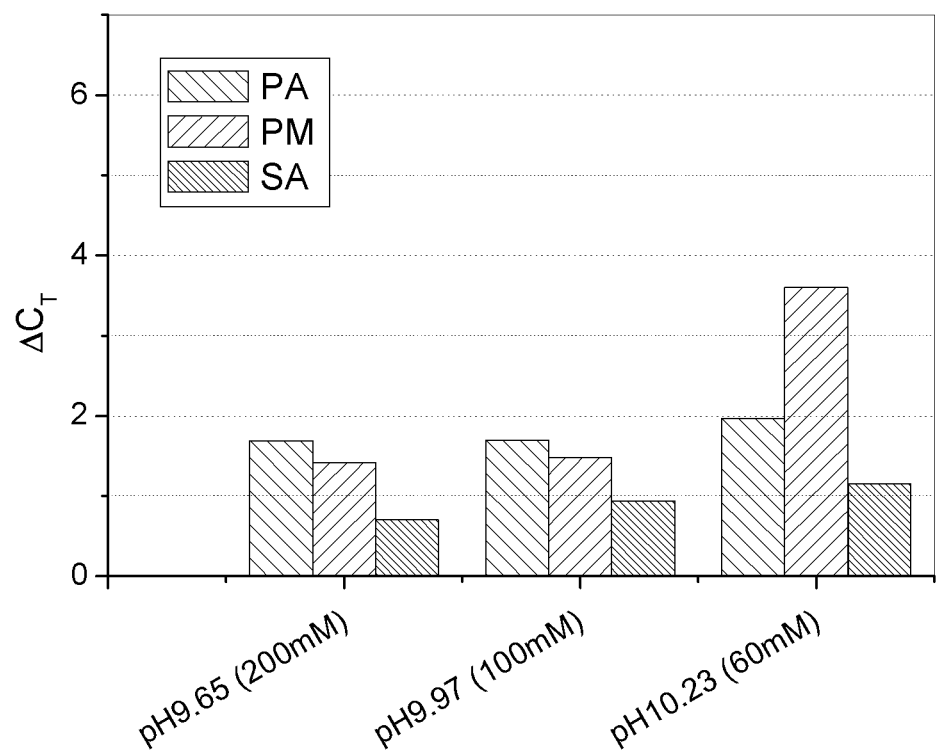
FIG. 14C is a table demonstrating the measured changes in pH during the preparation and subsequent use of a type 3 blood lysis reagent.
FIG. 14D plots $\Delta C_T$ values for different bacterial species and three different blood lysis reagent pH values (the pH values were measured prior to mixing with whole blood) after contacting whole blood samples with a type 3 blood lysis reagent containing saponin, SPS, a different concentration of carbonate-bicarbonate buffer and Triton X-100, performing centrifugal separation and concentration, heat lysis and real-time RT-PCR.

In another experiment, a set of blood lysis reagents were prepared with different pH values and buffer concentrations such that upon mixing with whole blood, a final pH value of approximately 9.5 would be achieved. FIG. 14C is a table that illustrates the preparation of suitable blood lysis reagents using a carbonate-bicarbonate buffer system. The table traces the pH values and the dilution of the original buffer concentration when the buffer is first mixed with reagent components to form a type 3 blood lysis reagent and subsequently mixed with whole blood. Stock solutions of 1M carbonate-bicarbonate buffer at pH values of 9.5 and 10.5 were prepared by mixing specific ratios of sodium carbonate and sodium bicarbonate. The dilutions of the buffers were carried out such that the final pH, after mixing to form the type 3 blood lysis reagent and then mixing with whole blood, would be similar (approximately 9.5). The type 3 blood lysis reagent solutions were prepared by combining 10 ml of a carbonate-bicarbonate buffer solution prepared with respective pH values of 9.66, 10.19 and 10.78, each prepared respectively with buffer concentrations of 400, 200 and 120 mM, with 10 ml of a solution having a concentration of 30 mg/ml of SPS, 60 mg/mL of saponin, and a Triton X-100 concentration of 3% w/v, to obtain reagent solutions having a volume of 20 ml, an SPS concentration of 15 mg/ml, a saponin concentration of 30 mg/ml, a Triton X-100 concentration of 1.5%, pH values of 9.65, 9.97 and 10.23, and buffer concentrations of 200, 100, and 60 mM. After mixing 5 ml of the blood lysis reagent with 3 ml the whole blood sample, the SPS concentration was 9.375 mg/mL, the saponin concentration was 18.75 mg/mL, the Triton X-100 concentration was 0.94% w/v, the effective buffer concentrations were 125, 62.5 and 37.5 mM, respectively, with nearly similar pH values of 9.45, 9.52, 9.56.

For instance, the buffer starting at the lowest pH was prepared at the highest concentration, while the lowest concentration buffer started with the highest pH. As the buffers were being diluted, pH changes would occur due to their reaction with the acidic saponin in the blood lysis reagent and with the $HCO_3^{-1}/H_2CO_3$ buffer system in the blood, and as expected the lowest concentration of carbonate buffer (60 mM prior to addition to whole blood, 37.5 mM effective buffer concentration after mixing with whole blood) underwent the largest changes in pH as each stage due to its weakest buffering capacity, whereas the highest concentration buffer was more resistant to pH changes.

An additional set of experiments were performed by contacting spiked whole blood samples containing *Pseudomonas aeruginosa* (PA), *Proteus mirabilis* (PM), and *Staphylococcus aureus* (SA), prepared according to Example 2 below, with the type 3 blood lysis reagents described in the table shown in FIG. 14C (i.e. with blood lysis reagent pH values and carbonate-bicarbonate buffer concentrations, of 9.65, 9.97, 10.23 and 200 mM, 100 mM and 60 mM, respectively). Spiked phosphate buffer samples were prepared according to the method of Example 3. Centrifugal separation and real time RT-PCR was subsequently performed according to the methods provided in Examples 5 and 8 below for spiked phosphate buffer samples as spiked controls and spiked whole blood samples, respectively. The $\Delta C_T$ value, determined based on the difference between the spiked whole blood sample $C_T$ value and the spiked control $C_T$ value, was employed as a proxy for microbial cell intactness.

The resulting $\Delta C_T$ values for this experiment involving whole blood samples are presented in FIG. 14D, which again demonstrate that reduced $\Delta C_T$ values are obtained for all tested species when the initial blood lysis reagent has a pH lower than 10.5.

It will be understood that the example carbonate buffer system that is employed in many of the example embodiments provided herein is employed merely as an illustrative example, and that other buffer systems may be employed in the alternative. Non-limited examples of other suitable alkaline buffers include borate, carbonate, CAPS (N-cyclohexyl-3-am inopropanesulfonic), CAPSO (3-(Cyclohexylamino)-2-hydroxy-1-propanesulfonic acid), CHES (2-(N-Cyclohexylamino) ethane Sulfonic acid), pyrophosphate, AMP (2-amino-2-methyl-1-propanol), and ethanolamine.

In order to demonstrate the operability of example alternative buffer systems, an experiment was performed by contacting spiked whole blood samples containing *Pseudomonas aeruginosa* (PA), *Proteus mirabilis* (PM), and *Staphylococcus aureus* (SA), prepared according to Example 2 below, with various type 3 blood lysis reagents containing Triton X-100, saponin, SPS and three different buffer systems. Various type 3 blood lysis reagent solutions were prepared by combining 10 ml of carbonate-bicarbonate, CAPS and CHES buffer solutions, prepared with buffer concentrations of 200 mM and pH values of 10 for each, with 10 ml of a solution having a concentration of 30 mg/ml of SPS, 60 mg/mL of saponin, and a Triton X-100 concentration of 3% w/v, to obtain the type 3 blood lysis reagent solutions having a volume of 20 ml, an SPS concentration of 15 mg/ml, a saponin concentration of 30 mg/ml, a Triton X-100 concentration of 1.5%, pH values of 9.43, 9.47 and 9.55 respectively and buffer concentrations of 100 mM for each. After mixing 5 ml of the type 3 blood lysis reagent with 3 ml the whole blood sample, the SPS concentration was 9.375 mg/mL, the saponin concentration was 18.75 mg/mL, the Triton X-100 concentration was 0.94% w/v, the effective buffer concentrations were 62.5 mM, with nearly similar pH values of 9.29, 9.10, 9.06 respectively, for the three different example buffer systems. Spiked phosphate buffer samples were prepared according to the method of Example 3. Centrifugal separation and real time RT-PCR was subsequently performed according to the methods provided in Examples 6 and 7 below for spiked phosphate buffer samples as spiked controls and spiked whole blood samples, respectively. The $\Delta C_T$ value, determined based on the difference between the spiked whole blood sample $C_T$ value and the spiked control $C_T$ value, was employed as a proxy for microbial cell intactness.

Figures 15A, 15B:
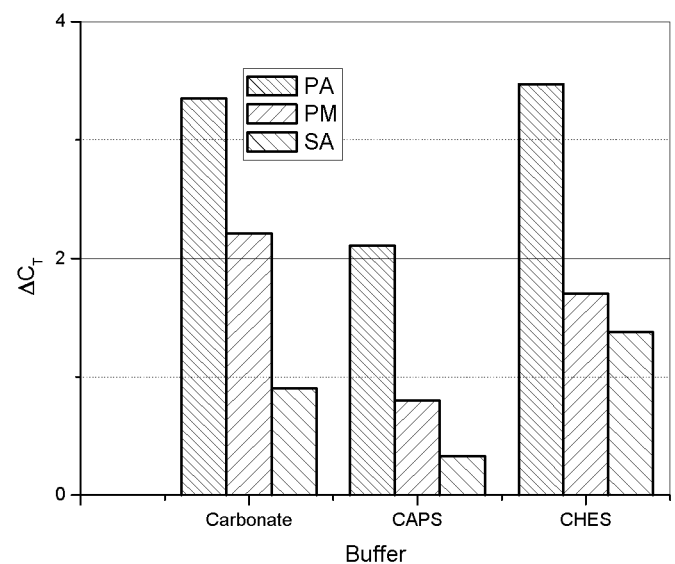
FIG. 15A plots $\Delta C_T$ values for different bacterial species and three different blood lysis reagents (each employing a different buffer system) after contacting whole blood samples with a type 3 blood lysis reagent containing saponin, SPS, a respective different buffer system and Triton X-100, performing centrifugal separation and concentration, heat lysis and real-time RT-PCR.
FIG. 15B is a table demonstrating the measured changes in pH of a type 3 blood lysis reagent containing saponin, SPS, a respective different buffer system pH10 and Triton X-100, before and after mixing with whole blood.

FIG. 15A plots the observed $\Delta C_T$ values for the different type 3 blood lysis reagent formulations using different buffers. The results indicate that there is no significance difference between the three buffer systems in terms of recovery in the context of a real time RT-PCR assay.

FIG. 15B is a table presenting the pH before and after mixing the type 3 blood lysis reagent with whole blood. These pH values are nearly similar and demonstrate that different buffer systems with similar pH values and ionic strength may be employed in a type 3 blood lysis reagent with similar hemolysis performance and microbial cell intactness.

Experimental Study of Dependence of Type 3 Blood Lysis Reagent Performance on SPS for Whole Blood Samples Processing The present inventors also experimentally investigated the role of SPS in the elimination of blood debris. As explained above, the presence of such debris can lead to entrapment and loss of microbial cells and can also impede automated centrifugation and/or filtration due to problems associated with the presence of a cake (caking). In addition, the debris may sediment during centrifugal washing and transfer to the final cell suspension. This may inhibit downstream assays on microbial cells or their lysates. A series of four experiments were performed in order to investigate the role of different components of the type 3 blood lysis reagent in the elimination of blood debris, with varying post-mixing concentrations of SPS. As will be explained below, it was found that the presence of SPS appears to play an important role in the reduction or elimination of blood debris after blood lysis and centrifugation. The four experiments were performed using whole blood samples that were not spiked with microbial cells, since the purpose of these experiments was to observe and investigate the formation of blood debris after blood lysis.

Figure 16A:
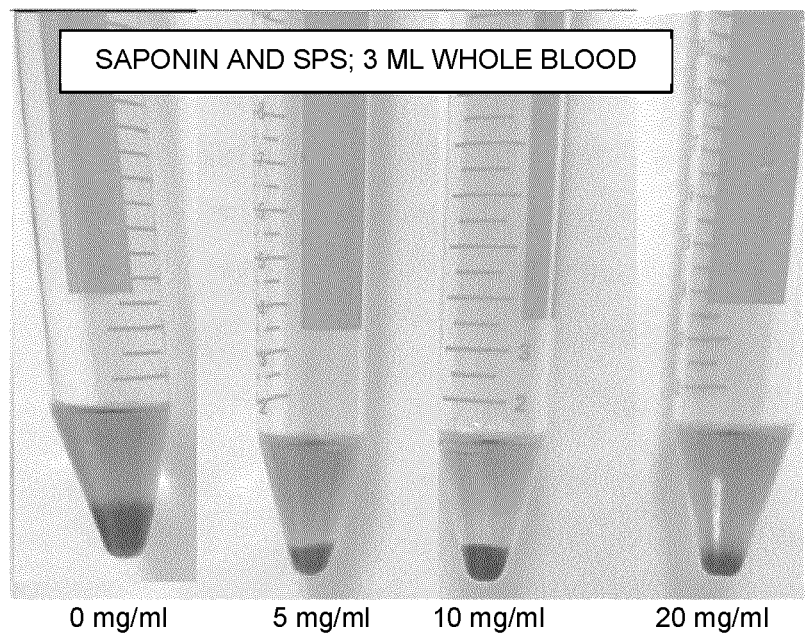
FIG. 16A shows images of centrifuge tubes after contacting whole blood samples having a volume of 3 ml with a reagent containing saponin and a different concentration of SPS followed by two centrifugal washing steps.

A first experiment was performed by mixing 3 ml of unspiked whole blood samples with 5 ml of various blood lysis reagent components containing saponin and SPS, according to the method described in Example 9, in the absence of Triton X-100 and a carbonate buffer, such that after mixing, the final saponin concentration was 18.75 mg/ml and the SPS concentration ranged from 0-20 mg/ml. FIG. 16A shows a photograph of the centrifuge tubes for the four samples. It is readily apparent that in the absence of the high pH environment facilitated by the carbonate-bicarbonate buffer, saponin and SPS are unable to achieve sufficient digestion of the blood components and significant blood debris is observed.

Figure 16B:
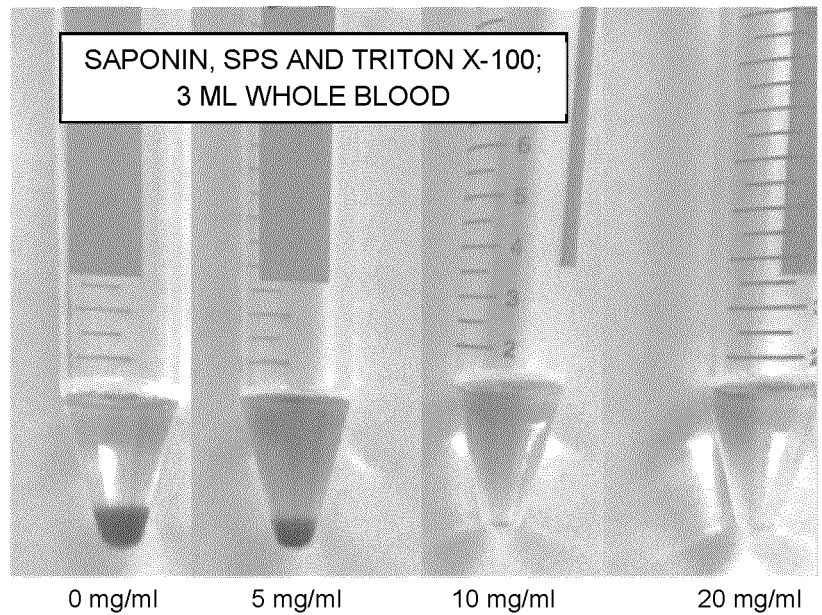
FIG. 16B shows images of centrifuge tubes after contacting whole blood samples having a volume of 3 ml with reagents containing saponin, different concentrations of SPS and Triton X-100, followed by two centrifugal washing steps.

A second experiment was performed by mixing 3 ml of unspiked whole blood samples with 5 ml of various lysis reagent components containing saponin, SPS, and Triton X-100, according to the method described in Example 9, in the absence of a carbonate-bicarbonate buffer, such that after mixing, the final saponin concentration was 18.75 mg/ml, the final Triton X-100 concentration was 0.75% w/v, and the SPS concentration ranged from 0-20 mg/ml. FIG. 16B shows a photograph of the centrifuge tubes for the four samples. The photographs show that only a very small amount of blood debris is present for an SPS concentration of 10 mg/ml, and that the blood debris appears to be completely eliminated for an SPS concentration of 20 mg/ml.

Figure 16C:
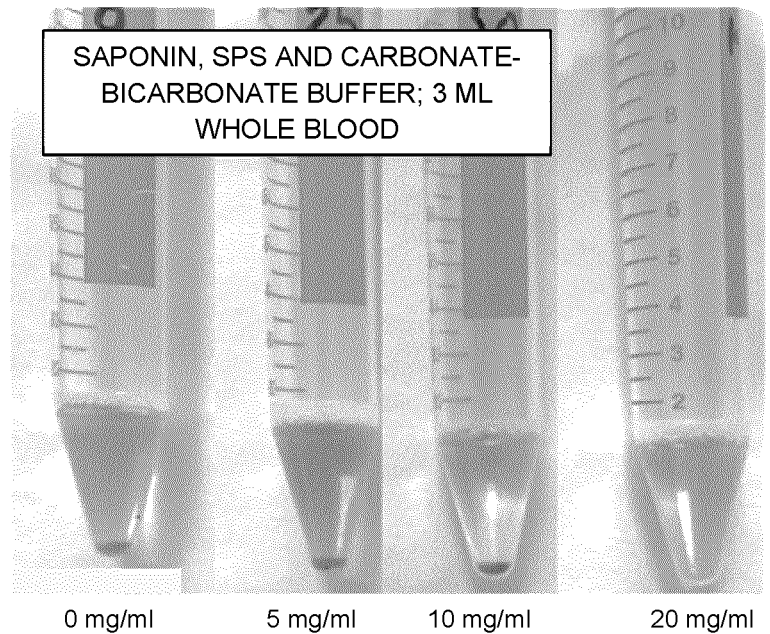
FIG. 16C shows images of centrifuge tubes after contacting whole blood samples having a volume of 3 ml with reagents containing saponin, different concentrations of SPS and a carbonate-bicarbonate buffer, followed by two centrifugal washing steps.

A third experiment was performed by mixing 3 mL of unspiked whole blood samples with 5 mL of various lysis reagent components containing saponin, SPS, and carbonate-bicarbonate buffer, according to the method described in Example 9, in the absence of Triton X-100. The lysis reagent solutions were prepared by combining 10 ml of a carbonate-bicarbonate buffer solution prepared with pH values in the range of 9.5-10, and buffer concentrations of 200 mM, with 10 ml of a solution having a SPS concentration in the range of 0-40 mg/ml, 60 mg/mL of saponin, to obtain reagent solutions having a volume of 20 ml, a saponin concentration of 30 mg/ml, an SPS concentration in the range of 0-20 mg/ml and buffer concentrations of 100 mM. After mixing 5 ml of the blood lysis reagent with 3 ml the whole blood sample, the SPS concentration was in the range of 0-12.5 mg/mL, the saponin concentration was 18.75 mg/mL, the effective buffer concentration was 62.5 mM. FIG. 16C shows a photograph of the centrifuge tubes for the four samples. The photographs show that a moderate amount of blood debris is present for SPS concentrations ranging between 0 and 10 mg/ml, and that the blood debris appears to be completely eliminated for an SPS concentration of 20 mg/ml.

Figure 16D:
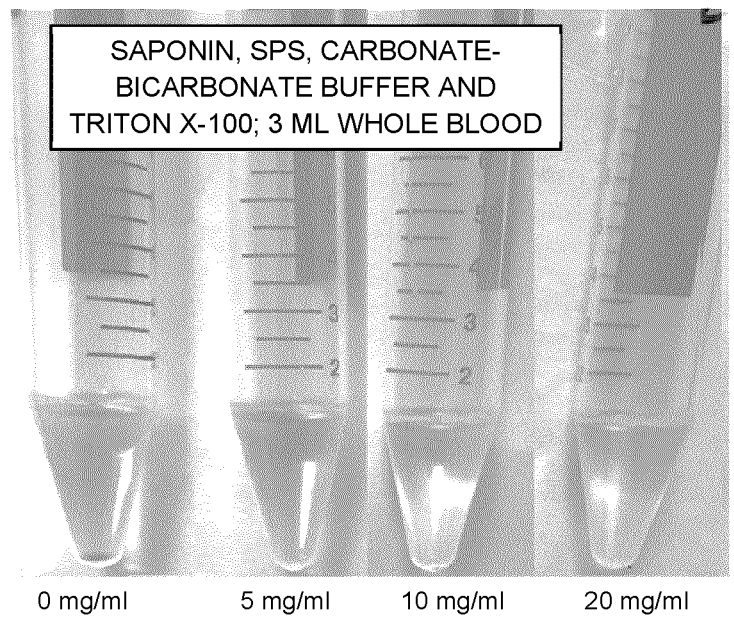
FIG. 16D shows images of centrifuge tubes after contacting whole blood samples having a volume of 3 ml with type 3 blood lysis reagents containing saponin, different concentrations of SPS, a carbonate-bicarbonate buffer and Triton X-100 followed by two centrifugal washing steps.

A fourth experiment was performed by mixing 3 mL of unspiked whole blood samples with 5 mL of type 3 blood lysis reagents containing saponin, SPS, Triton X-100 and carbonate buffer, according to the method described in Example 9. The type 3 blood lysis reagent solutions were prepared by combining 10 ml of a carbonate-bicarbonate buffer solution prepared with pH value were in the range of 9.5-10 and buffer concentration of 200 mM, with 10 ml of a solution having SPS in 0-40 mg/mL concentration range, 60 mg/mL of saponin, and a Triton X-100 concentration of 3% w/v, to obtain reagent solutions having a volume of 20 ml, an SPS concentration in range of 0-20 mg/ml, a saponin concentration of 30 mg/ml, a Triton X-100 concentration of 1.5%, and buffer concentrations of 100 mM. After mixing 5 ml of the blood lysis reagent with 3 ml of the whole blood sample, the SPS concentration was in the range of 0-12.5 mg/mL, the saponin concentration was 18.75 mg/mL, the Triton X-100 concentration was 0.94% w/v, the effective buffer concentrations were 62.5 mM. FIG. 16D shows a photograph of the centrifuge tubes for the four samples. The photographs show that a small amount of blood debris is present in the absence of SPS, and that the blood debris appears to be completely eliminated for SPS concentrations of 5-20 mg/ml. However, it is noted that even though the presence of blood debris (caking) is not observable in FIG. 16D for SPS concentrations of over 5 mg/ml, a small amount of blood debris is nonetheless present for the sample with 5 mg/ml that may be sufficient to have an impact on the performance of a downstream molecular assay. Therefore, as described below, an SPS concentration from 10 mg/mL to 30 mg/ml may be preferable for embodiments involving subsequent molecular assays. However, concentrations above 50 mg/ml, while reducing caking, may be too high in some applications as SPS is an inhibitor of some PCR enzymes.

The preceding four experiments visually demonstrate that SPS appears to play a significant role in the digestion of blood components and the reduction and/or elimination of blood debris, which can be important for automated sample preparation methods involving centrifugation, filtration, or other methods such as immunomagnetic and microfluidic-based separation. Indeed, the presence of SPS was observed to be correlated with a reduction in residual blood debris for (i) a type 3 blood lysis reagent, and (ii) other blood lysis reagents containing subsets of the components of a type 3 blood lysis reagent.

A further experiment was performed to investigate the dependence of the performance of the type 3 blood lysis reagent on SPS concentration for the processing of whole blood samples spiked with microbial cells. Experiments were performed by contacting spiked whole blood samples with a volume of 3 ml containing *Pseudomonas aeruginosa* (PA), *Proteus mirabilis* (PM), and *Staphylococcus aureus* (SA), prepared according to Example 2 below, with various type 3 blood lysis reagents containing saponin, carbonate buffer, Triton X-100 and SPS. The type 3 blood lysis reagent solutions were prepared by combining 10 ml of a carbonate-bicarbonate buffer solution, prepared with a buffer concentration of 200 mM and a pH value were in the range of 9.5-10, with 10 ml of reagent solutions having SPS with a concentration ranging from 0-80 mg/ml, a saponin concentration of 60 mg/ml, and 3% Triton X-100 w/v, to obtain the type 3 blood lysis reagent solutions having a volume of 20 ml, an SPS concentration ranging from 0-40 mg/ml, a saponin concentration of 30 mg/ml, a Triton X-100 concentration of 1.5% w/v, and a buffer concentration of 100 mM. After mixing 5 ml of each blood lysis reagent with 3 ml of whole blood, the SPS concentration ranged from 0-25 mg/mL, the saponin concentration was 18.75 mg/mL, the Triton X-100 concentration was 0.94% w/v, and the effective buffer concentration was 62.5 mM. Spiked phosphate buffer samples were prepared according to the method of Example 3. Centrifugal separation and real time RT-PCR was subsequently performed according to the methods provided in Examples 6 and 7 below for spiked phosphate buffer samples as spiked controls and spiked whole blood samples, respectively. The threshold cycle value ($C_T$ value; i.e. the number of the PCR cycle after which the assay signal increases above a noise threshold value) was measured, and the difference in $C_T$ values, $\Delta C_T$, was determined based on the difference between the spiked whole blood $C_T$ value and the spiked control $C_T$ value.

Figure 16E:
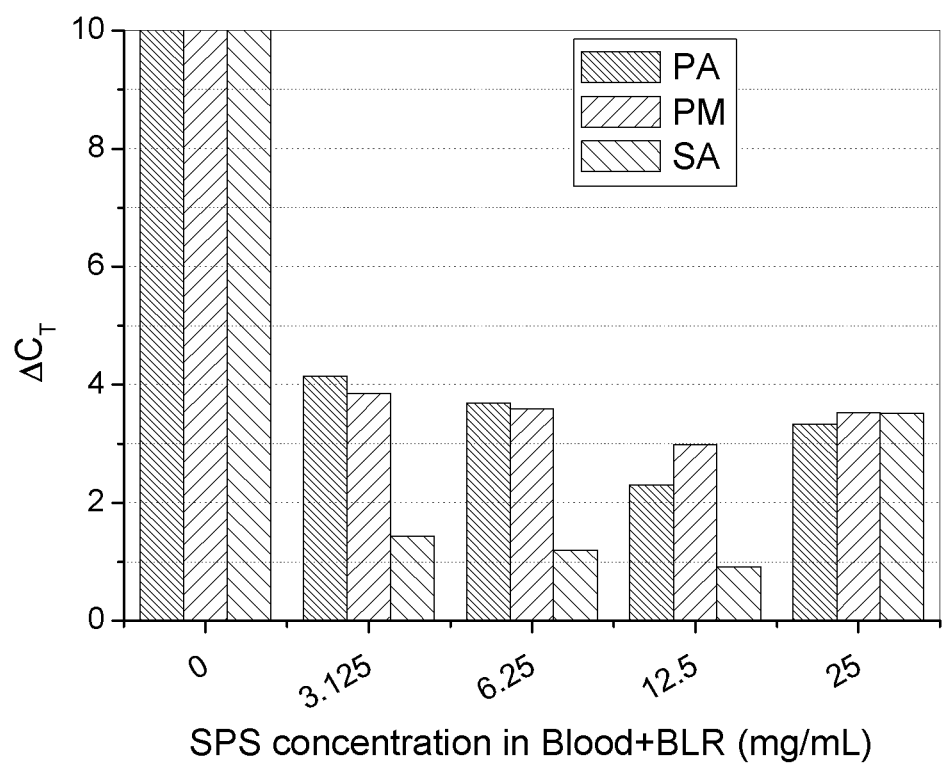
FIG. 16E plots the dependence of $\Delta C_T$ on SPS concentration for different bacterial species after contacting whole blood samples with a type 3 blood lysis reagent containing a different concentration of saponin, SPS, a carbonate-bicarbonate buffer and Triton X-100, performing centrifugal separation and concentration, heat lysis and real-time RT-PCR.

As shown in FIG. 16E, the $\Delta C_T$ values for all three microbial species were less than 5 for final (post-mixed) SPS concentrations of 3.125 mg/ml and greater. No detectable signal was obtained for the samples contacted with the blood lysis reagent absence of SPS. Therefore, these results shown that in the absence of SPS, detection of rRNA via real time RT-PCR is impaired, possibly due to the caking phenomenon described above.

While many of the example embodiments described herein employ Triton X-100 (known, for example, as polyethylene glycol p-(1,1,3,3-tetramethylbutyl)-phenyl ether, Octyl phenol ethoxylate, Polyoxyethylene octyl phenyl ether, 4-Octylphenol polyethoxylated, and t-Octylphenoxypolyethoxyethanol) as a non-ionic surfactant, it will be understood that a type 3 blood lysis reagent suitable for the lysis of blood components and the preservation of intact microbial cells may include a wide range of non-ionic surfactants. Non-limiting examples of suitable non-ionic surfactants include, but are not limited to, alkylglycosides, Brij 35 (C12E23 Polyoxyethyleneglycol dodecyl ether) (15, 7), Brij 58 (CI 6E20 Polyoxyethyleneglycol dodecyl ether) (16), Genapol (13 to 19), alkyl N-methyl glucamide such as MEGA-8, -9, -10, octylglucoside (12,6), Pluronic F127, Triton X-100 (C14H22O(C2H4O)") (13,4), Triton X-114 (C24H4206) (12, 4), Tween 20 (Polysorbate 20) (16, 7) and Tween 80 (Polysorbate 80) (15) Nonidet P40 sodium deoxycholate, reduced Triton X-100 and or Igepal CA 630.

It has been observed by the present inventors that the type 3 blood lysis reagent formulation can be susceptible to foaming under various mixing and storage conditions in the absence of an antifoaming agent. Accordingly, in some example embodiments, the type 3 blood lysis reagent may further include an antifoaming agent. An antifoaming agent is preferably insoluble in the foaming medium, has a low surface tension to allow it to spread across the surface, and is capable of penetrating the foam air-liquid interface to destabilize and cause it to collapse. Furthermore, in automated applications involving fluid delivery within a cartridge, the antifoaming agent should either completely eliminate or substantially reduce foam formation. Additionally, during the blood lysis process, an ideal antifoaming agent will have minimal or no affinity towards microbial cells and remain suspended in the liquid as an emulsion. During separation (e.g. centrifugation or filtration), a phase separation should not form between the antifoaming agent and the rest of the blood lysis reagent due to the risk of the antifoaming agent collecting and entrapping the microbial cells.

The present inventors experimentally investigated two commercially available antifoaming formulations from Sigma Aldrich: Organic Antifoam 204 (Product Number A8311) and Silicone Antifoam SE-15 (Product Number A8582). Antifoam 204 ("AF204") contains 100% active components consisting of a mixture of non-silicone polypropylene-based polyether dispersion. AF204 was investigated by itself and in combination of polypropylene glycol ("PPG4000") having an average molecular weight of 4000 Da. The antifoaming agent SE-15 is a 10% emulsion w/v of active silicone polymer and non-ionic emulsifiers.

In the example below, various type 3 blood lysis reagent, with added antifoaming agents, were assessed according to three criteria: 1) foam height after vigorous shaking, 2) impact on microbial cell recovery (as per rRNA detection and amplification), and 3) medium-term stability. The type 3 blood lysis reagent solutions were prepared by combining 10 ml of carbonate-bicarbonate buffer solution, prepared with a buffer concentration of 200 mM and a pH value 9.5-10, with 10 ml of a solution having a concentration of 30 mg/ml of SPS, a saponin concentration of 60 mg/ml, 3% Triton X-100 w/v, and AF204, SE-15, PPG4000 or mixtures thereof, each with a concentration of 0.1 to 0.4% (v/w), to obtain the type 3 blood lysis reagent solutions having a volume of 20 ml, an SPS concentration of 15 mg/ml, a saponin concentration of 30 mg/ml, a Triton X-100 concentration of 1.5% w/v, a buffer concentration of 100 mM, and AF204, SE-15, PPG4000 or mixtures thereof, each with a concentration of 0.05 to 0.2% w/v.

Figures 17B, 17C:
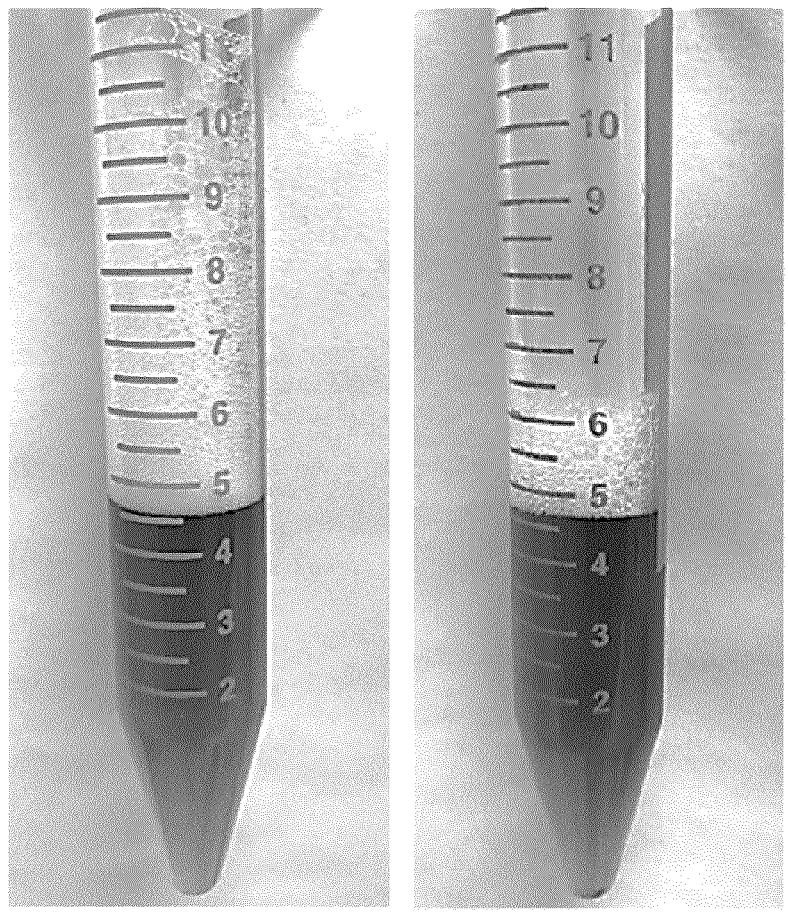
FIG. 17B presents images showing post-vortexing foam height for centrifuge tubes without (left) and with (right) antifoaming agent.
FIG. 17C is a table summarizing the time-dependence of foam height for tubes without (HR3) and with (HR5) an antifoaming agent.

The blood lysis reagent of 1 mL was distributed in 15 ml conical tubes and shaken vigorously for 10 seconds in 90° arcs and then set down in a tube rack where the foam height from the liquid surface can be observed and measured (see FIG. 17A). Without any antifoaming agent, the lysing reagent was observed to produce foam that is approximately 25 mm in height when shaken in the manner described above.

When using a non-silicone based antifoaming agent, the foam height decreased more effectively when AF204 was combined with PPG4000, ideally in a ratio of 10:1. However, upon continued shaking, the effect of the antifoam mixture diminished increasing the foam height from 3.5 mm after the first shake to 10 mm after subsequent shakes. The silicone-based emulsion, SE-15 was used by itself in concentrations of 0.05 to 0.2% (v/w) in 1 mL of the type 3 blood lysis reagent described above. The foam height dropped from 25 mm in the untreated sample, to 2.5 mm with 0.05% (v/w) SE-15, and down to virtually no foam with 0.2% (v/w) SE-15.

The effect of the antifoaming agent SE-15 was observed to be persistent upon subsequent agitations of the blood lysis reagent. To further illustrate the antifoaming performance of SE-15, 5 mL each of the aforementioned type 3 blood lysis reagent with 0.05% (v/w) SE-15 (FIG. 17B, right) and the type 3 blood lysis reagent absent of an antifoaming reagent (FIG. 17B, left) in respective 15 mL centrifuge tubes were vortexed for 1 minute at maximum speed on a standard benchtop laboratory vortexer. The results of these experiments are summarized in FIGS. 17B and 17C. Immediately after vortexing, the blood lysis reagent with SE-15 (FIG. 17B, right and HR5 in FIG. 17C) had close to one fifth the foam height compared to the untreated blood lysis reagent. Within 20 seconds, the foam had almost entirely collapsed, while the foam in the untreated blood lysis reagent (FIG. 17B, left and HR3 in FIG. 17C) remained unchanged.

For evaluating the impact of the antifoaming agents on cell recovery, spiked phosphate buffer samples containing *Pseudomonas aeruginosa* (PA), *Proteus mirabilis* (PM), and *Staphylococcus aureus* (SA), prepared according to Example 3 below (with the exception that the microbial cells were spiked at concentrations of 200 CFU/ml instead of 100 CFU/ml), were mixed with various type 3 blood lysis reagents containing antifoaming agents (FIG. 17A). After mixing 1 ml of the blood lysis reagent with 1 ml of spiked phosphate buffer sample, the SPS concentration was 7.5 mg/mL, the saponin concentration was 15 mg/mL, the Triton X-100 concentration was 0.75% w/v, the buffer concentration was 50 mM, and the concentration of antifoaming agent (AF204, SE-15, PPG4000 or mixtures thereof) ranged from 0.0025 to 0.1% (w/v). Centrifugal separation and real time RT-PCR was subsequently performed according to the methods provided in Example 5. The $\Delta C_T$ value was determined by subtracting the $C_T$ value obtained in an experiment using a type 3 blood lysis reagent without an antifoaming agent from the measured $C_T$ values of the experiments using a type 3 blood lysis reagent with an antifoaming agent.

The results of the cell intactness experiments, shown in FIG. 17A, demonstrate that for both silicone and non-silicone based antifoaming agents, no significant increase in $C_T$ values were observed when compared to a type 3 reagent in the absence of an antifoaming agent. Indeed, for both antifoaming agents, the emulsion created by the antifoaming agent in the blood lysis reagent remained homogeneous throughout the blood lysis process, with no observable phase separation. Furthermore, in the case of SE-15, microscopic evaluation failed to observe any emulsion particles remaining in the final wash of the example centrifugation process, indicating that the agent is effectively removed and therefore unable to interfere with the downstream assay.

To evaluate the short-term stability of the type 3 blood lysis reagent on cell recovery, spiked phosphate buffer samples containing *Pseudomonas aeruginosa* (PA), *Proteus mirabilis* (PM), and *Staphylococcus aureus* (SA), prepared according to Example 3 below (with the exception that the microbial cells were spiked at concentrations of 200 CFU/ml instead of 100 CFU/ml), were mixed with various type 3 blood lysis reagents prepared with (HR5) or without (HR3) SE-15 as shown in FIG. 17D. The type 3 blood lysis reagent solutions having a volume of 20 ml, an SPS concentration of 15 mg/ml, a saponin concentration of 30 mg/ml, a Triton X-100 concentration of 1.5% w/v, a buffer concentration of 100 mM, and with or without 0.05% SE-15 (w/v) were prepared. After mixing 1 ml of the blood lysis reagent with 1 ml of spiked phosphate buffer sample, the SPS concentration was 7.5 mg/mL, the saponin concentration was 15 mg/mL, the Triton X-100 concentration was 0.75% w/v, the buffer concentration was 50 mM, and the concentration of SE-15 was 0.0025 (w/v). Sample preparation and real time RT-PCR was performed according to the methods provided in Example 5 below. Spiked phosphate buffer samples, prepared according to the method of Example 3 below, were also prepared for spiked control and subjected to real time RT-PCR according to the method of Example 4 below. The $\Delta C_T$ value, determined based on the difference between the spiked phosphate buffer sample $C_T$ value and the spiked control $C_T$ value, was employed as a proxy for microbial cell intactness. Short-term stability of the type 3 blood lysis reagent prepared in the presence of the antifoaming agents did not show any deterioration in cell recovery and antifoaming properties.

As mentioned above, Antifoam SE-15 is a commercial emulsion that consists of 10% silicon polymer and up to 5% of a non-ionic emulsifier. The silicon polymer is polydimethylsiloxane (general chemical formula: $(H_3C)_3[Si(CH_3)_2O]_nSi(CH_3)_3$, CAS Number: 63148-62-9), the emulsifier is polysorbate 65 (CAS Number: 9005-71-4) and the diluent is water. In general, the class of antifoaming agents compatible with the blood lysis reagent consist of a mixture of polydimethylsiloxane in concentrations between 10 and 30% in water in the presence of an oil-in-water emulsifier or mixture of emulsifiers that have an overall hydrophilic-lipophilic balance (HLB) value in between 8 and 15. Some examples of these emulsifiers include, but are not limited to, polyoxyethylene ether and sorbitan derivative based surfactants such as, but not limited to, polysorbate 85, polysorbate 60, polysorbate 60, polyoxyethylene nonylphenyl ethers, polyoxyethylene tridecyl ethers, polyethylene glycol octadecyl ethers and polyoxyethylene stearyl ethers.

The aforementioned experimental investigations demonstrate that effective separation, purification and concentration of a whole blood sample may be achieved by mixing a whole blood sample with a type 3 blood lysis reagent (for the selective lysis of blood and/or other eukaryotic cells) that includes, but is not limited to, saponin, SPS, a non-ionic surfactant, an alkaline buffer, and an optional antifoaming agent. As described above, the present inventors hypothesized that saponin, as a surfactant, may form a layer over the microbial cells without causing damage to the microbial cells, and that the surfactant layer generated by saponin may act as a protective layer in an alkaline environment, shielding the microbial cells from the otherwise deleterious effect of the high pH environment. This concept was nonetheless met with initial resistance by the inventors, who had a low expectation of success of this reagent combination due to an expected incompatibility of saponin with a high pH environment. Specifically, the inventors suspected that the hemolytic role of saponin, and the potential protective role of saponin described above, could be deleteriously affected by the degradation of saponin caused by the alkaline environment.

Saponin is typically obtained as an extract from the *Quillaja saponaria* Molina tree in South America and is composed of a complex mixture of over 30 structurally diverse glycosides differing by the nature of the polysaccharides attached to a common triterpenoid backbone. The major saponins, QS-7, QS-17, QS-18 and QS-21, represent up to 90% by weight of the total saponin content, and have been the most well characterized in terms of their chemical structures, toxicity and hemolytic activity. When isolated, QS-17, QS-18 and QS-21 all cause hemolysis at approximately the same dose (7-25 μg/mL).

Saponin is weakly acidic and will exhibit a pH of between 4 to 5, depending on its purity, when dissolved in water at 20% concentration by weight. At a pH greater than 8, the main saponin compounds, QS-7, QS-17, QS-18 and QS-21 will undergo alkaline hydrolysis to generate "deacetylated saponins" DS-1 and DS-2. These deacetylated saponins exhibit approximately 10-fold lower hemolytic activity than their parent saponins (D. J. Pillion, J. A. Amsden, C. R. Kensil, J. Recchia "Structure—function relationship among *Quillaja* saponins serving as excipients for nasal and ocular delivery of insulin." J of Pharmaceutical Sciences, Vol 85, No. 5 1996, pages 518-524). At such elevated pH levels, the critical micelle concentration of the saponin mixture will also increase by ten-fold from 200 mg/L at pH 6.5 to 2000 mg/L at pH 10 (W-J Chen, L-C Hsiao, K K-Y Chen "Metal desorption from copper(II)/nickel(II)-spiked kaolin as a soil component using plant-derived saponin biosurfactant." Process Biochemistry, Vol. 43, No 5 2008, pages 488-498). Given this known degradation of saponins in an alkaline environment, and the associated reduction in hemolytic activity, the inventors were surprised by the success of the type 3 blood lysis reagent, as the effectiveness of the type 3 blood lysis reagent did not immediately degrade.

The present inventors performed a set of stability experiments to further investigate the degradation of saponin in the presence of the alkaline environment of the type 3 reagent. As explained below, these experiments investigated the stability of the type 3 blood lysis reagent from the dual perspectives of (i) hemolytic capability and (ii) microbial cell intactness, as determined via rRNA amplification.

In a first experiment designed to investigate the stability of saponin in an alkaline environment from a hemolysis capability perspective, saponin from Desert King International (Saponin-Ultra) was further purified by tangential flow filtration to give a solution with 197 mg/mL of total saponin that was >80% w/w by (HPLC) saponin content, with a low amount of polyphenol <1.5% (w/w) and polysaccharide <5% (w/w) impurities. The solution was diluted to a concentration of 30 mg/ml in one of three different buffers: (1) unbuffered (dissolved in water, final pH~4.3); (2) 60 mM sodium acetate buffer (final pH~4.9); and (3) 100 mM sodium carbonate buffer (final pH~9.8). The saponin samples were stored in sealed vials at room temperature and then tested for hemolysis activity using the following procedure. The saponin solutions were diluted to a concentration of 4 mg/mL in 0.9% w/v NaCl in 1 mM phosphate buffer (pH 7.4) (PBS). In separate 2 mL polypropylene tubes, serial dilutions of 200 µL were prepared for each saponin solution from 1280 µg/mL to 5 µg/mL in PBS. The positive control was 200 µL of 1% Triton X-100 w/v in PBS, while the negative control was 200 µL of PBS alone. To each sample and control was added 200 µL of 4% v/v Sheep Red Blood Cells (Innovative Research IC100-0210) in PBS. The polypropylene tubes were capped and then incubated at room temperature for 2 hours on a rotisserie shaker. The tubes were centrifuged at 3000 RPM for 5 minutes and then 50 µL from each supernatant diluted with 150 µL of PBS inside a 96-well assay plate.

Hemolysis was investigated by measuring the absorbance of each sample at 540 nm in a UV/visible microplate reader. A dose-response curve was generated from the absorbance values over the various dilutions from where the HC50 values (concentration of saponin to reach 50% complete hemolysis) of each saponin sample was calculated. The hemolysis test was performed once immediately after the saponin was diluted in the different buffers and again after 23 days of storage at room temperature in order to investigate saponin's short term stability.

FIGS. 18A and 18B show the dose response curves of each saponin solution taken at Day 0 and Day 23, respectively, and FIG. 18C presents the calculated HC50 values derived from the curves. After the first day the hemolysis activities of each saponin at low and high pH values are almost identical (HC50 values at approximately 36 µg/mL). After 23 days, the saponins stored in acidic buffers (pH<5) show no significant change in their dose-response and HC50 values (between 39 and 38 µg/mL), whereas the saponin at alkaline buffer (pH~10) shows a 2-fold loss of hemolytic activity over the same period (89 µg/mL).

The loss of this hemolysis activity is due to the slow alkaline hydrolysis of the highly active saponins QS-7, QS-17, QS-18 and QS-21 to the less active "deacetylated saponins" DS-1 and DS-2. However, at the higher pH, the saponins appear to be mostly intact at least within the typical time period of performing lysis with a blood lysis reagent (e.g. approximately 5 minutes), as indicated by the hemolysis activity at day 0.

The discussion above illustrate the instability of saponin at high pH medium in terms of the hemolysis efficiency. A second set of experiments were performed to investigate the effect of the alkaline pH and the non-ionic surfactant on ability of saponin to preserve microbial cell intactness. As in some of the preceding example experiments, rRNA amplification was employed as a proxy for cell intactness following blood lysis and separation of microbial cells, with intactness quantified by $\Delta C_T$. Experiments were performed by monitoring the $\Delta C_T$ value over time when the carbonate buffer is either kept separately or together with the rest of the components of the blood lysis reagent. Experiments were performed using two types of 3 blood lysis reagent.

A first type 3 blood lysis reagent was prepared by combining 20 ml of a carbonate-bicarbonate buffer solution, prepared with a buffer concentration of 200 mM and a pH value of 10, with 10 ml of reagent solutions having SPS with a concentration of 30 mg/ml, a saponin concentration of 60 mg/ml, 3% Triton X-100 w/v, and a concentration of SE-15 of 0.1% w/v to obtain the type 3 blood lysis reagent solutions having a volume of 20 ml, an SPS concentration of 15 mg/ml, a saponin concentration of 30 mg/ml, a Triton X-100 concentration of 1.5% w/v, a concentration of SE-15 0.05% w/v, and a buffer concentration of 100 mM. A second reagent was prepared based on a type 3 blood lysis reagent, but without the addition of the buffer, such that a type 3 blood lysis reagent could be obtained by combining this reagent with a carbonate-bicarbonate buffer prior to use, thereby avoiding degradation of the saponin during storage. This second reagent had an SPS concentration of 30 mg/ml, a saponin concentration of 60 mg/ml, a Triton X-100 concentration of 3% w/v, a concentration of SE-15 of 0.1% w/v.

After one week of storing the first reagent (having all reagent components pre-mixed prior to storage) and the second reagent (stored absent of the carbonate-bicarbonate buffer) at room temperature, the second reagent was mixed with an equal volume of 200 mM carbonate buffer (pH 10), thereby providing a post-mixed type 3 blood lysis reagent having an SPS concentration of 15 mg/ml, a saponin concentration of 30 mg/ml, a Triton X-100 concentration of 1.5% w/v, a concentration of SE-15 of 0.05% w/v. The pre-mixed and post-mixed type 3 blood lysis reagents were then contacted with (i) spiked whole blood samples with a volume of 3 ml containing *Pseudomonas aeruginosa* (PA), *Proteus mirabilis* (PM), and *Staphylococcus aureus* (SA), prepared according to Example 2 below, and (ii) spiked phosphate buffer samples containing *Pseudomonas aeruginosa* (PA), *Proteus mirabilis* (PM), and *Staphylococcus aureus* (SA), prepared according to Example 3 below. After mixing 5 ml of each blood lysis reagent with 3 ml of spiked phosphate buffer or spiked whole blood respectively, the saponin concentration was 18.75 mg/mL, the SPS concentration was 9.375 mg/mL, the Triton X-100 concentration was 0.94% w/v, the concentration of SE-15 was 0.03% w/v and the effective buffer concentration was 62.5 mM. Centrifugal separation and real time RT-PCR was subsequently performed according to the methods provided in Examples 7 below for both spiked phosphate buffer samples and spiked whole blood samples. Spiked phosphate buffer samples, prepared according to the method of Example 3 below, were also prepared for spiked control and subjected to real time RT-PCR according to the method of Example 6 below.

The threshold cycle value ($C_T$ value; i.e. the number of the PCR cycle after which the assay signal increases above a noise threshold value) was measured, and the difference in $C_T$ values, $\Delta C_T$, was determined based on the difference between the spiked phosphate buffer $C_T$ value (FIG. 19A) or the spiked whole blood $C_T$ value (FIG. 19B) and the spiked control $C_T$ value. A separate set of experiments were made using a freshly prepared version of the first reagent to provide a reference for stability.

Figure 19A:
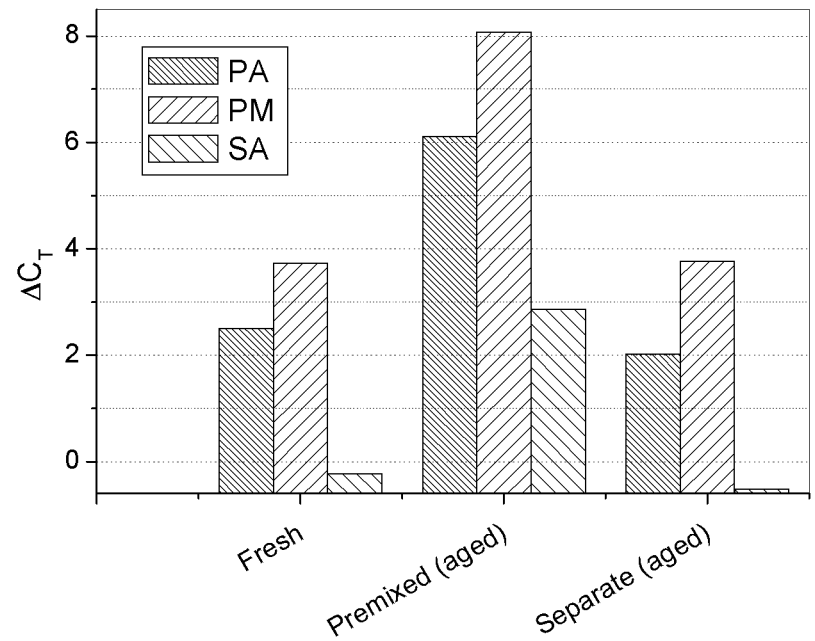
FIGS. 19A and 19B plot $\Delta C_T$ values for different bacterial species and three different storage conditions after contacting spiked phosphate buffer samples (FIG. 19A) or spiked whole blood samples (FIG. 19B) with a type 3 blood lysis reagent containing saponin, SPS, a carbonate-bicarbonate buffer and Triton X-100, performing centrifugal separation and concentration, heat lysis and real time RT-PCR.
Figure 19B:
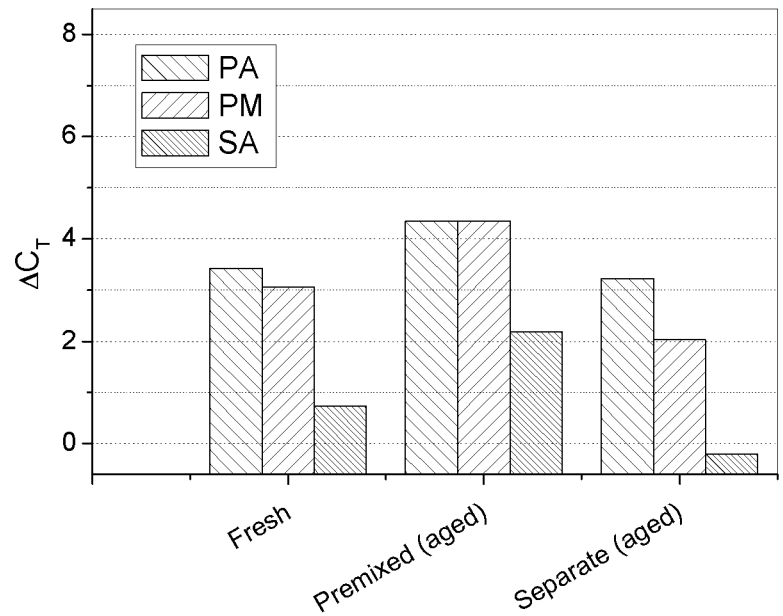

The results are presented in FIGS. 19A and 19B for spiked phosphate buffer samples and spiked whole blood samples, respectively. As it is observed, over a week, the performance of the type 3 blood lysis reagent, with saponin premixed with the buffer system and thereby stored at high pH, degrades such that the $\Delta C_T$ values increase by 3-8 cycles. These experimental results show that while saponin, when stored in a high-pH environment, appears to significantly degrade in terms of its protective role during selective lysis on the timescale of approximately one week for the case of use with a spiked weak phosphate buffer, this the degradation does not appear to have as significant an impact when the blood lysis reagent is mixed with blood (i.e. less increase in $\Delta C_T$ was observed).

The experimental results presented above demonstrate that while the protective effectiveness of saponin is not compromised immediately or soon after mixing with a whole blood sample (e.g. up to one day after mixing), improved reagent performance can be achieved by performing long term storage (e.g. storage over days, weeks or months) with the saponin component separated from the basic component of the alkaline buffer. For example, one component of a type 3 blood lysis reagent may be formulated to contain saponin in a neutral or acidic environment that is converted to an alkaline pH upon mixing one or more additional reagent components. These reagent components may be stored in a liquid format, dry format, or combination or liquid and dry format (with one or more reagent components being stored in a liquid format and one or more other reagent components being stored in a dry format). These reagent components may be mixed prior to performing blood lysis of a blood sample. For example, the reagent components may be mixed to form the type 3 blood lysis reagent immediately prior to contacting a blood sample (e.g. within seconds or minutes of contacting the blood sample), or alternatively the reagent components may be mixed to form the type 3 blood lysis reagent with a suitable delay (e.g. hours) prior to contacting a blood sample, where the delay is determined (e.g. through a series of experiments assessing the dependence of microbial cell intactness on delay) to maintain a sufficient intactness of microbial cells during the blood lysis process.

In one example implementation involving the separation of reagent components, a first reagent comprising alkaline salt (such as sodium carbonate or potassium carbonate) can be stored separately from a second reagent, containing saponin and buffered between pH 3.5 and 5.5 (e.g. with acetate, citrate, ascorbate, benzoate or malate buffer). The first reagent can be stored in a dry format, such that it is solubilized upon mixing with the second reagent. Upon sufficient dissolution of the first reagent by the second reagent (e.g. via mixing), the resulting blood lysis reagent can be contacted with the blood sample.

The separation of the alkaline component of a type 3 blood lysis reagent according to the aforementioned example can be achieved provided that the components of the first reagent, in particular saponin, are stable for prolonged periods under mildly acidic conditions in the presence of an appropriate acidic pH buffer at room temperature. Furthermore, the first and second reagents should be configured such that the proper proportion of solid alkaline relative to acidic buffer can be dissolved such that the final alkaline pH level of the mixed type 3 blood lysis reagent, as well as the desired effective buffer concentration can be achieved. It is also beneficial to select the alkaline salt such that it can dissolve on a sufficiently rapid timescale, does not hinder the fluid flow (e.g. when employed in an automated process, where channels or valves could otherwise be blocked) nor remain present as undissolved particulates that can impair the recovery of intact microbial cells.

In selected non-limiting example implementations, example alkaline salts that can be used to form a suitable first reagent include sodium carbonate and potassium carbonate due to their relatively high solubility in water (31 g/100 mL and 111 g/100 mL respectively at 25° C.), which allows them dissolve easily in the presence of the second reagent. Such salts can be prepared as highly concentrated aqueous solutions which can enable dispensing of the alkaline reagent as liquids, which can then be dried to leave a solid reagent (the first reagent in the present example implementation). In another example implementation, the first reagent can be formed (e.g. pressed) into small solid pellets (e.g. 2-4 mm in diameter) that can rapidly break apart and dissolve when combined with the second (liquid phase) reagent. The first reagent and second reagent can be formed with respective compositions such that, when mixed, the target pH for the type 3 blood lysis reagent is obtained and/or a maximum pH (and/or buffer concentration) is not exceeded.

The following example provides an example method for generating two reagents that can be stored separately and subsequently mixed to obtain a type 3 blood lysis reagent, in order to maintain saponin activity during storage. The first reagent is configured to provide an alkaline solution, such as sodium carbonate, and is kept separate from the second reagent prior to hemolysis, and may be provided as a liquid, or as a solid that can be subsequently dissolved upon mixing with the second reagent. In the present non-limiting example implementation, the first reagent includes sodium carbonate or potassium carbonate and is stored in a solid phase. The second (liquid phase) reagent includes saponin and is buffered with a neutral or acidic pH, such as a pH in the range of 3.5 to 6.5, 3.5 to 8, or 4 to 5.

In order to determine suitable relative amounts of the first reagent and the second reagent in order to obtain a desired pH after mixing the two reagents, the second reagent was prepared in a mildly acidic buffer and then titrated with the first reagent that was a sodium carbonate solution. Prior to the addition of the acidic buffer and the sodium carbonate titrant, the second reagent (4.5 mL) included Triton X-100 with a concentration of 1.67% by volume, SPS with a concentration of 22.2 mg/mL), saponin with a concentration of 33.3 mg/mL, and the antifoaming agent SE-15 with a concentration of 0.056% (v/w). The second reagent was then buffered with and either sodium acetate (pH 5) or sodium citrate (pH 4.5 and pH 5) in varying amounts.

Figure 20A:
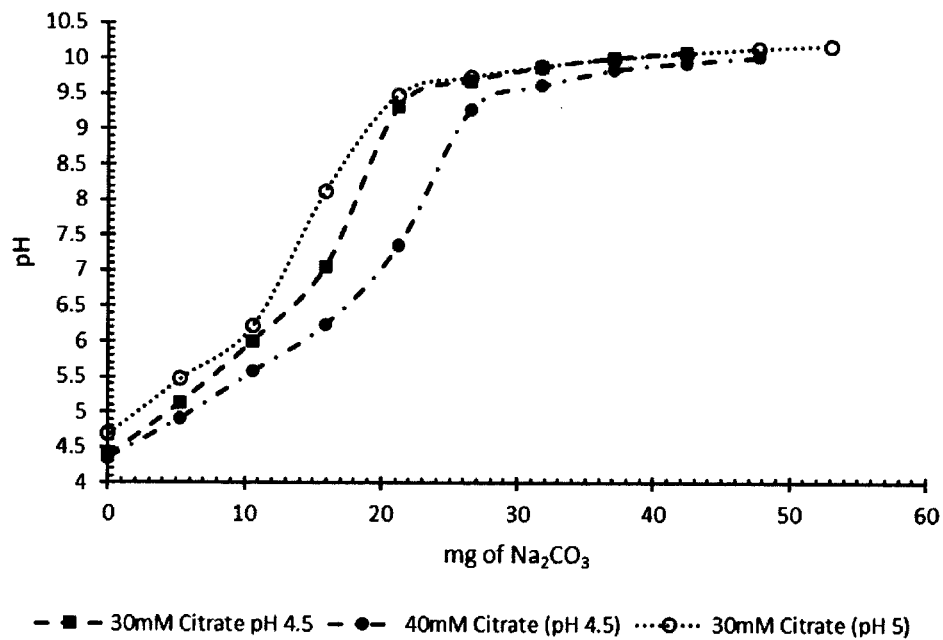
FIGS. 20A and 20B plot titration curves indicating the dependence of the measured pH of $Na_2CO_3$ for various citrate buffer strengths (FIG. 20A) and acetate buffer strengths (FIG. 20B).
Figure 20B:
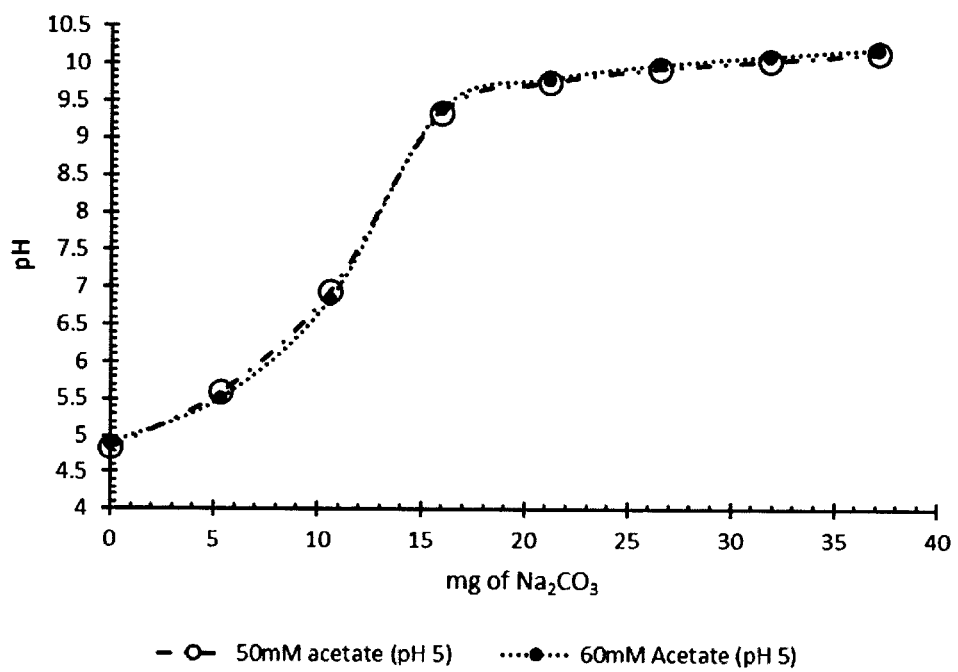

FIGS. 20A and 20B plot the measured pH changes when titrating the second reagent, containing varying amounts of sodium citrate and sodium acetate, respectively, with a first reagent provided as a solution of sodium carbonate (1 molar). In each case, a pH that is between 9.5 and 10.0 is targeted, such that the total concentration of acetate/citrate with sodium carbonate is between 80 and 100 mM. As shown in the figures, the reagent mixture remains weakly buffered at lower pH levels upon the first few additions of the sodium carbonate solution, but between pH 7 and 9, there is a rapid rise in pH as the carbonate dominates the new buffering system.

In the case of the citrate buffer (shown in FIG. 20A), the amount of sodium carbonate that is needed to reach pH 9 is dependent on the initial pH of the second reagent and the concentration of the citrate. For instance, with 40 mM of citrate at pH 4.5, at least 27 mg of sodium carbonate (equivalent to a buffer concentration of almost 50 mM) is required to increase the pH above 9, whereas with 30 mM of citrate, 21 mg of sodium carbonate (or a buffer concentration of approximately 40 mM) is sufficient to reach the same pH level. However, the 40 mM sodium citrate (pH 4.5) and 27 mg sodium carbonate combination provides a higher buffering concentration which is expected to be more resistant to a pH change caused by exposure to blood.

In the case of the acetate buffer (shown in FIG. 20B), the dependence on initial acetate concentration is less pronounced than with the citrate buffer, which allows for easier targeting the desired buffer capacity without effecting the pH.

The example titration curves shown in FIGS. 20A and 20B can be employed to determine the amount of solid sodium carbonate that is needed in the first reagent in order reach a desired pH level. For example, if 40 mM of citrate buffer at pH 4.5 is used, then in order to obtain a total buffer concentration 100 mM at approximately pH 9.6 to 9.7, 32 mg of sodium carbonate powder will be needed in the first reagent.

The present inventors have found that the effectiveness of the type 3 blood lysis reagent in achieving selective blood cell lysis while preserving the intactness of microbial cells and avoiding the generation of residual blood debris can be dependent on how thoroughly the blood lysis reagent is mixed with the sample. Non-limiting examples of effective methods of mixing include, but are not limited to, vortexing, stirring, magnetic bead-based mixing and transport between interconnected chambers. A suitable degree of mixing, and a suitable time during for mixing, can be experimentally determined by varying the mixing parameters and time duration and performing experiments that investigate microbial cell intactness (e.g. via a proxy assay such as rRNA amplification) and/or investigate the residual blood debris, selecting mixing parameters that achieve sufficient cell intactness and/or reduction or elimination of residual blood debris. The present inventors have found that in the example case of the lysis of blood cells, lysis occurs during the mixing operation provided that sufficient mixing is performed. For example, when performing mixing by vortexing or transport between fluid chambers, a suitable mixing time is in range of 30 seconds to 2 minutes.

While many of the example embodiments described herein employ centrifugation to achieve microbial cell separation, it will be understood that the present blood lysis reagent compositions and associated methods may be employed to perform selective lysis of blood components and/or other eukaryotic cells in combination with other microbial cell separation methods, such as, but not limited to filtration, immunomagnetic separation, and other separation techniques such as microfluidic-based separation.

Moreover, while the blood lysis reagents described herein are shown to be effective for the selective lysis of blood cells in blood samples, it will be understood that the blood lysis reagents described herein, and variations thereof, may be applied to a wide variety of sample types, and may be effective for the selective lysis of additional types of eukaryotic cells other than blood cells. For example, the cell lysis reagents disclosed herein (which in some example embodiments may be referred to as "eukaryotic cell lysis reagents") may be employed for the lysis of eukaryotic cells (blood cells or other eukaryotic cells) in samples such as, but not limited to, lymph fluid, cerebrospinal fluid, sputum, saliva, and homogenized tissue suspensions (e.g. for the lysis of non-microbial endogenous cells that reside in bodily fluids or other samples obtained from eukaryotic organisms).

As noted above, as per the inclusion of blood culture samples within the definition of a "blood sample", in some example embodiments, a type 3 blood lysis reagent may be employed for the extraction of intact microbial cells from a blood culture sample, such as a positive blood culture sample or a mid-culture blood culture sample. One may suspect that a type 1 blood lysis reagent would be the most appropriate blood lysis reagent choice for the extraction of intact microbial cells. For example, a type 1 blood lysis reagent may appear to be preferable because the combination of saponin and SPS generally do not damage bacterial cells. Furthermore, the blood content in a blood culture bottle is typically already diluted at least by a factor of four, and as a result of this dilution, the relative amount of blood cell debris in a positive blood culture sample after exposure to a type 1 blood lysis reagent is expected to be approximately one quarter of the blood cell debris present in a whole blood sample having similar volume after exposure to a type 1 blood lysis reagent. One may therefore reason that in view of this reduction in blood cell debris, a type 1 reagent may be suitable for processing blood culture samples.

However, as shown below, experimental observations made by the present inventors indicate that the higher dilution of a blood culture sample does not necessarily translate to a greater ease of removing blood cell debris, and that a type 3 blood lysis reagent is preferable for processing blood culture samples.

Experimental Study of the Effect of Blood Lysis Reagent Type on Post-Centrifugation Residue for Positive Blood Culture Samples The present experimental study was performed to investigate the effect of different types of blood lysis reagent compositions on the residual debris that is present after exposure to a positive blood culture sample. Positive blood culture sample inoculated with *Escherichia coli* was prepared using the method of Example 10. Samples with volumes ranging from 1 ml to 5 mL were treated according to the method of Example 11 using either type 1 or type 3 blood lysis reagents. In the case of a type 1 blood lysis reagent, upon mixing the type 1 blood lysis reagent with the positive blood culture sample, the concentration of saponin and SPS were 37.5 mg/mL and 7.5 mg/mL, respectively, irrespective of sample volume. In the case of a type 3 blood lysis reagent, upon mixing the type 3 blood lysis reagent with the positive blood culture sample, the concentration of saponin, SPS, carbonate-bicarbonate buffer (pH 10) were 17.5 mg/mL, 7.5 mg/mL, 25 mM (effective buffer concentration), respectively, irrespective of sample volume.

Figure 21A:
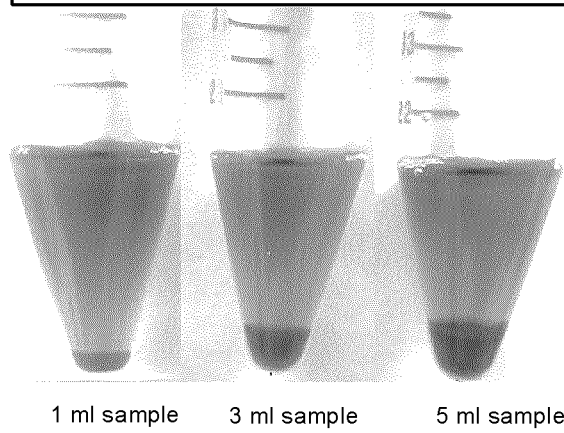
FIG. 21A shows images of centrifuge tubes after contacting positive blood culture samples with a type 1 blood lysis reagent containing saponin and SPS by convective mixing, followed by two centrifugal washing steps.
Figure 21B:
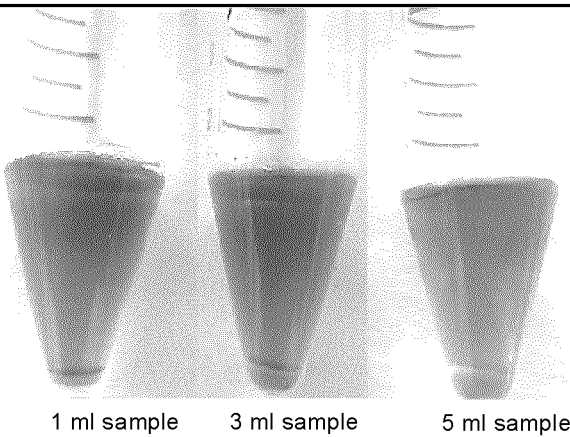
FIG. 21B shows images of centrifuge tubes after contacting positive blood culture samples with a type 3 blood lysis reagent containing saponin, SPS, and a carbonate-bicarbonate buffer by convective mixing, followed by two centrifugal washing steps.

FIGS. 21A and 21B show images of the of centrifuge tubes after performing hemolysis of the positive blood culture samples for type 1 and type 3 reagents, respectively, for the positive blood culture sample volumes ranging from 1 ml to 5 ml.

As shown in FIG. 21A, after contacting a positive blood culture sample with a type 1 blood lysis reagent, the blood debris, which are not fully digested by the type 1 blood lysis reagent, sediment along with microbial cells during centrifugation, forming a viscous cake that includes both the microbial cells and the blood cell debris in a complex network.

This cell-debris cake is not easily disrupted during automated centrifugal wash cycles and large amounts of blood cell debris remain when the washed microbial cells are resuspended, which may impact the performance of downstream processes (such as assays).

In stark contrast, as shown in FIG. 21B, after contacting a positive blood culture sample with a type 3 blood lysis reagent, the blood debris are digested in the presence of the elevated pH, and the resulting precipitate that is obtained after centrifugation is composed almost entirely of microbial cells. The clean microbial-cell precipitate can be readily seen in FIG. 21B, which shows a white precipitate that differs significantly from the viscous and dark cake that is formed using the type 1 blood lysis reagent. It is also readily apparent that the amount of precipitate is significantly reduced in the case of the type 3 blood lysis reagent, owing to the absence of the blood cell debris. The high purity microbial cell precipitate that is obtained via processing with a type 3 blood lysis reagent and which can be readily resuspended is expected to facilitate downstream assays with improved performance due to the absence of interfering effects that would otherwise be caused by residual blood cell debris.

It is noted that while the preceding example demonstrates the benefit of a type 3 blood lysis reagent for centrifugally processing a blood culture sample to obtain a microbial cell precipitate that is substantially free of blood cell debris, it is expected that the use of a type 3 blood lysis reagent for the processing of blood culture samples will also be beneficial for other separation modalities, such as filtration. Furthermore, it is expected that the improved digestion and viscosity of samples processed via a type 3 blood lysis reagent will facilitate automated transport-based mixing in a fluidic cartridge, in which mixing is achieved by flowing a liquid from one fluidic channel or fluidic chamber to another fluidic channel or chamber, and vice versa, optionally repeating this process one or more times.

Experimental Study Demonstrating Direct MALDI from Positive Blood Culture Using Type 3 Blood Lysis Reagent As noted above, the clean microbial cell precipitate that is obtained after treating a positive blood culture sample with a type 3 blood lysis reagent can facilitate the performing of subsequent assay steps, such as identification assays, with the absence of, or reduction of, additional sample preparation steps. The present inventors performed the following experiments to demonstrate the ability to perform MALDI directly on microbial cells that are obtained by performing separation and purification of positive blood culture samples after an initial blood cell lysis step using a type 3 blood lysis reagent, without requiring a subculture step. Three example type 3 reagents were prepared, each having different example compositions, such that after mixing 1 mL of positive blood culture sample with an equal volume of type 3 blood lysis reagent, the concentrations of the individual ingredients were as follows:

Example Type 3 Blood Lysis Reagent 1: The concentration of saponin, SPS, Triton X-100, and the effective concentration of the carbonate-bicarbonate buffer (pH 10), after mixing the blood lysis reagent with a positive blood culture sample, were 17.5 mg/mL, 10 mg/mL, 0.75%, and 50 mM, respectively.

Example Type 3 Blood Lysis Reagent 2: The concentration of saponin, SPS, Triton X-100, and the effective concentration of the carbonate-bicarbonate buffer (pH 10), after mixing the blood lysis reagent with a positive blood culture sample, were 17.5 mg/mL, 10 mg/mL, 0%, and 50 mM, respectively.

Example Type 3 Blood Lysis Reagent 3: The concentration of saponin, SPS, Triton X-100, and the effective concentration of the carbonate-bicarbonate buffer (pH 10), after mixing the blood lysis reagent with a positive blood culture sample, were 17.5 mg/mL, 10 mg/mL, 0%, and 25 mM, respectively.

Positive blood culture samples containing *Staphylococcus aureus, Escherichia coli* or *Pseudomonas aeruginosa* were prepared according to the method of Example 10. Centrifugal separation was subsequently performed according to the methods provided in Example 12, with 4 wash cycles being employed. The bacterial cells obtained in the suspension were subsequently tested by MALDI (VITEK® MS instrument) for identification according to the procedure of Example 16.

FIG. 21C illustrates the measured dependence of identification by MALDI (VITEK-MS-ID) of *Staphylococcus aureus, Escherichia coli* or *Pseudomonas aeruginosa* from positive cultured blood samples on the composition of a type 3 blood lysis reagent. All three bacterial species were correctly identified for the cases of all example type 3 blood lysis reagent compositions. The results illustrate that a wide range of compositions of the components of a type 3 blood lysis reagent may be employed for accurate and direct identification from blood culture samples via MALDI.

In the present experimental demonstration, 4 wash cycles were employed during cell separation. It will be understood that the use of 4 wash cycles is not generally necessary, and a larger or smaller number of wash cycles may be employed. For example, another experiment was performed to illustrate that a fewer number of washes cycles provide sufficient sample purity for running high performance identification by MALDI. Type 3 blood lysis reagent solutions was prepared by combining 10 ml of a carbonate-bicarbonate buffer solution prepared with a buffer concentration of 100 mM at pH of 10 with 10 ml of a solution having a concentration of 30 mg/ml of SPS, a saponin concentration of 60 mg/ml to obtain reagent solutions having a volume of 20 ml, an SPS concentration of 15 mg/ml, saponin concentration of 30 mg/ml, a buffer concentration of 50 mM and pH values were in the range of 9.5-10. After mixing 1 ml of the blood lysis reagent with 1 ml the positive blood culture sample, the SPS concentration was 7.5 mg/mL, the saponin concentration of 15 mg/mL, the pH value was in the range of 9.2-9.6, and the effective buffer concentration was 25 mM. Positive blood culture samples containing *Klebsiella pneumoniae* were prepared according to the method of Example 10. Centrifugal separation was subsequently performed according to the methods provided in Example 12 below for positive blood culture sample employing different number of wash cycle. The bacterial cells in the suspension were tested by MALDI (VITEK® MS instrument) for identification according to the procedure of example 16. The results are presented in FIG. 21D.

As it is observed the results of using the cell suspension provided identification with high confidence level when at least 2 wash cycles were employed. These results demonstrate that for a given set of processing conditions (e.g. a specific example dilution factor per wash, a specific example composition of a type 3 blood lysis reagent, specific example blood culture bottle formulation, a specific example volume of positive blood culture sample, a specific example dilution of the positive blood culture sample by the type 3 blood lysis reagent, and a specific example analysis method for performing identification based on mass spectrometry data), a minimum of two wash steps were required in order to perform identification via MALDI. However, it will be understood that in other cases, the required number of wash steps may differ, and may be greater or lower than two. Moreover, as noted above, the present example methods are not intended to be limited to centrifugal based separation and other separation modalities, such as filtration, immunomagnetic separation and microfluidic-based separation may be employed in the alternative.

As was illustrated above, type 3 blood lysis reagents have been shown to sufficiently digest blood cells and prevent the formation of the viscous network that is otherwise obtained when using a type 1 blood lysis reagent. Therefore, according to several example embodiments of the present disclosure, a type 3 blood lysis reagent may be employed for the processing of blood culture samples, such as positive blood culture samples, in order to extract intact microbial cells for subsequent processing.

In view of the examples provided herein, a wide variety of example compositions of blood lysis reagents, and methods of performing the selective lysis of blood cells and/or other eukaryotic cells, are presently disclosed. In one example embodiment, a method of performing selective lysis of blood cells and/or other eukaryotic cells in a sample, while preserving the intactness of one or more microbial cells in the sample, may be performed by contacting the sample with a blood lysis reagent containing saponin, SPS, an alkaline buffer and a non-ionic surfactant, mixing the sample with the blood lysis reagent, incubating the mixture for a sufficient time to achieve lysis of the blood and/or eukaryotic cells within the sample, and separating the microbial cells.

In one example embodiment, the blood lysis reagent may have a composition such that after the blood lysis reagent is mixed with the sample, the concentration of saponin lies between 3 and 60 mg/ml. In other example embodiments, the concentration of saponin in the final mixture may range between 10-30 mg/ml. It will be understood that a suitable concentration of saponin may vary depending on one or more factors, such, as, but not limited to, the types of microbial cells for which preservation of intactness during separation is desired, the pH and/or effective buffer concentration in the final mixture, and the type of sample and quantity of sample. It will be understood that a suitable saponin concentration range can be determined, for a given set of conditions, by following the experimental methods described herein, in order to investigate the effect of saponin concentration on one or more performance metrics, such as, but not limited to, blood lysis efficiency, quantity of residual blood cell debris, and microbial cell intactness.

In one example embodiment, the blood lysis reagent may have a composition such that after the blood lysis reagent is mixed with the sample, the concentration of SPS lies between 1.5 and 50 mg/ml. In other example embodiments, the concentration of SPS in the final mixture may range between 5-20 mg/ml. It will be understood that a suitable concentration of SPS may vary depending on one or more factors, such, as, but not limited to, the types of microbial cells for which preservation of intactness during separation is desired, the pH and/or effective buffer concentration in the final mixture, and the type of sample and quantity of sample. It will be understood that a suitable SPS concentration range can be determined, for a given set of conditions, by following the experimental methods described herein, in order to investigate the effect of SPS concentration on one or more performance metrics, such as, but not limited to, blood lysis efficiency, quantity of residual blood cell debris, and microbial cell intactness.

In one example embodiment, the blood lysis reagent may have a composition such that after the blood lysis reagent is mixed with the sample, the concentration of non-ionic surfactant lies within 0-3% w/v. In other example embodiments, the concentration of non-ionic surfactant in the final mixture may range between 0.5-2%. It will be understood that a suitable concentration of non-ionic surfactant may vary depending on one or more factors, such, as, but not limited to, the types of microbial cells for which preservation of intactness during separation is desired, the pH and/or effective buffer concentration in the final mixture, the type of sample and quantity of sample. It will be understood that a suitable non-ionic surfactant concentration range can be determined, for a given set of conditions, by following the experimental methods described herein, in order to investigate the effect of non-ionic surfactant concentration on one or more performance metrics, such as, but not limited to, blood lysis efficiency, quantity of residual blood cell debris, and microbial cell intactness.

In one example embodiment, the blood lysis reagent may have a composition such that after the blood lysis reagent is mixed with the sample, the pH lies within a range of 7.8-10. In other example embodiments, the pH of the final mixture may range between 8.2-9.5. In other example embodiments, the pH of the final mixture may lie within a range bounded by an upper pH value of 10, 9.9, 9.8, 9.7, 9.6 or 9.5, and bounded by a lower pH value of 8.0, 8.2, 8.4, 8.5, 8.6, 8.7, 8.8, 8.9 and 9.0. In some example embodiments, the buffer concentration may be selected such that the effective buffer concentration lies in the range of 10-300 mM. In other example embodiments, the buffer concentration may be selected such that the effective buffer concentration lies in the range of 30-100 mM.

It will be understood that a suitable pH may vary depending on one or more factors, such, as, but not limited to, the types of microbial cells for which preservation of intactness during separation is desired, the effective buffer concentration in the final mixture, the initial pH of the blood lysis reagent prior to mixing with the sample, the type of sample and quantity of sample.

In some example embodiments, the blood lysis reagent may have a pH of 9-11 (or, for example, 9.5-10.5) and the buffer concentration (or buffer capacity) may be selected such that the pH, after mixing the blood lysis reagent with a sample, decreases to a final pH that is less than 10, less than 9.9, less than 9.8, less than 9.7, less than 9.6, or less than 9.5, and greater than 8.2, greater than 8.4, greater than 8.5, greater than 8.6, greater than 8.7, greater than 8.8, greater than 8.9, or greater than 9.0. Without intending to be limited by theory, it is suspected by the present inventors that an initial pH in the range of 9-11 can be beneficial for performing efficient digestion of blood cells, yet if such a high pH is maintained after lysis of the blood cells, the resulting high pH can negatively affect the intactness of some microbial cells (e.g. such as *Pseudomonas aeruginosa* and *Proteus mirabilis*).

It will be understood that a suitable final pH and/or effective buffer concentration range can be determined, for a given set of conditions, by following the experimental methods described herein, in order to investigate the effect of pH and/or buffer concentration range on one or more performance metrics, such as, but not limited to, blood lysis efficiency, quantity of residual blood cell debris, and microbial cell intactness.

In one example embodiment, the blood lysis reagent may further comprise an antifoaming agent comprising an emulsion of polydimethylsiloxane containing an appropriate non-ionic surfactant as an oil in water emulsifier and may have a composition such that after the blood lysis reagent is mixed with the sample, the concentration of the antifoaming agent emulsion lies within 0.005 to 1% (v/w). In other example embodiments, the concentration of antifoaming agent emulsion in the final mixture may range between 0.01 and 0.05%. It will be understood that a suitable concentration of antifoaming agent may vary depending on one or more factors, such as, but not limited to, the concentration of other components of the blood lysis reagent, the type of sample and quantity of sample. It will be understood that a suitable antifoaming agent composition and concentration can be determined, for a given set of conditions, by following the experimental methods described herein, in order to investigate the effect of antifoaming agent concentration and composition on one or more performance metrics, such as, but not limited to, a quantity of foam generated during automated operations involving the mixing and/or separation process, and the pressure required to deliver fluids.

In one example embodiment, a method of performing selective lysis of blood cells and/or other eukaryotic cells in a sample, while preserving the intactness of one or more microbial cells in the sample, may be performed by contacting the sample with a blood lysis reagent containing saponin, SPS, and an alkaline buffer (e.g. with example concentrations and a pH as per the preceding example ranges), mixing the sample with the blood lysis reagent, and separating the microbial cells. While the inclusion of a non-ionic surfactant is beneficial in many applications, it is not necessary to achieve selective lysis in some applications, such as applications that are less sensitive to the presence of residual debris, and/or applications that do not involve downstream molecular amplification.

In one example embodiment, a method of performing selective lysis of blood cells and/or other eukaryotic cells in a sample, while preserving the intactness of one or more microbial cells in the sample, may be performed by contacting the sample with a blood lysis reagent containing saponin and an alkaline buffer (e.g. with example concentrations and a pH as per the preceding example ranges), mixing the sample with the blood lysis reagent, and separating the microbial cells. While the inclusion of a non-ionic surfactant and SPS is beneficial in many applications, these components may not be necessary to achieve selective lysis in some applications, such as applications that are less sensitive to the presence of residual debris, and/or applications that do not involve downstream molecular amplification.

Although many of the example methods disclosed above involve the separation of microbial cells after forming a mixture of the blood lysis reagent and the sample, it will be understood that in other example embodiments, nucleic acid extraction may be performed using the mixture without separating the microbial cells from the mixture. For example, the mixture may be contacted with a solid phase suitable for extraction, such as, for example, magnetic beads coated with silica or an anionic exchange resin, in order to remove mammalian nucleic acids from the mixture, and the resulting mixture may then be subjected to a lysis step (e.g. chemical, mechanical, electrical or ultrasonic) such that the microbial cells are lysed. The resulting lysate may then be contacted with a suitable solid phase for the extraction of the nucleic acids released by the microbial cells.

As explained above, the blood lysis reagent may be provided as two or more reagents that can be stored separately and mixed prior to use, such that the saponin component of the blood lysis reagent is stored in an acidic environment that is separated from the alkaline component of the blood lysis reagent. In one example implementation, one or more of the reagents that are mixed to form the final blood lysis reagent may be stored in a solid phase.

Although the preceding examples have disclosed the utility of the present type 3 blood lysis reagents for performing lysis of blood cells and/or other eukaryotic cells, followed by separation of microbial cells and subsequent detection and/or identification of microbial cells via reverse-transcription rRNA amplification, it will be understood that this is but one example application of the reagent compositions and methods contemplated herein. In applications involving subsequent (downstream) detection of microbial cells, it will be understood that the detection of nucleic acids such as, but not limited to, DNA, rRNA, mRNA and tmRNA may be performed via amplification (such as, but not limited to, PCR, reverse transcription PCR, and isothermal amplification methods) or via non-amplification methods (such as hybridization assays and sequencing) or combinations thereof. In other example methods, detection may be performed via affinity reactions with the microbial cell surface, mass spectroscopy, infrared spectroscopy, microscopy, flow cytometry, and/or via the detection of volatile organics associated with the microbial cells, to name but a few alternative detection modalities.

Many of the example embodiments described above involve the processing of whole blood samples. For example, as described above, the composition of the blood lysis reagent can be selected such that whole blood volumes in excess of 1 ml, or even in excess of 5 ml, can be processed while preserving the intactness of microbial cells and avoiding the visible formation of blood debris upon centrifugation or filtration of the mixture of the whole blood sample and the blood lysis reagent followed by subsequent washing steps. However, it will be understood that the methods described herein may be adapted to a wide variety of sample types, including, but not limited to, lymph fluid, cerebrospinal fluid, urine, sputum, saliva, and homogenized suspensions such as stool and homogenized tissue samples.

Example and non-limiting composition ranges are now provided below for the processing of blood culture samples, such as positive blood culture samples and mid-culture samples. While the following example concentration ranges have been determined based on their suitability for facilitating the subsequent performance of MALDI, it will be understood that the concentration ranges provided below, and variations thereof, may be employed to perform blood cell lysis when other downstream assays or downstream processes are performed.

In one example embodiment, the blood lysis reagent may have a composition such that after the blood lysis reagent is mixed with the blood culture sample, the concentration of saponin lies between 0.75 and 60 mg/ml. In other example embodiments, the concentration of saponin in the final mixture may range between 2.5-30 mg/ml. It will be understood that a suitable concentration of saponin may vary depending on one or more factors, such, as, but not limited to, the types of microbial cells for which preservation of intactness during separation is desired, the pH and/or effective buffer concentration in the final mixture, and the concentration of microbial cells in the blood culture sample. It will be understood that a suitable saponin concentration range can be determined, for a given set of conditions, by following the experimental methods described herein, in order to investigate the effect of saponin concentration on one or more performance metrics, such as, but not limited to, blood lysis efficiency, quantity of residual blood cell debris, and microbial cell intactness.

In one example embodiment, the blood lysis reagent may have a composition such that after the blood lysis reagent is mixed with the blood culture sample, the concentration of SPS lies between 0.35 and 50 mg/ml. In other example embodiments, the concentration of SPS in the final mixture may range between 1.25-20 mg/ml. It will be understood that a suitable concentration of SPS may vary depending on one or more factors, such, as, but not limited to, the types of microbial cells for which preservation of intactness during separation is desired, the pH and/or effective buffer concentration in the final mixture, and the concentration of microbial cells in the blood culture sample. It will be understood that a suitable SPS concentration range can be determined, for a given set of conditions, by following the experimental methods described herein, in order to investigate the effect of SPS concentration on one or more performance metrics, such as, but not limited to, blood lysis efficiency, quantity of residual blood cell debris, and microbial cell intactness.

In one example embodiment, the blood lysis reagent may have a composition such that after the blood lysis reagent is mixed with the blood culture sample, the concentration of non-ionic surfactant lies within 0-3% w/v. In other example embodiments, the concentration of non-ionic surfactant in the final mixture may range between 0.16-2%. It will be understood that a suitable concentration of non-ionic surfactant may vary depending on one or more factors, such, as, but not limited to, the types of microbial cells for which preservation of intactness during separation is desired, the pH and/or effective buffer concentration in the final mixture, and the concentration of microbial cells in the blood culture sample. It will be understood that a suitable non-ionic surfactant concentration range can be determined, for a given set of conditions, by following the experimental methods described herein, in order to investigate the effect of non-ionic surfactant concentration on one or more performance metrics, such as, but not limited to, blood lysis efficiency, quantity of residual blood cell debris, and microbial cell intactness.

In one example embodiment, the blood lysis reagent may have a composition such that after the blood lysis reagent is mixed with the blood culture sample, the pH lies within a range of 7.8-10. In other example embodiments, the pH of the final mixture may range between 8.2-9.5. In other example embodiments, the pH of the final mixture may lie within a range bounded by an upper pH value of 10, 9.9, 9.8, 9.7, 9.6 or 9.5, and bounded by a lower pH value of 8.0, 8.2, 8.4, 8.5, 8.6, 8.7, 8.8, 8.9 and 9.0. In some example embodiments, the buffer concentration may be selected such that the effective buffer concentration lies in the range of 2.5-500 mM. In other example embodiments, the buffer concentration may be selected such that the effective buffer concentration lies in the range of 5-250 mM.

It will be understood that a suitable pH may vary depending on one or more factors, such, as, but not limited to, the types of microbial cells for which preservation of intactness during separation is desired, the effective buffer concentration in the final mixture, the initial pH of the blood lysis reagent prior to mixing with the blood culture sample, and the concentration of microbial cells in the blood culture sample.

In some example embodiments, the blood lysis reagent may have a pH of 9-11 (or, for example, 9.5-10.5) and the buffer concentration (or buffer capacity) may be selected such that the pH, after mixing the blood lysis reagent with a blood culture sample, decreases to a final pH that is less than 10, less than 9.9, less than 9.8, less than 9.7, less than 9.6, or less than 9.5, and greater than 8.2, greater than 8.4, greater than 8.5, greater than 8.6, greater than 8.7, greater than 8.8, greater than 8.9, or greater than 9.0. Without intending to be limited by theory, it is suspected by the present inventors that an initial pH in the range of 9-11 can be beneficial for performing efficient digestion of blood cells, yet if such a high pH is maintained after lysis of the blood cells, the resulting high pH can negatively affect the intactness of some microbial cells (e.g. such as *Pseudomonas aeruginosa* and *Proteus mirabilis*).

It will be understood that a suitable final pH and/or effective buffer concentration range can be determined, for a given set of conditions, by following the experimental methods described herein, in order to investigate the effect of pH and/or buffer concentration range on one or more performance metrics, such as, but not limited to, blood lysis efficiency, quantity of residual blood cell debris, and microbial cell intactness.

In one example embodiment, the blood lysis reagent may further comprise an antifoaming agent comprising an emulsion of polydimethylsiloxane containing an appropriate non-ionic surfactant as an oil in water emulsifier and may have a composition such that after the blood lysis reagent is mixed with the blood culture sample, the concentration of the antifoaming agent emulsion lies within 0.005 to 1% (v/w), or for example, between 0.05 to 0.2% (v/w). In other example embodiments, the concentration of antifoaming agent emulsion in the final mixture may range between 0.01 and 0.05%. It will be understood that a suitable concentration of antifoaming agent may vary depending on one or more factors, such as, but not limited to, the concentration of other components of the blood lysis reagent, and the concentration of microbial cells in the blood culture sample. It will be understood that a suitable antifoaming agent composition and concentration can be determined, for a given set of conditions, by following the experimental methods described herein, in order to investigate the effect of antifoaming agent concentration and composition on one or more performance metrics, such as, but not limited to, a quantity of foam generated during automated operations involving the mixing and/or separation process, and the pressure required to deliver fluids.

Recovering Viable Microbial Cells Using Type 3 Blood Lysis Reagent

In view of the aforementioned success of the type 3 blood lysis reagent to facilitate the effective lysis of blood cells in a sample and to support the automated separation of intact microbial cells, the present inventors investigated the viability of microbial cells that were separated after contact with a type 3 lysis reagent. Although applications such as those involving nucleic acid detection or MALDI for microbial cell identification may only require that the separated microbial cells are separated with intact nucleic acids or proteins, other applications, such as applications involving the subsequent growth of the separated microbial cells (e.g. antimicrobial susceptibility testing or conventional growth-based identification methods) require that the separated microbial cells are viable (i.e. capable of cell division).

The present inventors first considered the feasibility of using a type 1 blood lysis reagent for the separation of viable microbial cells from a sample containing blood cells. The type 1 blood lysis reagent employs saponin and SPS. Although saponin is known to preserve microbial cell viability, it was shown in FIG. 5A that a type 1 blood lysis reagent composition that includes saponin and SPS but does not include a non-ionic surfactant or an alkaline pH buffer fails to sufficiently digest lysed blood cells in whole blood samples having volumes above approximately 1 mL, resulting in the presence of blood cell debris that can be problematic during automated separation (e.g. centrifugation and filtration). For this reason, a type 1 blood lysis reagent was deemed to be ineffective for applications involving automated blood cell lysis and automated separation of viable microbial cells.

The inventors then considered the feasibility of a type 2 blood lysis reagent for applications involving automated blood cell lysis and automated separation of viable microbial cells. Although type 2 blood lysis reagents have been shown to be capable of digestion of blood residue for a wide range of whole blood volumes (see, for example, FIG. 5B), such reagents, in the absence of the protective contribution of saponin, result in the loss of viability for a wide range of microbial cell species.

The present inventors therefore concluded that a type 3 blood lysis reagent would be most suitable for the automated lysis of blood cells and the subsequent automated separation of viable microbial cells. A series of experiments were performed to investigate the effect of various components of type 3 blood lysis reagents on the viability of Gram-positive and Gram-negative species when processing whole blood samples, and additional experiments were performed to demonstrate the extraction of viable microbial cells from blood culture samples using a type 3 blood lysis reagent. These experiments are described in detail below and demonstrate the suitability of type 3 blood lysis reagents for the automated separation of viable microbial cells.

Experimental Study of Effect of Type 2 and Type 3 Blood Lysis Reagent Exposure on Viability of *Staphylococcus aureus* in Whole Blood In a first experiment, the recovery of *Staphylococcus aureus* cells was assessed after exposure of the cells to type 2 and type 3 blood lysis reagents. This Gram-positive bacterium is expected to survive the harsher conditions contributed by Triton X-100 and an alkaline pH. Thus, both type 2 and type 3 reagents were assessed in the present experiment.

Example type 3 blood lysis reagent solutions were prepared by combining 10 ml of a carbonate-bicarbonate buffer solution prepared with a buffer concentration of 200 mM and a pH of 10 with 10 ml of a solution having a concentration of 40 mg/ml of SPS, a saponin concentration of 60 mg/ml, and 3% w/v of Triton X-100 to obtain reagent solutions having a volume of 20 ml, an SPS concentration of 20 mg/ml, a saponin concentration of 30 mg/ml, a Triton X-100 concentration of 1.5% w/v, a buffer concentration of 100 mM, and pH values were in the range of 9.5-10. After mixing 5 ml of the blood lysis reagent with 3 ml of the whole blood sample, the SPS concentration was 12.5 mg/mL, the saponin concentration was 18.75 mg/mL, the Triton X-100 concentration was 0.94% w/v, the pH value was approximately 9.5, and the effective buffer concentration was 62.5 mM.

The type 2 blood lysis reagent solutions were prepared by combining 10 ml of a carbonate-bicarbonate buffer solution prepared with a buffer concentration of 200 mM and a pH of 10 with 10 ml of a solution having a concentration of 40 mg/ml of SPS, and a Triton X-100 concentration of 3% w/v to obtain reagent solutions having a volume of 20 ml, an SPS concentration of 20 mg/ml, a Triton X-100 concentration of 1.5% w/v, a buffer concentration of 100 mM, and pH values were in the range of 9.5-10. After mixing 5 ml of the blood lysis reagent with 3 ml of the whole blood sample, the SPS concentration was 12.5 mg/mL, the Triton X-100 concentration was 0.94% w/v, the pH value was in the range of 9.2-9.5 and the effective buffer concentration was 62.5 mM.

Spiked whole blood samples or spiked phosphate buffer samples containing *Staphylococcus aureus* were prepared according to the method of Examples 2 and 3, respectively. Centrifugal separation was subsequently performed according to the methods provided in Examples 13 and 14 below for spiked phosphate buffer sample as a spiked control and spiked whole blood samples (using both type 3 and type 2 blood lysis reagents), respectively. The cell suspensions were plated on tryptic soy agar with 5% sheep blood and incubated at 37° C. overnight.

Figure 22A:
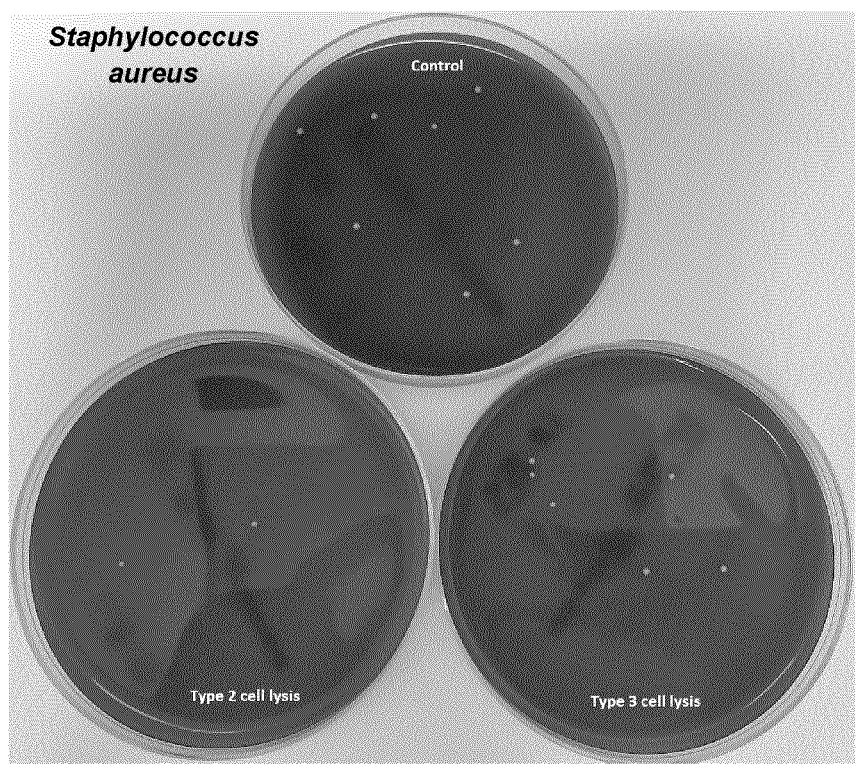
FIG. 22A shows agar plating results of S. aureus recovered from whole blood samples after contacting with type 2 and type 3 blood lysis reagents followed by centrifugal separation and concentration.

The results presented in FIG. 22A clearly demonstrate that the viability of *Staphylococcus aureus* cells is impaired by the type 2 blood lysis reagent. On the other hand, the presence of saponin in the type 3 blood lysis reagent preserves the viability of the recovered *Staphylococcus aureus* cells.

Experimental Study of Effect of Type 3 Blood Lysis Reagent Exposure on Viability of Selected Gram-Negative Microbial Cells in Whole Blood In contrast to Gram-positive *Staphylococcus aureus* bacterial cells of the preceding example, Gram-negative bacterial cells are expected to be less tolerant to the presence of Triton X-100 and an alkaline pH in the type 3 blood lysis reagent. Accordingly, experiments were performed using only type 3 blood lysis reagents. The experiments were performed to investigate the effect of different concentrations of carbonate-bicarbonate buffer and Triton X-100 on viability of Gram-negative microbial cells for a type 3 blood lysis reagent.

The example type 3 blood lysis reagent solutions were prepared by combining 10 ml of a carbonate-bicarbonate buffer solution prepared with a buffer concentration of 100 mM or 200 mM and a pH of 10 with 10 ml of a solution having a concentration of 40 mg/ml of SPS, a saponin concentration of 60 mg/ml, and a Triton X-100 concentration of 0% or 1.5% w/v to obtain reagent solutions having a volume of 20 ml, an SPS concentration of 20 mg/ml, a saponin concentration of 30 mg/ml, a Triton X-100 concentration of 0 or 0.75% w/v, a buffer concentration of 50 mM or 100 mM, and pH values were in the range of 9.5-10. After mixing 5 ml of the blood lysis reagent with 3 ml of the whole blood sample, the SPS concentration was 12.5 mg/mL, the saponin concentration was 18.75 mg/mL, the Triton X-100 concentration was 0% or 0.47% w/v, the pH value was in the range of 9.2-9.5, and the effective buffer concentration was 31.25 or 62.5 mM.

Spiked whole blood samples or spiked phosphate buffer samples containing *Proteus mirabilis* were prepared according to the method of Examples 2 and 3, respectively. Centrifugal separation was subsequently performed according to the methods provided in Examples 13 and 14 below for spiked phosphate buffer sample as a spiked control and spiked whole blood samples, respectively. The cell suspension was plated on tryptic soy agar with 5% sheep blood and incubated at 37° C. overnight.

Figure 22B:
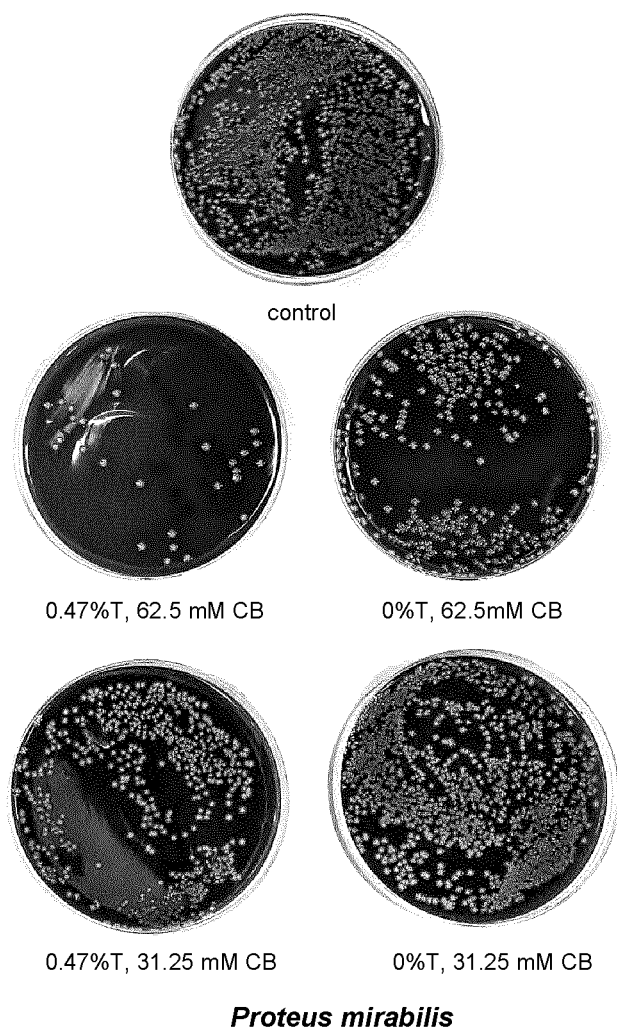
FIG. 22B shows agar plating results of P. mirabilis recovered from whole blood samples after contacting with type 3 blood lysis reagent containing saponin, SPS, a carbonate-bicarbonate buffer and Triton X-100 followed by centrifugal separation and concentration.

The results presented in FIG. 22B indicate that the viability of *Proteus mirabilis* cells can be dependent on the concentration of Triton X-100 and/or alkaline buffer. Indeed, as shown in the figure, the highest plate count (and thus highest viability) was observed for the case of the lowest effective buffer concentration (50 mM) and the lowest Triton X-100 concentration (0%).

Another experiment was performed to investigate the effect of different concentrations of carbonate-bicarbonate buffer and Triton X-100 on the viability of *Pseudomonas aeruginosa* cells. Type 3 blood lysis reagent solutions were prepared by combining 10 ml of a carbonate-bicarbonate buffer solution prepared with a buffer concentration of 100 mM, 150 mM or 200 mM and a pH of 10 with 10 ml of a solution having a concentration of 40 mg/ml of SPS, a saponin concentration of 60 mg/ml, and 0% or 0.75% w/v of Triton X-100 to obtain reagent solutions having a volume of 20 ml, an SPS concentration of 20 mg/ml, saponin concentration of 30 mg/ml, a Triton X-100 concentration of 0 or 0.375% w/v, a buffer concentration of 50 mM, 75 mM, or 100 mM, and pH values in the range of 9.5-10. After mixing 5 ml of the blood lysis reagent with 3 ml of the whole blood sample, the SPS concentration was 12.5 mg/mL, the saponin concentration of 18.75 mg/mL, the Triton X-100 concentration was 0% or 0.23% w/v, the pH value was in the range of 9.2-9.5, and the effective buffer concentration was 31.25 mM, 47 mM, or 62.5 mM.

Spiked whole blood samples or spiked phosphate buffer samples containing *Pseudomonas aeruginosa* were prepared according to the method of Examples 2 and 3, respectively. Centrifugal separation was subsequently performed according to the methods provided in Examples 13 and 14 below for spiked phosphate buffer sample as a spiked control and spiked whole blood samples, respectively. The cell suspension was plated on tryptic soy agar with 5% sheep blood and incubated at 37° C. overnight.

Figure 22C:
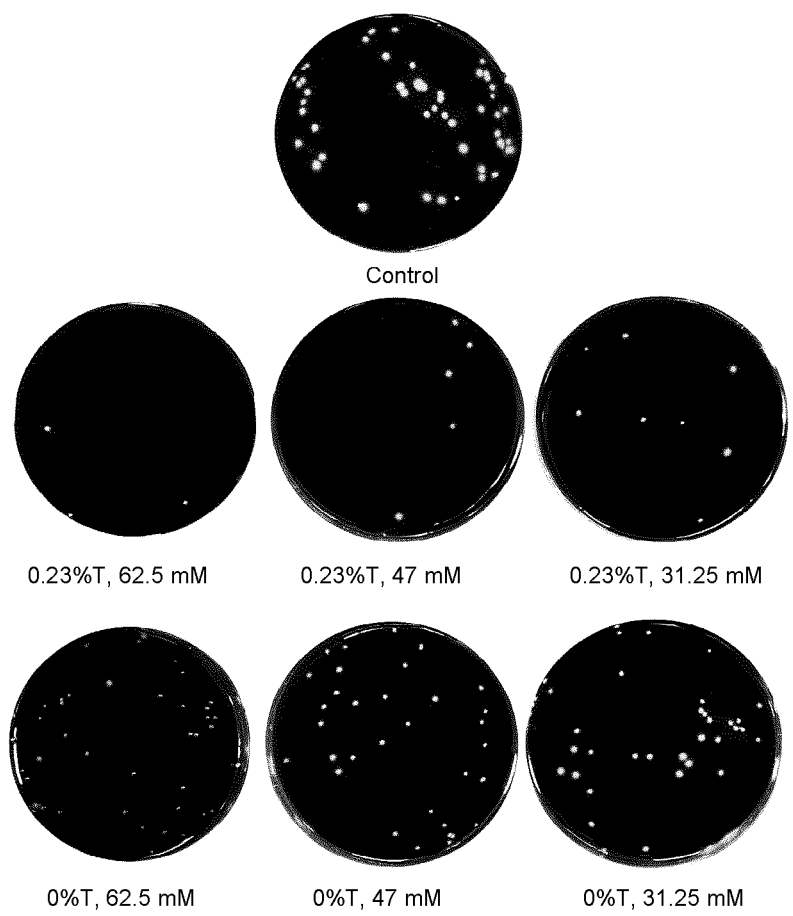
FIG. 22C shows agar plating results of P. aeruginosa recovered from whole blood samples after contacting with type 3 blood lysis reagent containing saponin, SPS, a carbonate-bicarbonate buffer and Triton X-100 followed by centrifugal separation and concentration.

The results presented in FIG. 22C indicate that the viability of *Pseudomonas aeruginosa* cells is also dependent on the concentration of Triton X-100 and also appears to be dependent on the concentration of the alkaline buffer. The preceding experiments indicate that the post-separation viability of the microbial cells appears to be inversely correlated with the concentration of the non-ionic surfactant and the buffer concentration of a type 3 lysis reagent for selected Gram-negative microbial cells. Indeed, the results suggest that improved post-separation viability may be obtained when the effective alkaline concentration and the non-ionic surfactant concentration are sufficiently low. The following experiments were designed to further investigate the effect of type 3 lysis reagent composition of post-separation microbial cell viability for reduced concentrations of the alkaline buffer and/or non-ionic surfactant.

Experimental Study of Effect of Absence of Non-Ionic Surfactant in Type 3 Blood Lysis Reagent on Recovery of Viable Microbial Cells An experiment was performed to investigate the effect of the absence of a non-ionic surfactant in a type 3 lysis reagent on the viability of recovered microbial cells for the processing of whole blood samples with a volume of 3 ml. Type 3 blood lysis reagent solutions were prepared by combining 10 ml of a carbonate-bicarbonate buffer solution, prepared with a buffer concentration of 100 mM or 50 mM at a pH of 10, with 10 ml of a solution having an SPS concentration of 40 mg/ml and a saponin concentration of 60 mg/ml to obtain blood lysis reagent solutions having a volume of 20 ml, an SPS concentration of 20 mg/ml, a saponin concentration of 30 mg/ml, a buffer concentration of 50 mM or 25 mM, and pH values in the range of 9.5-10. After mixing 5 ml of the blood lysis reagent with 3 ml of a whole blood sample, the SPS concentration was 12.5 mg/mL, the saponin concentration of 18.75 mg/mL, the pH value was in the range of 9.2-9.5, and the effective buffer concentration was 31.25 mM, or 15.6 mM. Spiked whole blood samples and spiked phosphate buffer samples containing *Pseudomonas aeruginosa, Proteus mirabilis* and *Staphylococcus aureus* cells were prepared according to the method of Examples 2 and 3, respectively. Centrifugal separation was subsequently performed according to the methods provided in Examples 13 and 14 for spiked phosphate buffer sample as a spiked control and spiked whole blood sample, respectively. The cell suspension was plated on tryptic soy agar with 5% sheep blood and incubated at 37° C. overnight.

Figures 22D, 23A:
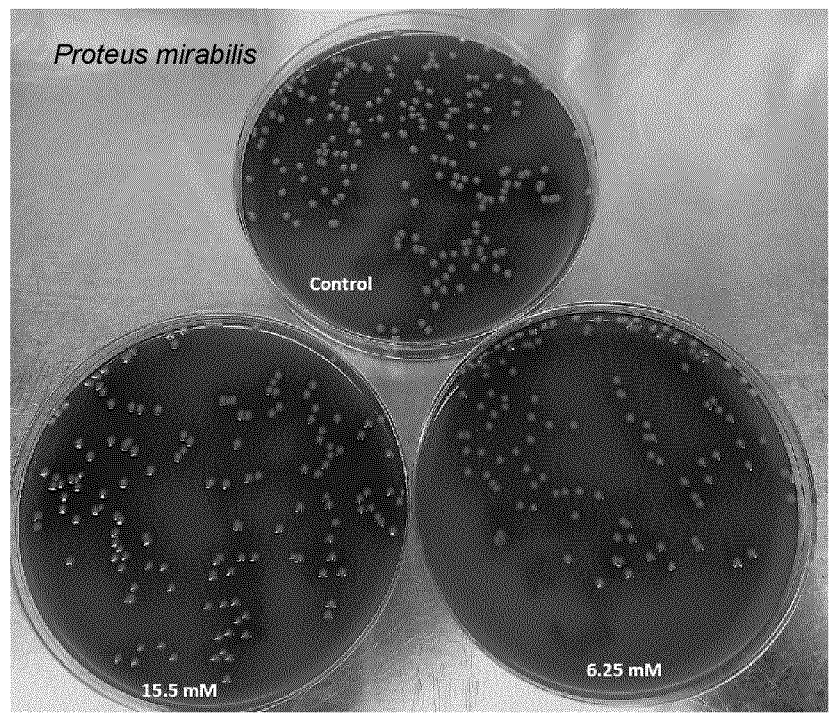
FIG. 22D shows agar plating results (plate counts) of P. aeruginosa (PA), P. mirabilis (PM), and S. aureus (SA) recovered from whole blood samples after contacting with type 3 blood lysis reagent containing saponin, SPS and a carbonate-bicarbonate buffer, followed by centrifugal separation and concentration.
FIG. 23A shows agar plating results of P. mirabilis recovered from whole blood samples after contacting with type 3 blood lysis reagent containing saponin, SPS and a different concentration of carbonate-bicarbonate buffer by convective mixing, followed by centrifugal separation and concentration.

The result presented in FIG. 22D show that the viable recovery of microbial cells was above 80% and above 60% for all microbial cell species for lysis reagents that are absent of a non-ionic surfactant when the post-mixing effective buffer concentration was 25 mM and 50 mM, respectively. This experimental study therefore confirmed the results shown in FIGS. 22B and 22C, indicating that when a type 3 lysis reagent is employed for the lysis of blood components of a whole blood sample with a moderate (e.g. 3 ml) volume for the purpose of extracting viable microbial cells, suitable viable cell recovery values can be obtained by preparing a lysis buffer in the absence of (or in the presence of low concentrations of) a non-ionic surfactant, with the recovery increasing for lower effective buffer concentrations for Gram-positive and Gram-negative species.

Experimental Study of Effect of Lower Buffer Concentrations in Type 3 Blood Lysis Reagent on Recovery of Viable Gram-Negative Microbial Cells The preceding study demonstrated that the recovery of viable microbial cells often increases when the effective buffer concentration of the lysis reagent is decreased. It has been observed by the inventors that as the effective buffer concentration is decreased, the viscosity of the sample-reagent mixture increases. The present study was performed to investigate the effect of lower (<50 mM) effective buffer concentrations on the recovery of viable bacterial cells.

Type 3 blood lysis reagent solutions were prepared by combining 10 mL of a carbonate-bicarbonate buffer solution prepared with a buffer concentration of 100 mM, 50 mM, or 20 mM at a pH of 10 with 10 ml of a solution having a concentration of 40 mg/ml of SPS, and a saponin concentration of 60 mg/ml, to obtain reagent solutions having a volume of 20 ml, an SPS concentration of 20 mg/ml, a saponin concentration of 30 mg/ml, and a buffer concentration of 50 mM, 25 mM, or 10 mM, and pH values were in the range of 9.5-10. After mixing 5 ml of the blood lysis reagent with 3 ml the whole blood sample, the SPS concentration was 12.5 mg/mL, the saponin concentration of 18.75 mg/mL, the pH value was in the range of 9.2-9.5, and the effective buffer concentration was 31.25 mM, or 15.6 mM, or 6.25 mM. Whole blood samples containing *Proteus mirabilis* cells and spiked controls were prepared according to the method of Examples 2 and 3, respectively. Centrifugal separation was subsequently performed according to the methods provided in Example 13 for spiked phosphate buffer sample as a spiked control. The blood lysis reagent and spiked whole blood sample were mixed by convective mixing and centrifugal separation was subsequently performed according to the methods provided in Example 15 below. The cell suspension was plated on tryptic soy agar with 5% sheep blood and incubated at 37° C. overnight.

The result presented in FIG. 23A shows that *Proteus mirabilis* cells have been recovered well for the effective carbonate-bicarbonate buffer concentration down to 6.25 mM.

Figure 23B:
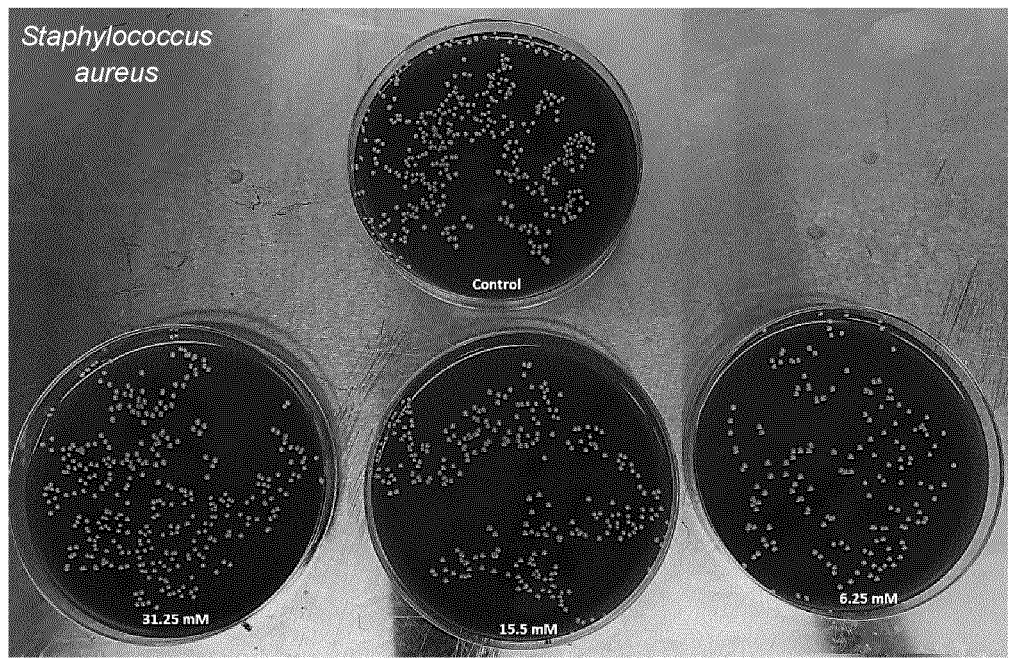
FIG. 23B shows agar plating results of S. aureus recovered from whole blood samples treated using type 3 blood lysis reagent containing saponin, SPS and a different concentration of carbonate-bicarbonate buffer by convective mixing, followed by centrifugal separation and concentration.

In order to illustrate that this low effective carbonate-bicarbonate buffer concentration is still appropriate for the recovery of *Staphylococcus aureus* cells, the above experiment was repeated using *Staphylococcus aureus* cells for effective buffer concentrations of 6.25 mM, 15.5 mM and 31.25 mM. The results are presented in FIG. 23B. As it is observed, there is a slight drop in the recovery of *Staphylococcus aureus* cells as the effective buffer concentration is decreased. Without intending to be limited by theory, the increased viscosity of the resulting blood-reagent mixture that results from the lower effective buffer concentration may impair the effectiveness of the centrifugal separation of the microbial cells due to a reduction in the sedimentation rate. Therefore, even though the viability of the microbial cells may not be impacted by the decrease in effective buffer concentration, the lower sedimentation rate during centrifugation may result in a reduced recovery of viable microbial cells, as some viable microbial cells remain in the supernatant and are inadvertently removed during wash operations.

Experimental Study of Effect of High Whole Blood Volumes (>3 ml) on Recovery of Viable Microbial Cells for Type 3 Blood Lysis Reagent The present experiments were performed to investigate the effect of larger (e.g. >3 ml; 5 ml) whole blood volumes on the recovery of microbial cells after exposure to a type 3 lysis reagent. It was hypothesized that the higher viscosity of hemolysed blood that is often encountered in the case of large sample volumes could have an impact on the ability to achieve a high recovery. The type 3 blood lysis reagent solutions were prepared by combining 10 mL of a carbonate-bicarbonate buffer solution prepared with a buffer concentration of 100 mM pH of 10 with 10 ml of a solution having a concentration of 40 mg/ml of SPS, a saponin concentration of 70 mg/ml, and a Triton X-100 concentration of 0.3% or 0% w/v, to obtain reagent solutions having a volume of 20 ml, an SPS concentration of 20 mg/ml, saponin concentration of 35 mg/ml, a Triton X-100 concentration of 0.15% or 0% w/v, a buffer concentration of 50 mM, and pH values were in the range of 9.5-10. After mixing 5 ml of the blood lysis reagent with 5 ml the whole blood sample, the SPS concentration was 10 mg/mL, the saponin concentration was 17.5 mg/mL, the Triton concentration was 0.075% or 0% w/v, the pH value was in the range of 9.2-9.5, and the effective buffer concentration was 25 mM.

Spiked whole blood samples and spiked phosphate buffer samples containing *Proteus mirabilis, Pseudomonas aeruginosa*, or *Staphylococcus aureus* cells and spiked controls were prepared according to the method of Examples 2 and 3, respectively. Centrifugal separation was subsequently performed according to the methods provided in Example 13 for spiked phosphate buffer sample as a spiked control, with the exception that 5 mL volume of sample was used and 9.9 mL of the supernatant was removed. The blood lysis reagent and spiked whole blood sample were mixed by convective mixing and centrifugal separation was subsequently performed according to the methods provided in Example 15 below with the exception that 5 mL volume of sample was used. The cell suspension was plated on tryptic soy agar with 5% sheep blood and incubated at 37° C. overnight. The results are presented in FIGS. 23C, 23D, and 23E for *Staphylococcus aureus, Proteus mirabilis*, and *Pseudomonas aeruginosa*, respectively.

Figure 23C:
FIG. 23C shows agar plating results of S. aureus recovered from whole blood samples with a volume of 5 mL after contacting with type 3 blood lysis reagent containing saponin, SPS, a carbonate-bicarbonate buffer, and two different concentrations of Triton X-100 by convective mixing, followed by centrifugal separation and concentration.
Figure 23D:
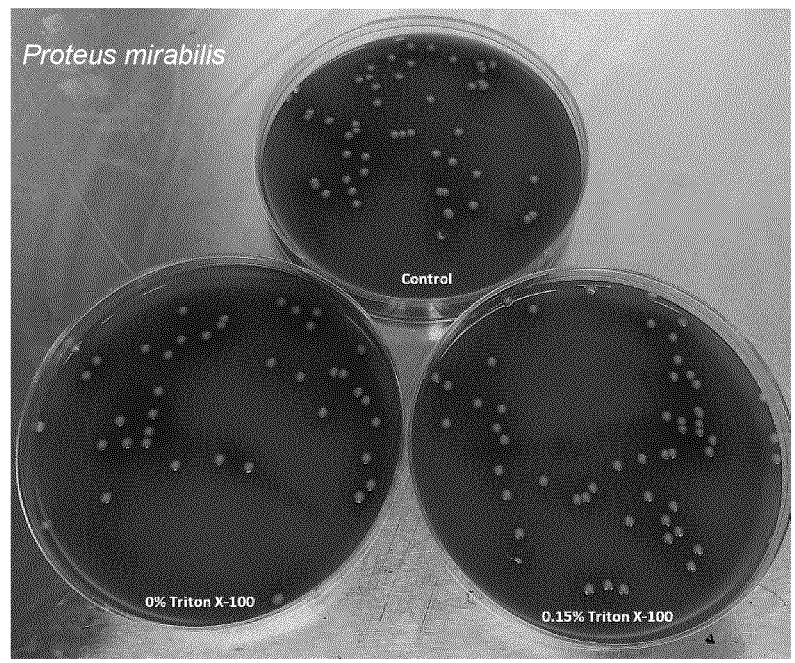
FIG. 23D shows agar plating results of P. mirabilis recovered from whole blood samples with a volume of 5 mL after contacting with type 3 blood lysis reagent containing SPS, saponin, a carbonate-bicarbonate buffer, and two different concentrations of Triton X-100 by convective mixing, followed by centrifugal separation and concentration.

FIGS. 23C and 23D demonstrate that for the case of the processing 5 ml whole blood samples containing *Staphylococcus aureus* and *Proteus mirabilis*, the post-separation recovery of viable microbial cells does not appear to be significantly dependent on the concentration of Triton X-100 for the low concentration range of 0-0.15% w/v that was tested.

Figure 23E:
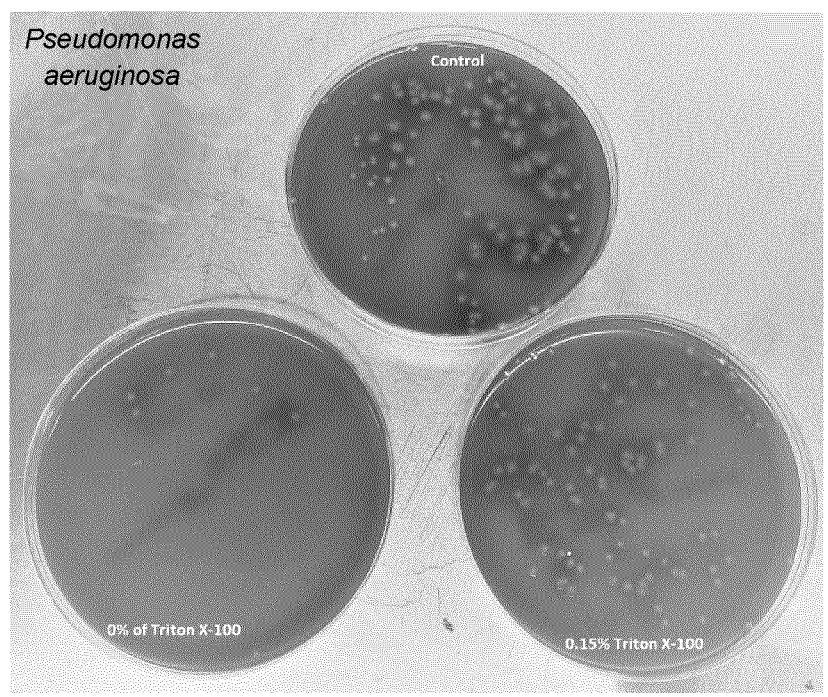
FIG. 23E shows agar plating results of P. aeruginosa (ATCC-35554) recovered from whole blood samples with a volume of 5 mL after contacting with type 3 blood lysis reagent containing SPS, saponin, a carbonate-bicarbonate buffer, and two different concentrations of Triton X-100 by convective mixing, followed by centrifugal separation and concentration.
Figure 23F:
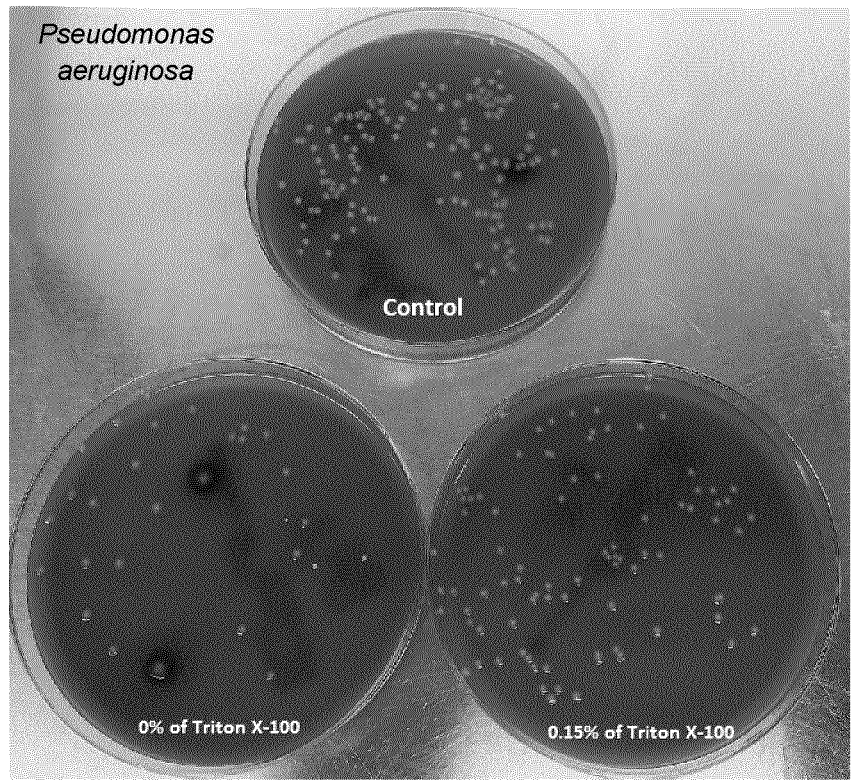
FIG. 23F shows agar plating results of P. aeruginosa (clinical isolate) recovered from whole blood samples with a volume of 5 mL after contacting with type 3 blood lysis reagent containing SPS, saponin, a carbonate-bicarbonate buffer, and two different concentrations of Triton X-100 by convective mixing, followed by centrifugal separation and concentration.

However, as it is observed in FIG. 23E, the recovery of *Pseudomonas aeruginosa* cells was low for the case of 0% Triton X-100. This observation was verified by repeating the experiment with different strain of *Pseudomonas aeruginosa* cells, which had been obtained from clinical isolates. The result, which is presented in FIG. 23F, like FIG. 23E, indicates that the presence of a small amount of Triton X-100 improves the recovery of viable cells. Without intending to be limited by theory, it is believed that this low recovery results from the observed high viscosity of the hemolyzed blood for the present large (5 mL) whole blood sample size. In particular, it is believed that while the viability of the microbial cells is not significantly impaired by contacting with the lysis reagent when Triton X-100 is absent, the high viscosity of the resulting blood-reagent mixture prevents the effective centrifugal separation of the *Pseudomonas aeruginosa* cells, which appear to be more susceptible to ineffective centrifugal separation than the other bacterial species investigated in the present experiments. Nonetheless, the results shown in FIG. 23E demonstrate that the addition of even a small concentration (0.15% w/v) of Triton X-100 (i.e. a concentration sufficiently low to avoid the loss of recovery observed in FIG. 22C) is sufficient to significantly lower the viscosity and enable high viable cell recovery for *Pseudomonas aeruginosa*.

In another example involving a high volume of whole blood, the effect of centrifugation time on the recovery of *Pseudomonas aeruginosa* cells was studied. A volume of 5 mL of the type 3 blood lysis reagent and 5 mL of whole blood sample were convectively mixed using the method of Example 15. The resulting mixture had a saponin concentration of 17.5 mg/mL, an SPS concentration of 10 mg/mL, a Triton X-100 concentration of 0.075%, a pH value in the range of 9.2-9.5, and an effective buffer concentration of 25 mM (in the final mixture). During the first step of sedimentation, three different centrifugation times of 5, 10, and 15 minutes were employed. However, the centrifugation time during subsequent wash operations were maintained at 2 minutes. Spiked phosphate buffer sample containing *Pseudomonas aeruginosa* cells was also prepared according to the method of Example 3.

Figure 23G:
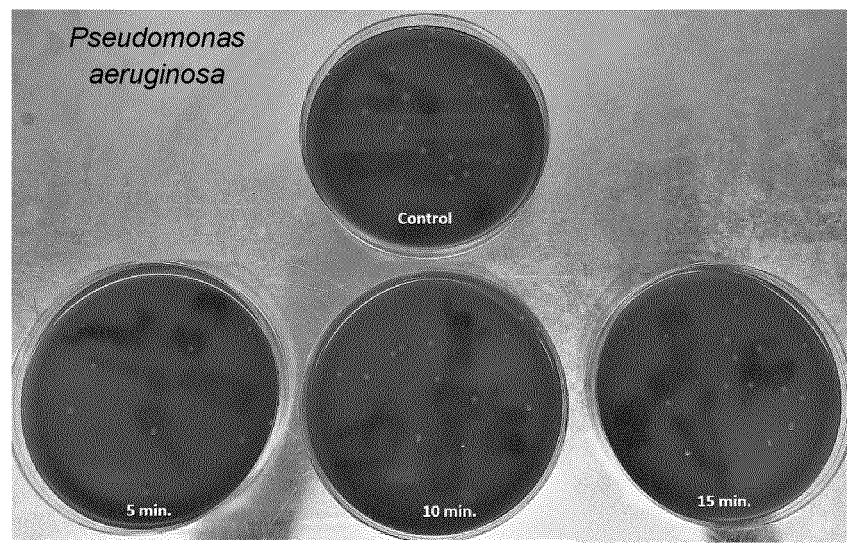
FIG. 23G shows agar plating results of P. aeruginosa (clinical isolate) recovered from whole blood samples with a volume of 5 mL after contacting with type 3 blood lysis reagent containing SPS, saponin, a carbonate-bicarbonate buffer and Triton X-100 by convective mixing, followed by centrifugal separation and concentration with three different centrifugation times of 5, 10, and 15 minutes.

Centrifugal separation was subsequently performed according to the methods provided in Example 13 for spiked phosphate buffer sample as a spiked control, with the exception that 5 mL volume of sample was used and 9.9 mL of the supernatant was removed. Photographs of the agar plates after plating the recovered suspensions are presented in FIG. 23G. The recovery corresponding the three centrifugation times were 39%, 83%, and 88%, respectively. These results support the hypothesis that the apparent reduction in viability seen in FIG. 23E (and FIG. 23F) may be caused predominantly by a loss of recovery upon centrifugal separation due to an increase in viscosity, which in turn causes a decrease in sedimentation rate. According to the results shown in FIG. 23G, the recovery of viable *Pseudomonas aeruginosa* cells, via centrifugal separation, after contact of a whole blood sample with a type 3 blood lysis buffer, may be increased by increasing the centrifugal separation time (and/or the centrifugal force, e.g. via an increase in rotation rate and/or radial separation).

In view of the results presented above, in some applications involving the automated separation of viable microbial cells after exposure to a type 3 lysis reagent, particularly in the case of the processing of whole blood having volumes of approximately 5 ml or more, a type 3 lysis reagent composition may be selected that strikes a balance between the microbial cell viability (after exposure to the type 3 blood lysis reagent), sufficient digestion of residual debris, and viscosity, in order to facilitate the automated separation of viable microbial cells for a wide variety of microbial species.

It is noted that the colonies formed via subsequent growth of separated microbial cells may be used for downstream diagnosis tests. For example, the colonies shown in FIGS. 23C, 23D, and 23E were tested by matrix assisted laser desorption/ionization (MALDI) as per the method described in Example 16. All three species of bacterial cells were identified via MALDI with a confidence level of 99.9%.

While the preceding results have demonstrated the successful extraction of viable microbial cells from whole blood samples, it will be understood that the example methods and compositions described herein that involve a type 3 blood lysis reagent may be extended to a wide variety of sample types. For example, a type 3 blood lysis reagent may be employed for the extraction of viable microbial cells from blood culture sample, such as a positive blood culture sample. Accordingly, a type 3 blood lysis reagent can be employed to facilitate the performing of phenotypic antimicrobial susceptibility testing directly from a blood culture sample, without requiring subculture.

Experimental Demonstration of Processing of Positive Blood Culture Samples with Type 3 Blood Lysis Reagent for Extraction of Viable Microbial Cells and Subsequent Microbial Identification and Antimicrobial Susceptibility Testing The cell suspension obtained by treating a positive blood culture sample may be subjected to downstream (subsequent) tests, such as tests suitable for determining one or both of the identity and antimicrobial susceptibility of microbial cells. In order to illustrate a non-limiting example of performing subsequent tests (assays) on viable microbial cells separated from a blood culture sample, positive blood culture samples were treated via contact with a type 3 blood lysis reagent and centrifugal separation was subsequently performed, and the resulting viable microbial cell suspensions were tested by VITEK® 2 for growth-based microbial identification (ID) and antimicrobial susceptibility (AST) or MALDI-TOF identification by VITEK® MS instruments.

Type 3 blood lysis reagent solutions were prepared by combining 10 ml of a carbonate-bicarbonate buffer solution prepared with a buffer concentration of 200 mM at pH of 10 with 10 ml of a solution having a concentration of 30 mg/ml of SPS, a saponin concentration of 75 mg/ml to obtain reagent solutions having a volume of 20 ml, an SPS concentration of 15 mg/ml, saponin concentration of 37.5 mg/ml, a buffer concentration of 100 mM and pH values were in the range of 9.5-10. After mixing 1 ml of the blood lysis reagent with 1 ml of the positive blood culture sample, the SPS concentration was 7.5 mg/mL, the saponin concentration was 18.75 mg/mL, the pH value was in the range of 9.2-9.5, and the effective buffer concentration was 50 mM.

Positive blood culture samples spiked with *Staphylococcus aureus*, *Escherichia coli*, *Pseudomonas aeruginosa* and *Klebsiella pneumoniae* were prepared according to the method of Example 10. Centrifugal separation was subsequently performed according to the methods provided in Example 12 below for positive blood culture samples. The microbial cells in the suspension were tested for microbial cell identification by MALDI (VITEK-MS-ID) as method described in Example 16, and metabolic-based identification (VITEK2-ID) and broth microdilution-based antibiotic susceptibility testing (VITEK2-AST) as method described in Example 17. In each case, reference positive controls also were tested by Examples 16 and 17 using colony growth obtained from direct plating of positive blood culture as described in Example 12.

The results are presented in FIGS. 24A to 24D and demonstrate very high agreement between the results obtained based on the direct processing of centrifugally separated microbial cells and the results obtained using positive control colonies. The MALDI identification results for all four microbial cells were in very high agreement, with 100% correct ID and over 99.4% identification confidence across all four microbial cell species. Similarly, the metabolic identification results for the VITEK2 system for all four microbial cells were in very high agreement, with 100% correct ID and over 95% identification probability across all four microbial cell species. The AST results using the VITEK2 system—based on direct AST from positive blood culture in the absence of subculture—also demonstrated excellent agreement with the results obtained using positive control colonies, with at least 94% S/I/R category agreement for all four microbial cell species. These results are therefore suggestive of a strong clinical equivalence between the present example direct methods and conventional colony-based methods for ID and AST from positive blood culture.

Experimental Demonstration of Processing of Whole Blood Samples with Type 3 Blood Lysis Reagent for Viable Microbial Cells Recovery and Subsequent Microbial Identification and Antimicrobial Susceptibility Testing The viable cells recovered from whole blood followed by colony formation on a solid phase growth media may be subjected to downstream (subsequent) tests, such as tests suitable for determining one or both of the identity and antimicrobial susceptibility of microbial cells. In order to illustrate a non-limiting example of performing subsequent tests (assays) on viable microbial cells recovered from a whole blood sample, low-concentration spiked whole blood samples were prepared for a wide variety of bacterial and fungal species, with three strains (2 ATCC strains and 1 clinical isolate) for each of: (i) 8 species of Gram-positive bacteria, (ii) 8 species of Gram-negative bacteria and (iii) 4 species of Fungi. The spiked whole blood samples were mixed with a type 3 blood lysis reagent and centrifugal separation was performed to recover viable cells in suspension. The recovered cell suspension was inoculated on a solid phase growth media and incubated for colony growth formation. The resulting colonies tested by VITEK® 2 for growth-based microbial identification (ID) and antimicrobial susceptibility (AST) or MALDI-TOF identification by VITEK® MS instruments.

Type 3 blood lysis reagent solutions were prepared by combining 10 ml of a carbonate-bicarbonate buffer solution prepared with a buffer concentration of 100 mM at pH of 10 with 10 ml of a solution having a concentration of 30 mg/ml of SPS, a saponin concentration of 150 mg/ml to obtain reagent solutions having a volume of 20 ml, an SPS concentration of 15 mg/ml, saponin concentration of 75 mg/ml, a buffer concentration of 50 mM and pH values were in the range of 9.5-10. After mixing 4 ml of the blood lysis reagent with 4 ml of the whole blood sample, the SPS concentration was 7.5 mg/mL, the saponin concentration was 37.5 mg/mL, the pH value was in the range of 9.2-95, and the effective buffer concentration was 25 mM.

Spiked whole blood samples with a volume of 4 ml containing the respective strains of microbial cells were prepared according to Example 2 below, with nominal concentration of 10 CFU/mL. Centrifugal separation was subsequently performed according to the methods provided in Example 14, with the exception that 4 mL volumes of spiked whole blood sample and blood lysis reagent were used. The cell suspension was plated on tryptic soy agar with 5% sheep blood and incubated as described in Example 14 for respective species. As a spiking control, the same concentration and volume aliquots of cells used for spiked whole blood sample were directly inoculated on tryptic soy agar with 5% sheep blood and incubated as described in Example 14. Upon visible colony formation, the number of colonies were counted and percentage of viable cell recovery was calculated by comparing the colony counts of spiked whole blood recovery vs. spiked control. The colony obtained from spiked whole blood samples were tested for microbial cell identification by MALDI (VITEK-MS-ID) following the method described in Example 16, and metabolic-based identification (VITEK2-ID) and broth microdilution-based antibiotic susceptibility testing (VITEK2-AST) following the method described in Example 17. In each case, reference positive controls also were tested by Examples 16 and 17 using colony growth obtained from respective spiked controls.

The viable cell recovery and the results from ID and AST assays are summarized in FIG. 25 for 24 strains of Gram-positive bacteria, 24 strains of Gram-negative bacteria, and 12 strains of fungi, respectively. The recovery results demonstrate very high average viable pathogen recovery (>90%) across all pathogen types for low (<10 CFU/ml) inoculations. The MALDI identification assays achieved 100% correct identification across all pathogen types. VITEK2 identification (metabolic) assays also achieved 100% correct identification across all pathogen types. The AST assays achieved >97% S/I/R category agreement across all pathogen types. These results demonstrate the feasibility of a type 3 blood lysis reagent for the efficient recovery of viable microbial cells from whole blood in low (clinically relevant) titers and the suitability of a type 3 blood lysis reagent for performing identification and antimicrobial susceptibility assays based on viable microbial cells separated from blood culture.

In view of the examples provided above, a wide variety of example compositions of blood lysis reagents the preserve the viability of microbial cells upon separation thereof, and methods of performing the selective lysis of blood cells and/or other eukaryotic cells and the extraction of viable microbial cells, are disclosed below. In one example embodiment, a method of performing selective lysis of blood cells and/or other eukaryotic cells in a sample, such as a whole blood sample, while preserving the viability of one or more microbial cells in the sample, may be performed by contacting the sample with a blood lysis reagent containing saponin, SPS, an alkaline buffer and a non-ionic surfactant, mixing the sample with the blood lysis reagent, incubating the mixture for a sufficient time to achieve lysis of the blood and/or eukaryotic cells within the sample, and separating the viable microbial cells.

When the loss in recovery due to injury of some Gram negative bacterial species, such as, but not limited to, *Pseudomonas aeruginosa, Proteus mirabilis*, and *Acinetobacter baumannii*, can be tolerated, the blood lysis reagent may have a composition such that after the blood lysis reagent is mixed with the sample, the concentration of saponin can be up to 100 mg/ml, the concentration of SPS can be up to 50 mg/ml, the concentration of non-ionic surfactant up to 3% w/v, the effective buffer concentration may be up 300 mM, and the pH of the final mixture may be up to 10.5. However, Gram negative bacterial cells may be sensitive to higher concentrations of non-ionic surfactant, higher buffer concentration, and the final mixture pH. In some implementations, it may be beneficial for these quantities to be maintained below the stated upper ranges with the constraint that the viscosity of the mixture and the residues from the blood cell debris are not too high to negatively impact the sedimentation process or impede the flow of intermediate fluids in the fluidic channels of the fluidic cartridge.

In one example embodiment, the blood lysis reagent may have a composition such that after the blood lysis reagent is mixed with the sample, the concentration of saponin lies between 3 and 60 mg/ml. In other example embodiments, the concentration of saponin in the final mixture may range between 10-30 mg/ml. It will be understood that a suitable concentration of saponin may vary depending on one or more factors, such, as, but not limited to, the types of microbial cells for which preservation of viability during separation is desired, the pH and/or effective buffer concentration in the final mixture, and the type of sample and quantity of sample. It will be understood that a suitable saponin concentration range can be determined, for a given set of conditions, by following the experimental methods described herein, in order to investigate the effect of saponin concentration on one or more performance metrics, such as, but not limited to, blood lysis efficiency, quantity of residual blood cell debris, and microbial cell viability.

In one example embodiment, the blood lysis reagent may have a composition such that after the blood lysis reagent is mixed with the sample, the concentration of SPS lies between 1.5 and 50 mg/ml. In other example embodiments, the concentration of SPS in the final mixture may range between 5-20 mg/ml. It will be understood that a suitable concentration of SPS may vary depending on one or more factors, such, as, but not limited to, the types of microbial cells for which preservation of viability during separation is desired, the pH and/or effective buffer concentration in the final mixture, and the type of sample and quantity of sample. It will be understood that a suitable SPS concentration range can be determined, for a given set of conditions, by following the experimental methods described herein, in order to investigate the effect of SPS concentration on one or more performance metrics, such as, but not limited to, blood lysis efficiency, quantity of residual blood cell debris, and microbial cell viability.

In one example embodiment, the blood lysis reagent may have a composition such that after the blood lysis reagent is mixed with the sample, the concentration of non-ionic surfactant lies within 0-3% w/v. In other example embodiments, the concentration of non-ionic surfactant in the final mixture may range between 0.5-2%. It will be understood that a suitable concentration of non-ionic surfactant may vary depending on one or more factors, such, as, but not limited to, the types of microbial cells for which preservation of viability during separation is desired, the pH and/or effective buffer concentration in the final mixture, the type of sample and quantity of sample. It will be understood that a suitable non-ionic surfactant concentration range can be determined, for a given set of conditions, by following the experimental methods described herein, in order to investigate the effect of non-ionic surfactant concentration on one or more performance metrics, such as, but not limited to, blood lysis efficiency, quantity of residual blood cell debris, and microbial cell viability.

In one example embodiment, the blood lysis reagent may have a composition such that after the blood lysis reagent is mixed with the sample, the pH lies within a range of 7.8-10. In other example embodiments, the pH of the final mixture may range between 8.2-9.5. In other example embodiments, the pH of the final mixture may lie within a range bounded by an upper pH value of 10, 9.9, 9.8, 9.7, 9.6 or 9.5, and bounded by a lower pH value of 8.0, 8.2, 8.4, 8.5, 8.6, 8.7, 8.8, 8.9 and 9.0. In some example embodiments, the buffer concentration may be selected such that the effective buffer concentration lies in the range of 10-300 mM. In other example embodiments, the buffer concentration may be selected such that the effective buffer concentration lies in the range of 30-100 mM.

It will be understood that a suitable pH may vary depending on one or more factors, such, as, but not limited to, the types of microbial cells for which preservation of viability during separation is desired, the effective buffer concentration in the final mixture, the initial pH of the blood lysis reagent prior to mixing with the sample, the type of sample and quantity of sample.

In some example embodiments, the blood lysis reagent may have a pH of 9-11 (or, for example, 9.5-10.5) and the buffer concentration (or buffer capacity) may be selected such that the pH, after mixing the blood lysis reagent with a sample, decreases to a final pH that is less than 10, less than 9.9, less than 9.8, less than 9.7, less than 9.6, or less than 9.5, and greater than 8.2, greater than 8.4, greater than 8.5, greater than 8.6, greater than 8.7, greater than 8.8, greater than 8.9, or greater than 9.0. Without intending to be limited by theory, it is suspected by the present inventors that an initial pH in the range of 9-11 can be beneficial for performing efficient digestion of blood cells, yet if such a high pH is maintained after lysis of the blood cells, the resulting high pH can negatively affect the viability of some microbial cells (e.g. such as *Pseudomonas aeruginosa* and *Proteus mirabilis*).

It will be understood that a suitable final pH and/or effective buffer concentration range can be determined, for a given set of conditions, by following the experimental methods described herein, in order to investigate the effect of pH and/or buffer concentration range on one or more performance metrics, such as, but not limited to, blood lysis efficiency, quantity of residual blood cell debris, and microbial cell viability.

In one example embodiment, the blood lysis reagent may further comprise an antifoaming agent comprising an emulsion of polydimethylsiloxane containing an appropriate non-ionic surfactant as an oil in water emulsifier and may have a composition such that after the blood lysis reagent is mixed with the sample, the concentration of the antifoaming agent emulsion lies within 0.005 to 0.5% (v/w). In other example embodiments, the concentration of antifoaming agent emulsion in the final mixture may range between 0.01 and 0.05%. It will be understood that a suitable concentration of antifoaming agent may vary depending on one or more factors, such as, but not limited to, the concentration of other components of the blood lysis reagent, the type of sample and quantity of sample. It will be understood that a suitable antifoaming agent composition and concentration can be determined, for a given set of conditions, by following the experimental methods described herein, in order to investigate the effect of antifoaming agent concentration and composition on one or more performance metrics, such as, but not limited to, a quantity of foam generated during automated operations involving the mixing and/or separation process, and the pressure required to deliver fluids.

In one example embodiment, a method of performing selective lysis of blood cells and/or other eukaryotic cells in a sample, while preserving the viability of one or more microbial cells in the sample, may be performed by contacting the sample with a blood lysis reagent containing saponin, SPS, and an alkaline buffer (e.g. with example concentrations and a pH as per the preceding example ranges), mixing the sample with the blood lysis reagent, and separating the microbial cells. While the inclusion of a non-ionic surfactant is beneficial in many applications, it is not necessary to achieve selective lysis in some applications, such as applications that are less sensitive to the presence of residual debris, and/or applications that do not involve downstream molecular amplification.

In one example embodiment, a method of performing selective lysis of blood cells and/or other eukaryotic cells in a sample, while preserving the viability of one or more microbial cells in the sample, may be performed by contacting the sample with a blood lysis reagent containing saponin and an alkaline buffer (e.g. with example concentrations and a pH as per the preceding example ranges), mixing the sample with the blood lysis reagent, and separating the microbial cells. While the inclusion of a non-ionic surfactant and SPS is beneficial in many applications, these components may not be necessary to achieve selective lysis in some applications, such as applications that are less sensitive to the presence of residual debris, and/or applications that do not involve downstream molecular amplification.

Example and non-limiting composition ranges are now provided herebelow for the processing of blood culture samples, such as positive blood culture samples and mid-culture samples, for the extraction of viable microbial cells. While the following example concentration ranges have been determined based on their suitability for facilitating colony growth on a solid phase growth media, broth microdilution based antimicrobial susceptibility testing, it will be understood that the concentration ranges provided below, and variations thereof, may be employed to perform blood cell lysis when other processes are performed that employ viable microbial cells.

In one example embodiment, the blood lysis reagent may have a composition such that after the blood lysis reagent is mixed with the blood culture sample, the concentration of saponin lies between 0.75 and 60 mg/ml. In other example embodiments, the concentration of saponin in the final mixture may range between 2.5-30 mg/ml. It will be understood that a suitable concentration of saponin may vary depending on one or more factors, such, as, but not limited to, the types of microbial cells for which preservation of intactness during separation is desired, the pH and/or effective buffer concentration in the final mixture, and the concentration of microbial cells in the blood culture sample. It will be understood that a suitable saponin concentration range can be determined, for a given set of conditions, by following the experimental methods described herein, in order to investigate the effect of saponin concentration on one or more performance metrics, such as, but not limited to, blood lysis efficiency, quantity of residual blood cell debris, and microbial cell intactness.

In one example embodiment, the blood lysis reagent may have a composition such that after the blood lysis reagent is mixed with the blood culture sample, the concentration of SPS lies between 0.35 and 50 mg/ml. In other example embodiments, the concentration of SPS in the final mixture may range between 1.25-20 mg/ml. It will be understood that a suitable concentration of SPS may vary depending on one or more factors, such as, but not limited to, the types of microbial cells for which preservation of intactness during separation is desired, the pH and/or effective buffer concentration in the final mixture, and the concentration of microbial cells in the blood culture sample. It will be understood that a suitable SPS concentration range can be determined, for a given set of conditions, by following the experimental methods described herein, in order to investigate the effect of SPS concentration on one or more performance metrics, such as, but not limited to, blood lysis efficiency, quantity of residual blood cell debris, and microbial cell intactness.

In one example embodiment, the blood lysis reagent may have a composition such that after the blood lysis reagent is mixed with the blood culture sample, the concentration of non-ionic surfactant lies within 0-3% w/v. In other example embodiments, the concentration of non-ionic surfactant in the final mixture may range between 0-2%. It will be understood that a suitable concentration of non-ionic surfactant may vary depending on one or more factors, such as, but not limited to, the types of microbial cells for which preservation of intactness during separation is desired, the pH and/or effective buffer concentration in the final mixture, and the concentration of microbial cells in the blood culture sample. It will be understood that a suitable non-ionic surfactant concentration range can be determined, for a given set of conditions, by following the experimental methods described herein, in order to investigate the effect of non-ionic surfactant concentration on one or more performance metrics, such as, but not limited to, blood lysis efficiency, quantity of residual blood cell debris, and microbial cell intactness.

In one example embodiment, the blood lysis reagent may have a composition such that after the blood lysis reagent is mixed with the blood culture sample, the pH lies within a range of 7.8-10. In other example embodiments, the pH of the final mixture may range between 8.2-9.5. In other example embodiments, the pH of the final mixture may lie within a range bounded by an upper pH value of 10, 9.9, 9.8, 9.7, 9.6 or 9.5, and bounded by a lower pH value of 8.0, 8.2, 8.4, 8.5, 8.6, 8.7, 8.8, 8.9 and 9.0. In some example embodiments, the buffer concentration may be selected such that the effective buffer concentration lies in the range of 2.5-300 mM. In other example embodiments, the buffer concentration may be selected such that the effective buffer concentration lies in the range of 5-100 mM.

It will be understood that a suitable pH may vary depending on one or more factors, such, as, but not limited to, the types of microbial cells for which preservation of intactness during separation is desired, the effective buffer concentration in the final mixture, the initial pH of the blood lysis reagent prior to mixing with the blood culture sample, and the concentration of microbial cells in the blood culture sample.

In some example embodiments, the blood lysis reagent may have a pH of 9-11 (or, for example, 9.5-10.5) and the buffer concentration (or buffer capacity) may be selected such that the pH, after mixing the blood lysis reagent with a blood culture sample, decreases to a final pH that is less than 10, less than 9.9, less than 9.8, less than 9.7, less than 9.6, or less than 9.5, and greater than 8.2, greater than 8.4, greater than 8.5, greater than 8.6, greater than 8.7, greater than 8.8, greater than 8.9, or greater than 9.0. Without intending to be limited by theory, it is suspected by the present inventors that an initial pH in the range of 9-11 can be beneficial for performing efficient digestion of blood cells, yet if such a high pH is maintained after lysis of the blood cells, the resulting high pH can negatively affect the intactness of some microbial cells (e.g. such as *Pseudomonas aeruginosa* and *Proteus mirabilis*).

It will be understood that a suitable final pH and/or effective buffer concentration range can be determined, for a given set of conditions, by following the experimental methods described herein, in order to investigate the effect of pH and/or buffer concentration range on one or more performance metrics, such as, but not limited to, blood lysis efficiency, quantity of residual blood cell debris, and microbial cell intactness.

In one example embodiment, the blood lysis reagent may further comprise an antifoaming agent comprising an emulsion of polydimethylsiloxane containing an appropriate non-ionic surfactant as an oil in water emulsifier and may have a composition such that after the blood lysis reagent is mixed with the blood culture sample, the concentration of the antifoaming agent emulsion lies within 0.005 to 0.5% (v/w). In other example embodiments, the concentration of antifoaming agent emulsion in the final mixture may range between 0.01 and 0.05%. It will be understood that a suitable concentration of antifoaming agent may vary depending on one or more factors, such as, but not limited to, the concentration of other components of the blood lysis reagent, and the concentration of microbial cells in the blood culture sample. It will be understood that a suitable antifoaming agent composition and concentration can be determined, for a given set of conditions, by following the experimental methods described herein, in order to investigate the effect of antifoaming agent concentration and composition on one or more performance metrics, such as, but not limited to, a quantity of foam generated during automated operations involving the mixing and/or separation process, and the pressure required to deliver fluids.

Example Applications of Type 3 Lysis Reagent Involving Separation of Viable and/or Intact Microbial Cells The preceding example embodiments have illustrated several example applications of the use of a type 3 lysis reagent after having obtained a suspension of viable and/or intact microbial cells by contacting a sample (e.g. a blood sample, such as a whole blood sample or a blood culture sample) with a type 3 blood lysis reagent for the selective lysis of blood cells and the subsequent separation of microbial cells using a separation method such as, but not limited to, centrifugation, filtration, immunomagnetic separation and microfluidic separation. The example applications described above for the subsequent processing of the separated microbial cells include molecular amplification assays (after performing lysis of the microbial cells), metabolic identification assays performed on viable separated cells, MALDI assays on separated viable and/or intact microbial cells, and phenotypic, growth-based antimicrobial susceptibility testing assays performed viable separated cells. It will be understood that these example applications are provided to illustrate a subset of the possible applications involving the processing of separated microbial cells after lysis of blood cells with a type 3 blood lysis reagent that includes saponin and SPS in an alkaline solution.

It will be understood that the example applications described herein may be performed according to manual methods, semi-automated methods, or fully-automated methods. Specific examples of semi-automated and automated systems, devices and methods for various applications are provided here below.

In some example embodiments, an integrated cartridge may be employed for performing microbial cell separation and subsequent processing in a fully automated and closed environment. For example, as illustrated in FIGS. 3A-3C, or variations thereof, an integrated cartridge may be employed for the fully automated processing of a sample, including the contacting of a sample with a type 3 blood lysis reagent, the separation of microbial cells to obtain a purified cell suspension, and performing of subsequent sample preparation and assay steps (e.g. electrical lysis and reverse transcription PCR).

In another example implementation, a cartridge such as the cartridge shown in FIGS. 3A-3C (or variations thereof) may be employed to perform the automated separation and concentration of microbial cells from a sample, yielding a purified microbial cell suspension that is available and suitable for subsequent assays after externally transferring the separated microbial cells, such as, but not limited to, molecular identification assays, MALDI identification assays, and growth-based assays such as phenotypic antimicrobial susceptibility testing.

For example, referring to FIGS. 3A-3C, a sealed port may be incorporated into the microfluidic device 699 that is in fluidic communication with an extraction chamber located in the microfluidic device 699. The extraction chamber may be in fluidic communication with the centrifugation chamber 501 through the channel 516 and a valve 519. After opening the valve 519, the separated cell suspension may be transferred to the extraction chamber, where it may be manually or robotically withdrawn (e.g. via a pipettor or a syringe) after breaking the seal. In another example implementation, a removable cap may be formed above the centrifugation chamber 502, permitting the robotic or manual removal of the microbial cell suspension for subsequent processing. It will be understood that although the example integrated cartridge shown in FIGS. 3A-3C employs automated centrifugation for performing separation, such an integrated cartridge may be modified to include an alternative separation modality, such as, but not limited to, filtration, immunomagnetic separation and microfluidic-based separation.

In some example embodiments, after having obtained a suspension of microbial cells that has been purified relative to the initial sample, the resulting suspension of microbial cells can be contacted with growth media (e.g. in the solid or liquid phase) in order to culture the separated microbial cells. Such a method may be beneficial for reducing the concentration of antibiotics that may be present in an initial sample, such that the separated microbial cells can be subsequently cultured with a significantly reduced (e.g. reduced by a factor exceeding 10, $10^2$, $10^3$, $10^4$ or higher) concentration of antibiotics, potentially achieving a growth rate and/or positivity rate that is improved relative to that which would be achievable without separation.

In one example implementation, after having obtained separated viable microbial cells, the separated viable microbial cells may be contacted with (e.g. dispersed on or over) solid phase growth media and incubated in an environment suitable for promoting microbial cell growth. Non-limiting examples of solid phase growth media include conventional agar, gelatin, guar gum, Xanthan gum. In some example implementations, the solid phase growth media may be chromogenic according to the type of microbial cell. In some embodiments chromogenic or fluorogenic substrate may be added to the agar media for identifying the microorganism by specific or non-specific staining of the colonies, as described, for example, in European Patent Application No. EP1088896A2.

It will be understood that the present example embodiment involving the direct formation of colonies from separated microbial cells may be performed in a manual method, a semi-automated method, or a fully-automated method. For example, in some example implementations, the microbial cells may be separated within an automated integrated cartridge, such as the cartridge shown in FIGS. 3A-3C or a variation thereof, and subsequently manually or robotically transferred to contact the solid phase growth media. In an alternative example implementation, the process may be fully automated within a closed integrated cartridge, which may be beneficial in avoiding the introduction of contaminants when transferring the separated microbial cells to the solid phase growth media.

The following examples are presented to enable those skilled in the art to understand and to practice embodiments of the present disclosure. They should not be considered as a limitation on the scope of the disclosure, but merely as being illustrative and representative thereof.

Examples

Example 1: Microbial Cell Culture Preparation

Gram-positive bacteria except *Staphylococcus aureus* and *Streptococcus pneumoniae* cell culture was prepared as follows:
1. Thirty µL of respective bacteria species and strain glycerol stock was inoculated in 3 mL of tryptic soy broth (TSB) and incubated at 37° C. for overnight with shaking at 150 rpm.
2. Tenfold diluted culture in TSB was incubated at 37° C. for 1 hour (*Enterococcus faecalis, Entercoccus faecium* and *Streptococcus agalactia*) or for 2 hr (*Straphylococcus epidermidis, Staphylococcus haemolyticus* and *Streptococcus pyogenes*).

Gram-negative bacteria except *Pseudomonas aeruginosa* cell culture was prepared as follows:
1. Thirty µL of respective bacteria species and strain glycerol stock was inoculated in 3 mL of TSB and incubated at 37° C. for overnight with shaking at 150 rpm.
2. Tenfold diluted culture in TSB was incubated at 37° C. for 1 hour (*Acinetobacter baumannii, Enterobacter cloacae* complex, *Enterobacter aerogenes, Escherichia coli, Klebsiella oxytoca, Klebsiella pneumoniae* and *Proteus mirabilis*) or for 2 hr (*Serratia marcescens*).

*Staphylococcus aureus* cell culture was prepared as follows:
Thirty µL of respective strain glycerol stock was inoculated in 3 mL of TSB and incubated at 37° C. for 3 hr with shaking at 150 rpm.

*Streptococcus pneumoniae* cell culture was prepared as follows:
Thirty µL of respective species or strain glycerol stock was inoculated in 3 mL of TSB and incubated at 37° C. for 3 hr with shaking at 80 rpm in the presence of $CO_2$ generating pouch.

*Pseudomonas aeruginosa*:
1. Six µL of *Pseudomonas aeruginosa* strain glycerol stock was streaked on tryptic soy agar (TSA) with 5% sheep blood plate and incubated at 37° C. for overnight (P1).
2. Bacteria colony was subcultured one more time on agar plate (P2).
3. One colony from the plate was inoculated in 3 ml of TSB and incubated at 37° C. for 3 hours with shaking at 150 rpm.

Fungi cell culture was prepared as follows:
1. Thirty µL of respective fungi species and strain glycerol stock was inoculated in 3 mL of TSB and incubated at 30° C. for overnight with shaking at 150 rpm.
2. Tenfold diluted culture in TSB was incubated at 30° C. for 2 hour (*Candida albicans, Candida glabrata, Candida parapsilosis* and *Candida tropicalis*).

Based on OD measurements, serial dilutions of the respective bacteria were prepared in TSB at a nominal concentration of $10^3$ CFU/mL.

Example 2: Preparation of Spiked Whole Blood Samples

Blood samples with volumes between 5-8 mL were drawn from healthy individuals into BD Vacutainer® SPS tubes. The tubes were kept at room temperature prior to being spiked with bacterial cells for an average period of 4 hours. Then, 50 µL of bacterial cell suspension stock having about $10^3$ CFU of respective bacterial cells was added to 5 mL of blood and mixed by gentle vortexing. Thus, the concentration of microbial cells is nominally about 10 CFU/mL.

Example 3: Preparation of Spiked Phosphate Buffer Samples

Bacterial cell suspension stock of 50 µL, having about $10^3$ CFU of respective bacterial cells was added to 5 mL of 1 mM Phosphate Buffer (PB) and mixed by gentle vortexing. Thus, the concentration of microbial cells are nominally about 10 CFU/mL.

Example 4: Sample Preparation of 1 mL Spiked Phosphate Buffer Samples in the Absence of Blood Lysis Reagent for Real Time RT-PCR Assay Spiked Control Sample preparation was performed for real time RT-PCR spiked controls as follows:
1. In a 15 ml centrifuge tube, 1 ml of spiked phosphate buffer was mixed with 1 ml of PB.
2. The centrifuge tube was vortexed for 1 minute.
3. The centrifuge tube was centrifuged at 4000 rpm for 3 min.
4. A supernatant of 1.9 ml was removed.
5. Four wash cycles were performed, where during each wash cycle, 0.9 ml of PB (wash buffer) was added and the solution was mixed for 10 second by gentle vortexing, centrifugation was performed at 4000 rpm for 3 min, and a supernatant of 0.9 ml was withdrawn and discarded such that 100 ul of residual liquid was retained.
6. The resulting cell suspension was subjected to heat lysis at 95° C. for 10 min.
7. RT-PCR reaction was prepared by mixing 1 ul of the heat lysate, 3 ul of real time RT-PCR master mix and 1 ul of target specific primer set and subjected to real time RT-PCR detection assay on an Illumina Real-Time Eco system thermal cycler.

Example 5: Sample Preparation of 1 mL Spiked Phosphate Buffer Samples Contacted with Blood Lysis Reagent Components for Real Time RT-PCR Assay Sample preparation was performed for spiked phosphate buffer samples as follows:
1. In a 15 ml centrifuge tube, 1 ml of spiked phosphate buffer was mixed with 1 ml of a blood lysis reagent (or subset of blood lysis reagent components).
2. The centrifuge tube was vortexed for 1 minute.
3. The centrifuge tube was centrifuged at 4000 rpm for 3 min.
4. A supernatant of 1.9 ml was removed.
5. Four wash cycles were performed, where during each wash cycle, 0.9 ml of wash buffer was added and the solution was mixed for 10 second by gentle vortexing, centrifugation was performed at 4000 rpm for 3 min, and a supernatant of 0.9 ml was withdrawn and discarded such that 100 ul of residual liquid was retained.
6. The resulting cell suspension was subjected to heat lysis at 95° C. for 10 min.
7. RT-PCR reaction was prepared by mixing 1 ul of the heat lysate, 3 ul of real time RT-PCR master mix and 1 ul of target specific primer set and subjected to real time RT-PCR detection assay on an Illumina Real-Time Eco system thermal cycler.

Example 6: Sample Preparation of 3 mL Spiked Phosphate Buffer Samples in the Absence of Blood Lysis Reagent for Real Time RT-PCR Assay Spiked Control Sample preparation was performed for real time RT-PCR spiked controls as follows:
1. In a 15 ml centrifuge tube, 3 ml of spiked phosphate buffer was mixed with 5 ml of PB.
2. The centrifuge tube was mixed by vortexing for 1 minute at maximum speed of the vortexer.
3. The centrifuge tube was centrifuged at 4000 rpm for 8 minutes.
4. A supernatant of 7.9 ml was removed.
5. Four wash cycles were performed, where during each wash cycle, 0.9 ml of wash buffer was added and the solution was mixed by gently vortexing, centrifugation was performed at 4000 rpm for 3 min, and a supernatant of 0.9 ml was withdrawn and discarded such that 100 ul of residual liquid was retained.
6. The resulting cell suspension was subjected to heat lysis at 95° C. for 10 min.
7. RT-PCR reaction was prepared by mixing 1 ul of the heat lysate, 3 ul of real time RT-PCR master mix and 1 ul of target specific primer set and subjected to real time RT-PCR detection assay on an Illumina Real-Time Eco system thermal cycler.

Example 7: Sample Preparation of 3 mL Spiked Whole Blood Samples for Real Time RT-PCR Assay Sample preparation was performed for spiked whole blood samples as follows:
1. In a 15 mL centrifuge tube, 5 ml of blood lysis reagent was added to 3 ml of sample.
2. The centrifuge tube was mixed by vortexing for 1 minute at maximum speed of the vortexer.
3. The centrifuge tube was centrifuged at 4000 rpm for 8 minutes.
4. A supernatant of 7.9 ml was removed.
5. Four wash cycles were performed, where during each wash cycle, 0.9 ml of wash buffer was added and the solution was mixed by gently vortexing, centrifugation was performed at 4000 rpm for 3 min, and a supernatant of 0.9 ml was withdrawn and discarded such that 100 ul of residual liquid was retained.
6. The resulting cell suspension was subjected to heat lysis at 95° C. for 10 min.
7. RT-PCR reaction was prepared by mixing 1 ul of the heat lysate, 3 ul of real time RT-PCR master mix and 1 ul of target specific primer set and subjected to real time RT-PCR detection assay on an Illumina Real-Time Eco system thermal cycler.

Example 8: Sample Preparation of 1 mL Spiked Whole Blood Samples for Real Time RT-PCR Assay Sample preparation was performed for spiked whole blood samples as follows:
1. In a 15 mL centrifuge tube, 1 ml of blood lysis reagent was added to 1 ml of sample.
2. The centrifuge tube was mixed by vortexing for 1 minute at maximum speed of the vortexer.
3. The centrifuge tube was centrifuged at 4000 rpm for 3 minutes.
4. A supernatant of 1.9 ml was removed.
5. Four wash cycles were performed, where during each wash cycle, 0.9 ml of wash buffer was added and the solution was mixed by gently vortexing, centrifugation was performed at 4000 rpm for 3 min, and a supernatant of 0.9 ml was withdrawn and discarded such that 100 ul of residual liquid was retained.
6. The resulting cell suspension was subjected to heat lysis at 95° C. for 10 min.
7. RT-PCR reaction was prepared by mixing 1 ul of the heat lysate, 3 ul of real time RT-PCR master mix and 1 ul of target specific primer set and subjected to real time RT-PCR detection assay on an Illumina Real-Time Eco system thermal cycler.

Example 9: Sample Preparation of 3 mL of Whole Blood Samples for Experimental Studies on Formation of Blood Debris Sample preparation of unspiked whole blood samples was performed as follows:
1. In a 15 mL centrifuge tube, 5 ml of blood lysis reagent was added to 3 ml of sample.
2. The centrifuge tube was mixed by vortexing for 1 minute at maximum speed of the vortexer.
3. The mixture was centrifuged at 4000 rpm for 7 minutes;
4. The supernatant was removed and 100 μL residue was left at the tube bottom,
5. Two wash cycles were performed, where during each wash cycle, 0.9 ml of wash buffer was added, centrifugation was performed at 4000 rpm for 3 min, and during the first wash cycle, a supernatant of 0.9 ml was withdrawn and discarded,
6. Photographs were taken of the resulting tubes to investigate the presence of blood debris.

Example 10: Preparing Positive Blood Culture Samples

Positive blood culture samples were prepared as follows:
1. The bacteria were spiked into 10 mL of whole blood samples at the nominal concentration of 5-10 CFU/ml.
2. FA Plus aerobic blood culture bottles were inoculated with 10 mL of spiked whole blood and incubated at 37° C. until the culture turns positive.

Example 11: Processing of Positive Blood Culture Samples by Convectively Mixing the Sample and the Blood Lysis Reagent The convective mixer employed for processing of a positive blood culture is presented in FIGS. 26A and 26B. It includes two 10 mL syringes (S1 and S2) with diameters of 15.9 mm and are connected by a tube T with ID=0.91 mm and a length of 10 cm. The sample preparation was performed as follows:
1. Drawing 1 mL of blood into one syringe (S1), as shown in FIG. 26A;
2. Drawing 1 mL of blood lysis reagent into another syringe (S2), as shown in FIG. 26A;
3. Drawing the 1 mL of blood lysis reagent from S2 to S1 with a flow rate of 90 mL/min, shown in FIG. 26B;
4. Drawing 2 mL of blood+blood lysis reagent mixture into S2; (not shown)
5. Drawing back the mixture into S1; (not shown)
6. Repeating steps 4 and 5, five times.
7. The hemolysed sample was transferred to 15 mL centrifuge tube.
8. The mixture was centrifuged at 4000 rpm for 3 minutes.
9. The supernatant was removed and 100 μL residual liquid was left at the tube bottom.
10. Two wash cycles were performed, where during each wash cycle, 0.9 ml of wash buffer was added, centrifugation was performed at 4000 rpm for 3 min, and during the first wash cycle, a supernatant of 0.9 ml was withdrawn and discarded.
11. Photographs were taken of the resulting tubes to investigate the presence of blood debris.

Example 12: Processing of Positive Blood Culture Samples for Cell Suspension Recovery Sample preparation of positive blood culture sample was as follows:
1. In a 15 mL centrifuge tube, positive blood culture samples with a volume of 1 mL was mixed with 1 mL of blood lysis reagent.
2. The centrifuge tube was mixed by vortexing for 1 minute at maximum speed of the vortexer.
3. The mixture was centrifuged at 4000 rpm for 3 minutes.
4. The 1.9 mL supernatant was removed and 100 μL residual liquid was left at the tube bottom.
5. Four wash cycles were performed, where during each wash cycle, 0.9 ml of wash buffer was added and the solution was mixed by gently vortexing, centrifugation was performed at 4000 rpm for 3 min, and a supernatant of 0.9 ml was withdrawn and discarded such that 100 ul of residual liquid was retained.
6. At the end of the wash cycle, the supernatant 0.9 was removed and the residual liquid of 100 uL was resuspended and taken as the recovered cell suspension.
7. As a positive control reference, the positive blood culture was inoculated on tryptic soy agar (TSA) with 5% sheep blood plate and incubated at 37° C. for 18 to 24 hrs.

Example 13: Sample Preparation of 3 mL Spiked Phosphate Buffer Samples in the Absence of Blood Lysis Reagent for Viable Cell Agar Plating Spiked Control Sample preparation was performed for viable cell agar plating spiked control as follows:
1. In a 15 ml centrifuge tube, 3 ml of spiked phosphate buffer was mixed with 5 ml of PB.
2. The centrifuge tube was mixed by vortexing for 1 minute at maximum speed of the vortexer.
3. The centrifuge tube was centrifuged at 4000 rpm for 8 minutes.

4. A supernatant of 7.9 ml was removed.
5. The resulting cell suspension was inoculated on agar plate and incubated at 37° C. for 18-24 hr for bacterial colony growth or at 30° C. for 24-72 hr for fungal colony growth. Agar plates for Streptococci species were incubated at 37° C. for 18-24 hr in the presence of $CO_2$ generating pouch.

Example 14: Sample Preparation of 3 mL Spiked Whole Blood Samples by Vortex Mixing for Viable Cell Recovery Agar Plating Experiments Sample preparation by vortex mixing was performed for viable microbial cell recovery from spiked whole blood samples as follows:
1. In a 15-mL centrifuge tube, 5 ml of blood lysis reagent was added to 3 ml of sample.
2. The centrifuge tube was mixed by vortexing for 1 minute at maximum speed of the vortexer.
3. The centrifuge tube was centrifuged at 4000 rpm for 8 minutes.
4. A supernatant of 7.9 ml was removed.
5. Four wash cycles were performed, where during each wash cycle, 0.9 ml of wash buffer was added and the solution was mixed by gently vortexing, centrifugation was performed at 4000 rpm for 3 min, and a supernatant of 0.9 ml was withdrawn and discarded such that 100 ul of residual liquid was retained.
6. The resulting cell suspension was inoculated on agar plate and incubated at 37° C. for 18-24 hr for bacterial colony growth or at 30° C. for 24-72 hr for fungal colony growth. Agar plates for Streptococci species were incubated at 37° C. for 18-24 hr in the presence of $CO_2$ generating pouch.

Example 15: Processing of 3 mL Spiked Whole Blood Samples by Convective Mixing for Viable Cell Recovery The convective mixer used for sample preparation whole blood is presented in FIGS. 26A and 26B. It includes two 10 mL syringes with diameters of 15.9 mm and are connected by a tube with ID=0.91 mm and a length of 10 cm. The sample preparation was performed as follows:
1. Drawing 3 mL of blood into one syringe (S1)
2. Drawing 5 mL of blood Lysis reagent into another syringe (S2)
3. Drawing the 5 mL of blood Lysis reagent from S2 to S1 with a flow rate of 90 mL/min
4. Drawing 8 mL of blood+blood Lysis reagent mixture into S2
5. Drawing back the mixture into S1
6. Repeating steps 4 and 5, five times
7. Emptying the content of the mix chamber into a 15 mL centrifuge tube
8. Centrifuging for 10 minutes at 4000 RPM
9. Removing supernatant and leaving 100 uL at the tube bottom
10. Adding 900 uL of wash buffer and mix by vortexing
11. Centrifuging for 2 minutes at 4000 RPM
12. Repeat steps 9-11 for 3 times
13. Removing supernatant and leaving 100 uL at the tube bottom
14. Plating the resulting cell suspension on agar plate and incubating at 37° C. for colony growth.

Example 16: Microbial Cell Identification by VITEK-MS®

Preparation of recovered cell suspension and reference control colony from positive blood culture in Example 12 and viable cell colony recovered from whole blood in Example 14 for VITEK-MS-ID was as follows:
1. The bacterial cell suspension of 1 uL was spotted on one sample area of VITEK MS-DS target slide, followed by addition of 1 uL of VITEK MS-CHCA (Alpha-cyano-4-hydroxy-cinnamic acid) and allowed to dry.
2. The bacterial colony sample was applied using a sterile 1 uL inoculation loop on one sample area of VITEK MS-DS target slide, followed by addition of 1 uL of VITEK MS-CHCA and allowed to dry.
3. The fungal colony sample was applied using a sterile 1 uL inoculation loop on one sample area of VITEK MS-DS target slide followed by addition of 1 uL of VITEK-MS-FA (Fomic acid) onto the sample and air drying. VITEK MS-CHCA of 1 uL was added on the dried sample and allowed to dry.
4. The species of spiked microorganism was identified by bioMérieux's VITEK® MS, a mass spectrometer system using matrix-assisted laser desorption/ionization—time to flight (MALDI-TOF).

Example 17: Microbial Cell Identification and Antimicrobial Susceptibility Testing by VITEK® 2

Preparation of recovered cell suspension and reference control colony from positive blood culture in Example 12 and viable cell colony recovered from whole blood in Example 14 for VITEK® 2 was as follows:
1. A volume of recovered bacterial cell suspension was added to 3.0 mL of 0.45% sterile saline in a provided test tube to prepare a standardized cell suspension for VITEK® 2 using DensiChek Plus turbidity meter. The turbidity of suspension was adjusted between 0.5 to 0.63 McFarland turbidity unit.
2. The bacterial colony sample was inoculated to 0.45% sterile saline as described above to prepare cell suspension of 0.5 to 0.63 McFarland turbidity unit.
3. The fungal colony sample was inoculated to 0.45% sterile saline as described above to prepare cell suspension of 1.8 to 2 McFarland turbidity unit.
4. Microbial identification and antimicrobial susceptibility testing were performed using bioMerieux VITEK® 2 60/XL. GP TEST KIT VTK2 (bioMerieux #21342), AST-GP67 (bioMerieux #22226) and AST-ST03 (bioMerieux #421040) were used for Gram-positive bacteria. GN TEST KIT VTK2 (bioMerieux #21341) and AST-N216 (bioMerieux #413066) were used for Gram-negative bacteria. YST TEST KIT VTK2 (bioMerieux #21343) and AST-Y508 (bioMerieux #420739) were used for yeast.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Therefore what is claimed is:

1. A method of separating microbial cells from a sample, the method comprising:
mixing a blood sample and a blood lysis reagent, the blood lysis reagent comprising saponin, sodium polyanethole sulfonate and an alkaline buffer, to obtain a mixture having a concentration of saponin between 0.75 and 60 mg/ml, a concentration of sodium polyanethole sulfonate between 0.35 and 50 mg/ml and a pH between 7.8 and 10; and
separating microbial cells from the mixture.

2. The method according to claim 1 wherein the blood lysis reagent has a pH in the range of 9.0-11.

3. The method according to claim 1 wherein the blood lysis reagent has a pH in the range of 9.5-10.5.

4. The method according to claim 1 wherein the blood lysis reagent is configured such that the pH of the mixture is in the range of 8.0-10.0.

5. The method according to claim 1 wherein the blood lysis reagent is configured such that the pH of the mixture is in the range of 8.5-9.5.

6. The method according to claim 1 wherein the blood lysis reagent is configured such that the pH of the mixture is in the range of 9.0-9.5.

7. The method according to claim 1 wherein the blood lysis reagent is configured such that the pH of the mixture is in the range of 8.8-9.8.

8. The method according to claim 1 wherein the blood lysis reagent is configured such that an effective buffer concentration of the mixture is in the range of 2.5-500 mM.

9. The method according to claim 1 wherein the blood lysis reagent is configured such that an effective buffer concentration of the mixture is in the range of 5-250 mM.

10. The method according to claim 1 wherein the blood lysis reagent is configured such that a concentration of saponin in the mixture is in the range of 3-60 mg/ml.

11. The method according to claim 1 wherein the blood lysis reagent is configured such that a concentration of saponin in the mixture is in the range of 10-30 mg/ml.

12. The method according to claim 1 wherein the blood lysis reagent is configured such that a concentration of sodium polyanethole sulfonate in the mixture is in the range of 3-60 mg/ml.

13. The method according to claim 1 wherein the blood lysis reagent is configured such that a concentration of sodium polyanethole sulfonate in the mixture is in the range of 1.5-50 mg/ml.

14. The method according to claim 1 wherein the blood lysis reagent is configured such that a concentration of sodium polyanethole sulfonate in the mixture is in the range of 5-20 mg/ml.

15. The method according to claim 1 wherein at least two reagents are separately stored, such that the saponin is stored separately from a basic component of the alkaline buffer.

16. The method according to claim 15 wherein the saponin is stored in an aqueous medium having a pH between 3.5 and 8.

17. The method according to claim 15 wherein the saponin is stored in an aqueous medium having a pH between 4 and 5.

18. The method according to claim 15 wherein the basic component of the alkaline buffer is stored in dry form.

19. The method according to claim 18 wherein the saponin is stored in a solution.

20. The method according to claim 1 wherein the blood lysis reagent further comprises a non-ionic surfactant.

21. The method according to claim 20 wherein the blood lysis reagent is configured such that a concentration of non-ionic surfactant in the mixture is in the range of 0-3% w/v.

22. The method according to claim 20 wherein the blood lysis reagent is configured such that a concentration of non-ionic surfactant in the mixture is in the range of 0.5-2.0% w/v.

23. The method according to claim 1 wherein the blood lysis reagent further comprises an antifoaming agent.

24. The method according to claim 23 wherein the antifoaming agent comprises an emulsion comprising polydimethylsiloxane and a non-ionic surfactant as an oil-in-water emulsifier.

25. The method according to claim 24 wherein the antifoaming agent is provided such that a concentration thereof in the mixture is in the range of 0.005-1% w/v.

26. The method according to claim 24 wherein the antifoaming agent is provided such that a concentration thereof in the mixture is in the range of 0.01-0.05% w/v.

27. The method according to claim 1 wherein the blood sample is a whole blood sample.

28. The method according to claim 27 wherein the whole blood sample has a volume exceeding 1 ml.

29. The method according to claim 27 wherein the whole blood sample has a volume exceeding 5 ml.

30. The method according to claim 1 wherein the sample is a blood culture sample.

31. The method according to claim 30 wherein the blood culture sample is a mid-culture blood culture sample obtained prior to a determination of positivity for the presence of microbial cells by an automated blood culture system.

32. The method according to claim 1 wherein the microbial cells are separated via centrifugation.

33. The method according to claim 1 wherein the microbial cells are separated via a separation method selected from the group consisting of filtration, immunomagnetic separation and microfluidic separation.

34. The method according to claim 1 further comprising:
performing an identification assay to identify the type of at least one microbial cell of the separated microbial cells.

35. The method according to claim 34 wherein the identification assay is a MALDI assay.

36. The method according to claim 1 further comprising incubating the separated microbial cells in the presence of growth media.

37. A method of separating microbial cells from a sample, the method comprising:
mixing a sample and a blood lysis reagent, the blood lysis reagent comprising saponin and an alkaline buffer, to obtain a mixture having a pH between 7.8 and 10 and a concentration of saponin suitable for effecting lysis of blood cells within the sample; and
separating microbial cells from the mixture.

38. The method according to claim 37 wherein the blood lysis reagent further comprises sodium polyanethole sulfonate.

* * * * *